US008679034B2

(12) United States Patent
Halperin et al.

(10) Patent No.: US 8,679,034 B2
(45) Date of Patent: Mar. 25, 2014

(54) TECHNIQUES FOR PREDICTION AND MONITORING OF CLINICAL EPISODES

(71) Applicant: Earlysense Ltd., Ramat Gan (IL)

(72) Inventors: Avner Halperin, Ramat Gan (IL); Itzhak Pinhas, Holon (IL); Yossi Gross, Moshav Mazor (IL)

(73) Assignee: EarlySense Ltd., Ramat Gan (IL)

( * ) Notice: Subject to any disclaimer, the term of this patent is extended or adjusted under 35 U.S.C. 154(b) by 0 days.

(21) Appl. No.: 13/750,962

(22) Filed: Jan. 25, 2013

(65) Prior Publication Data

US 2013/0144178 A1   Jun. 6, 2013

Related U.S. Application Data

(63) Continuation of application No. 11/782,750, filed on Jul. 25, 2007, now Pat. No. 8,403,865, which is a continuation-in-part of application No. 11/197,786, filed on Aug. 3, 2005, now Pat. No. 7,314,451, and a continuation-in-part of application No. 11/446,281, filed on Jun. 2, 2006, now Pat. No. 8,376,954, which is a continuation of application No. 11/048,100, filed on Jan. 31, 2005, now Pat. No. 7,077,810.

(60) Provisional application No. 60/674,382, filed on Apr. 25, 2005, provisional application No. 60/692,105, filed on Jun. 21, 2005, provisional application No. 60/541,779, filed on Feb. 5, 2004.

(51) Int. Cl.
*A61B 5/00* (2006.01)
*A61B 5/02* (2006.01)
*A61B 5/04* (2006.01)

(52) U.S. Cl.
USPC ............ 600/584; 600/508; 600/509; 600/515

(58) Field of Classification Search
USPC ................... 600/508–509, 515, 584
See application file for complete search history.

(56) References Cited

U.S. PATENT DOCUMENTS 5,620,003 A    4/1997  Sepponen
5,730,140 A    3/1998  Fitch
(Continued)

FOREIGN PATENT DOCUMENTS

EP         0860803       8/1998
JP       2001-327549    11/2001
(Continued)

OTHER PUBLICATIONS

International Search Report of PCT/IL2011/050045 dated Jul. 13, 2012.

(Continued)

*Primary Examiner* — Nicole F Lavert
(74) *Attorney, Agent, or Firm* — Rodney J. Fullor; Booth Udall Fuller, PLC

(57) ABSTRACT

Apparatus and methods are provided for monitoring a subject, including setting respective first and second thresholds that are different from one another, sensing at least one parameter of the subject, and analyzing the parameter to generate a score. If the score is between the first and second thresholds, an alert that is indicative of a condition of the subject is generated only after the subject awakes. If the score passes the second threshold, an alert that is indicative of the subject's condition is generated immediately. Other applications are also described.

6 Claims, 20 Drawing Sheets

(56) References Cited

U.S. PATENT DOCUMENTS

| | | |
|---|---|---|
| 6,631,281 B1 | 10/2003 | Kastle |
| 6,641,542 B2 | 11/2003 | Cho |
| 6,646,556 B1 | 11/2003 | Smith |
| 6,662,032 B1 | 12/2003 | Gavish |
| 6,666,830 B1 | 12/2003 | Lehrman |
| 6,719,708 B1 | 4/2004 | Jansen |
| 6,731,311 B2 | 5/2004 | Bufe |
| 6,745,060 B2 | 6/2004 | Diab |
| 6,751,498 B1 | 6/2004 | Greenberg |
| 6,752,766 B2 | 6/2004 | Kowallik |
| 6,754,516 B2 | 6/2004 | Mannheimer |
| 6,790,183 B2 | 9/2004 | Murphy |
| 6,821,258 B2 | 11/2004 | Reed |
| 6,822,564 B2 | 11/2004 | Al-Ali |
| 6,827,670 B1 | 12/2004 | Stark |
| 6,830,548 B2 | 12/2004 | Bonnet |
| 6,840,907 B1 | 1/2005 | Brydon |
| 6,856,141 B2 | 2/2005 | Ariav |
| 6,878,121 B2 | 4/2005 | Krausman |
| 6,893,404 B2 | 5/2005 | Ragnarsdottir |
| 6,955,647 B2 | 10/2005 | Rice |
| 6,980,679 B2 | 12/2005 | Jeung |
| 6,984,207 B1 | 1/2006 | Sullivan |
| 6,984,993 B2 | 1/2006 | Ariav |
| 6,988,989 B2 | 1/2006 | Weiner |
| 7,022,072 B2 | 4/2006 | Fox |
| 7,025,729 B2 | 4/2006 | de Chazal |
| 7,077,810 B2 | 7/2006 | Lange |
| 7,079,035 B2 | 7/2006 | Bock |
| 7,283,161 B2 | 10/2007 | Someya |
| 7,304,580 B2 | 12/2007 | Sullivan |
| 7,314,451 B2 | 1/2008 | Halperin |
| 7,390,299 B2 | 6/2008 | Weiner |
| 7,396,331 B2 | 7/2008 | Mack |
| 7,396,333 B2 | 7/2008 | Stahmann |
| 7,415,297 B2 | 8/2008 | Al-Ali |
| 7,428,468 B2 | 9/2008 | Takemura |
| 7,431,700 B2 | 10/2008 | Aoki |
| 7,433,827 B2 | 10/2008 | Rosenfeld |
| 7,439,856 B2 | 10/2008 | Weiner |
| 7,454,359 B2 | 11/2008 | Rosenfeld |
| 7,508,307 B2 | 3/2009 | Albert |
| 7,572,225 B2 | 8/2009 | Stahmann |
| 7,610,094 B2 | 10/2009 | Stahmann |
| 7,629,890 B2 | 12/2009 | Sullivan |
| 7,666,151 B2 | 2/2010 | Sullivan |
| 7,689,440 B2 | 3/2010 | Brown |
| 7,704,215 B2 | 4/2010 | Lewicke |
| 7,778,851 B2 | 8/2010 | Schoenberg |
| 7,860,583 B2 | 12/2010 | Condurso |
| 7,880,606 B2 | 2/2011 | Al-Ali |
| 7,896,813 B2 | 3/2011 | Sowelam |
| 7,938,782 B2 | 5/2011 | Stahmann |
| 7,952,475 B2 | 5/2011 | Ivanov |
| 7,959,574 B2 | 6/2011 | Bardy |
| 2001/0005773 A1 | 6/2001 | Larsen et al. |
| 2002/0099303 A1* | 7/2002 | Bardy .................. 600/515 |
| 2003/0004403 A1 | 1/2003 | Drinan |
| 2005/0027216 A1 | 2/2005 | Guillemaud et al. |
| 2005/0080349 A1 | 4/2005 | Okada et al. |
| 2006/0089856 A1 | 4/2006 | Kadhiresan |
| 2006/0258952 A1 | 11/2006 | Stahmann et al. |
| 2007/0024451 A1 | 2/2007 | Albert |
| 2007/0257564 A1 | 11/2007 | Kitade |
| 2007/0276202 A1 | 11/2007 | Raisanen |
| 2009/0164239 A1 | 6/2009 | Hayter |
| 2009/0299229 A1 | 12/2009 | Johnson |
| 2010/0217618 A1 | 8/2010 | Piccirillo |
| 2013/0174345 A1 | 7/2013 | Leu |

FOREIGN PATENT DOCUMENTS

| | | |
|---|---|---|
| JP | 2005-237479 | 9/2005 |
| WO | 2004006768 | 1/2004 |
| WO | 2004/091378 A2 | 10/2004 |
| WO | 2005/055824 A1 | 6/2005 |
| WO | 2007081629 | 7/2007 |

OTHER PUBLICATIONS

Oppenheim, A., and Schafer, R., "Discrete-Time Signal Processing", Prentice5' Hall, 1989, pp. 311-312 (1989).

Staderini, Enrico M., "UWB Radars in Medicine", IEEE Aerospace and Electronic Systems Magazine, 17(1):13-18 (2002).

Yien, HW et al., "Spectral analysis of systemic arterial pressure and heart rate signals as a prognostic tool for the prediction of patient outcome in the intensive care unit", Crit Care Med., 25(2):258-266 (1997).

Corresponding European Patent Application No. 12168737 European Search Report Sep. 3, 2012.

International Search Report for PCT/IL2013/050283 dated Aug. 28, 2013.

* cited by examiner

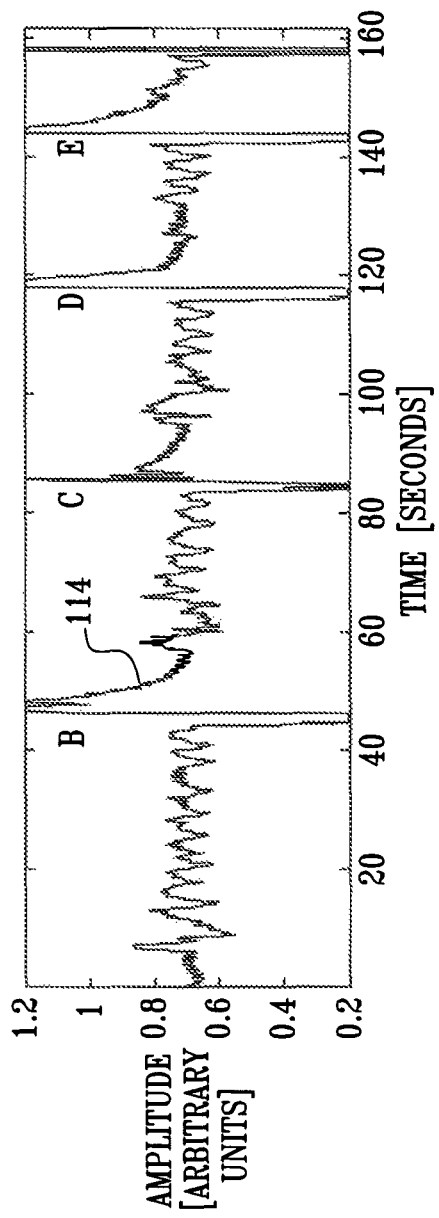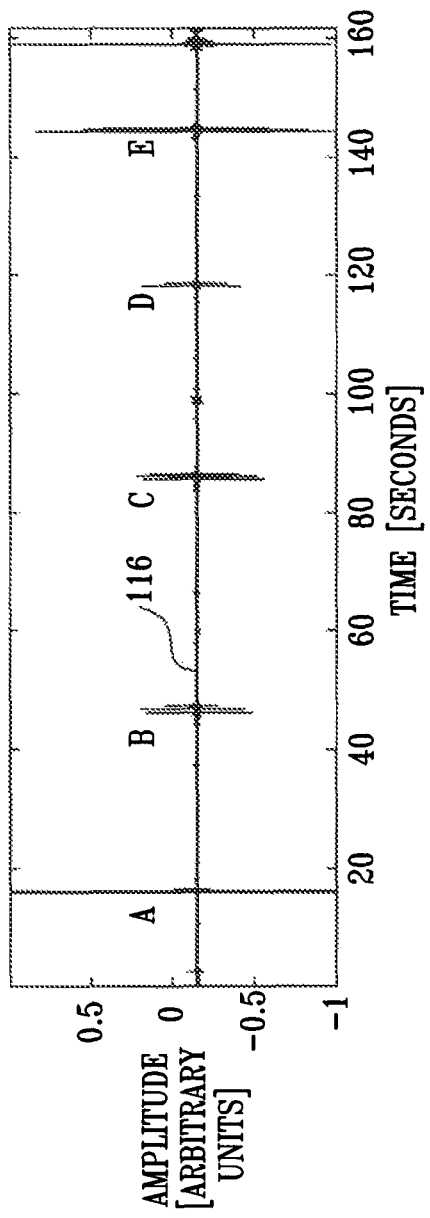

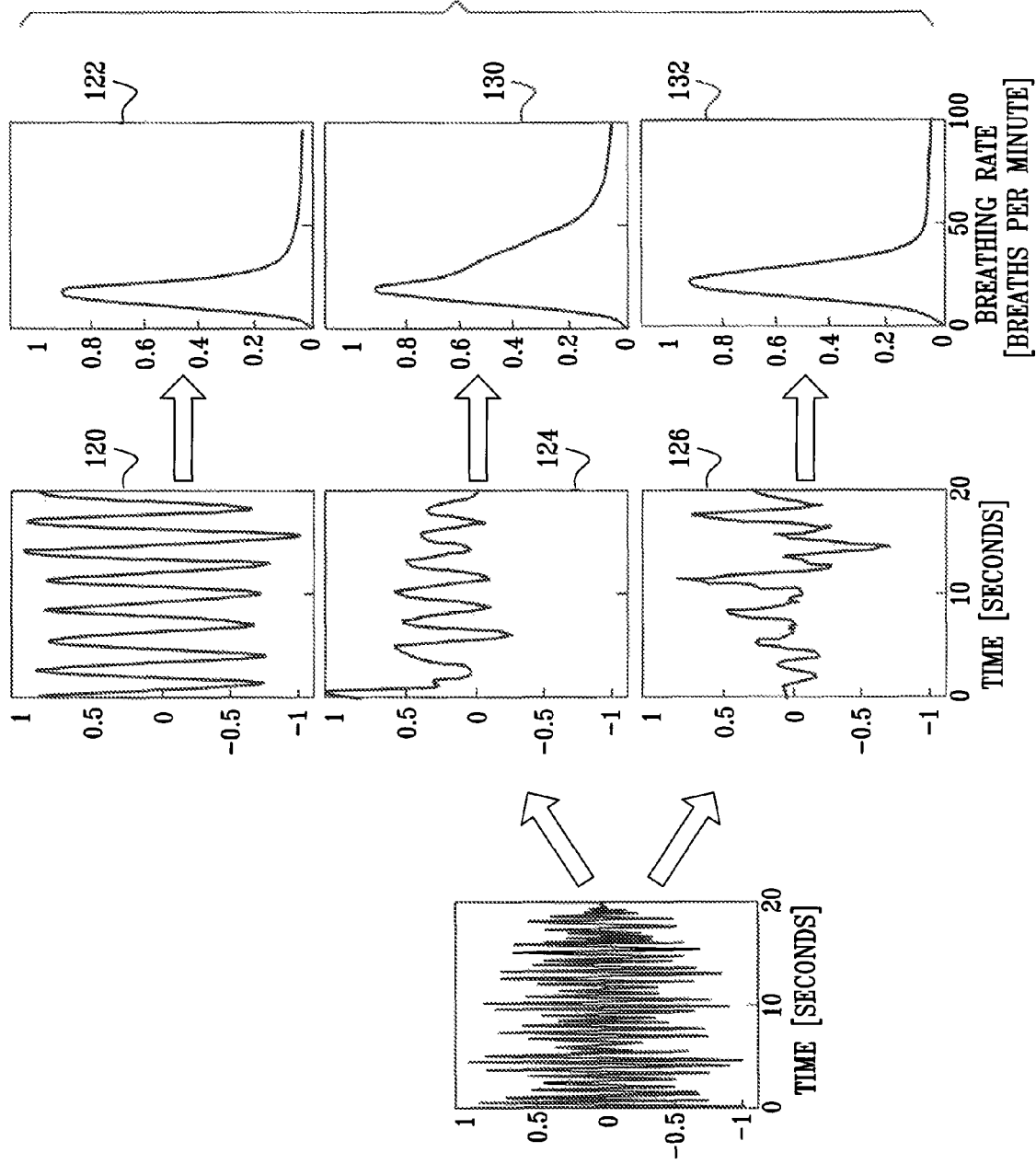

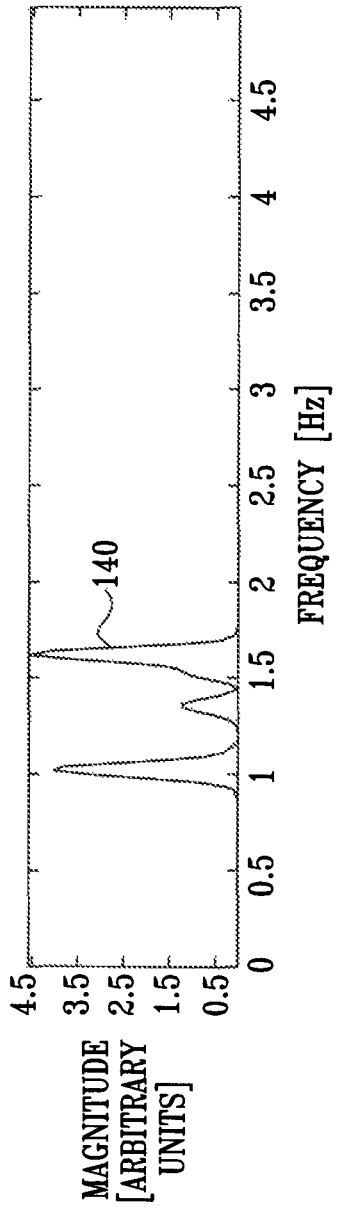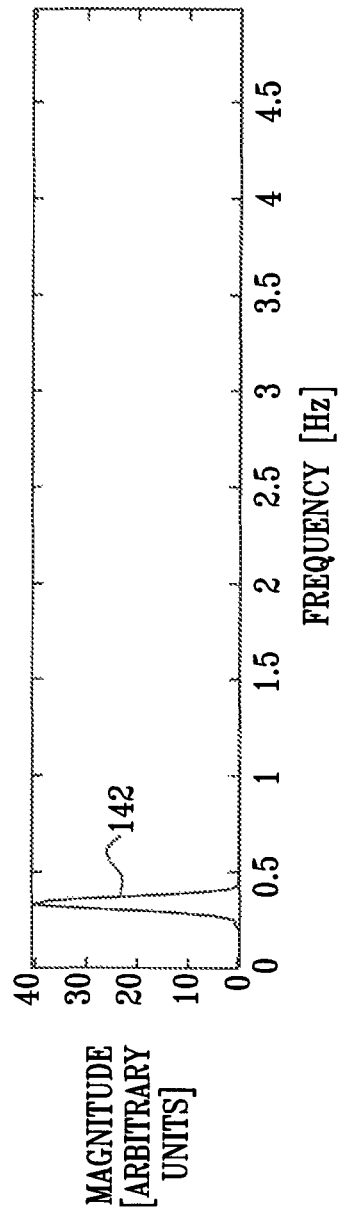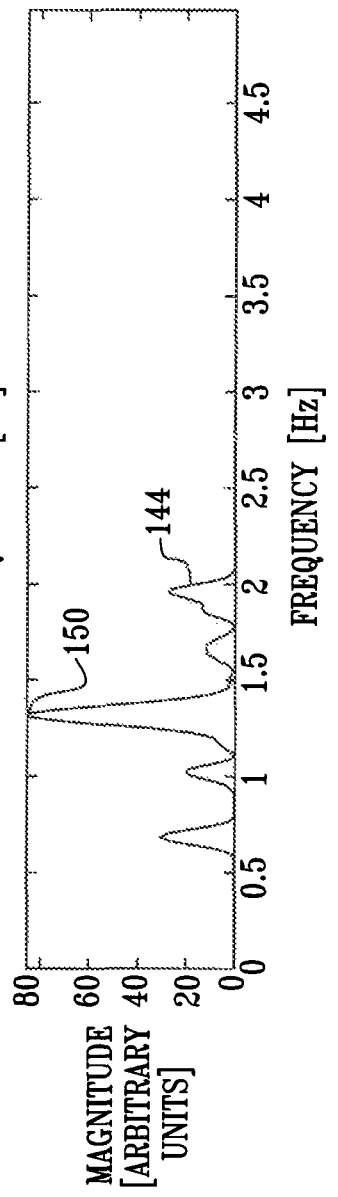

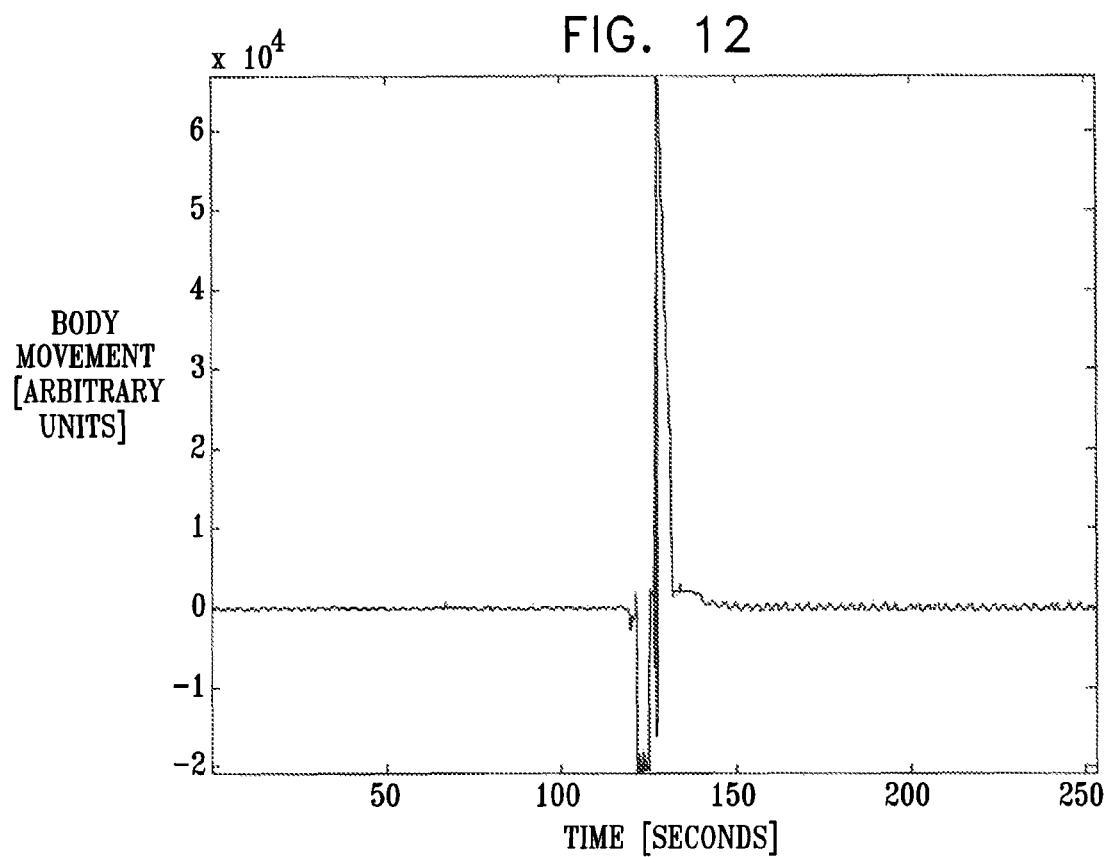
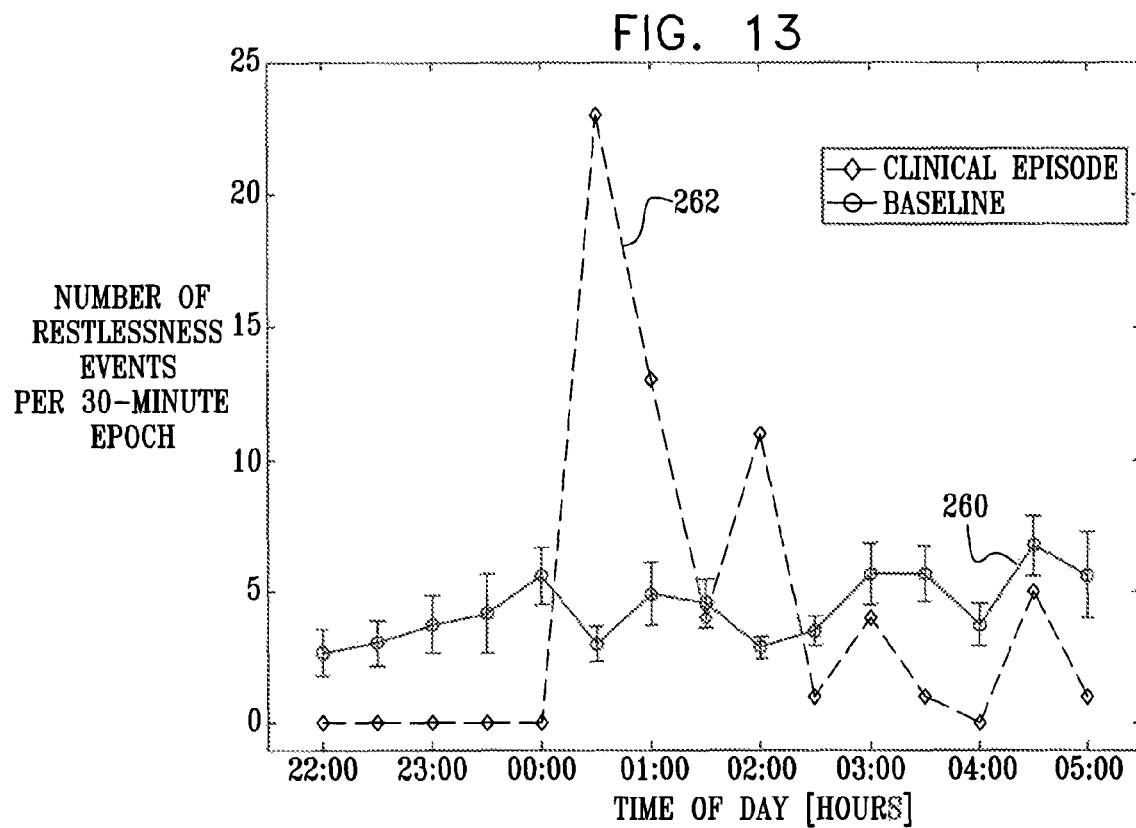

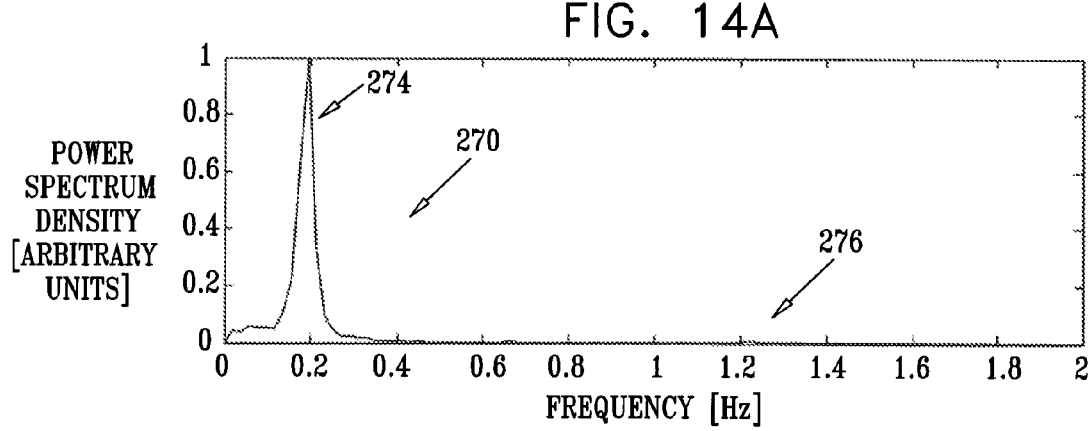
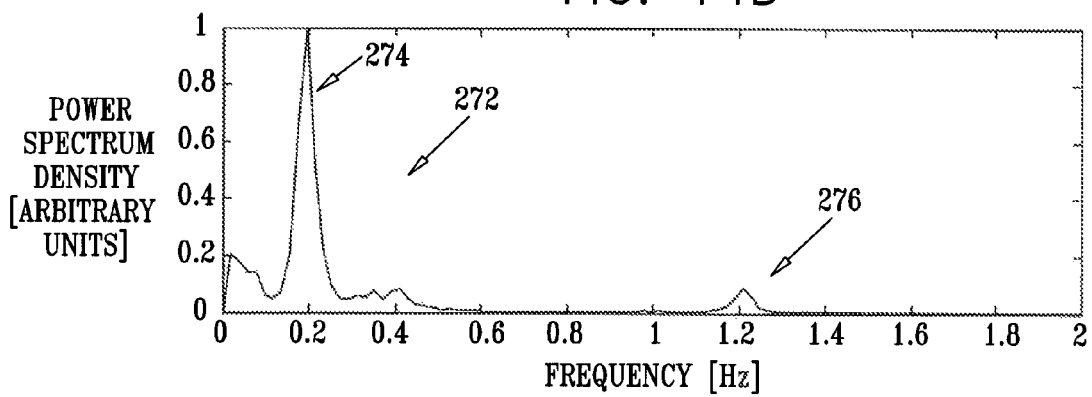

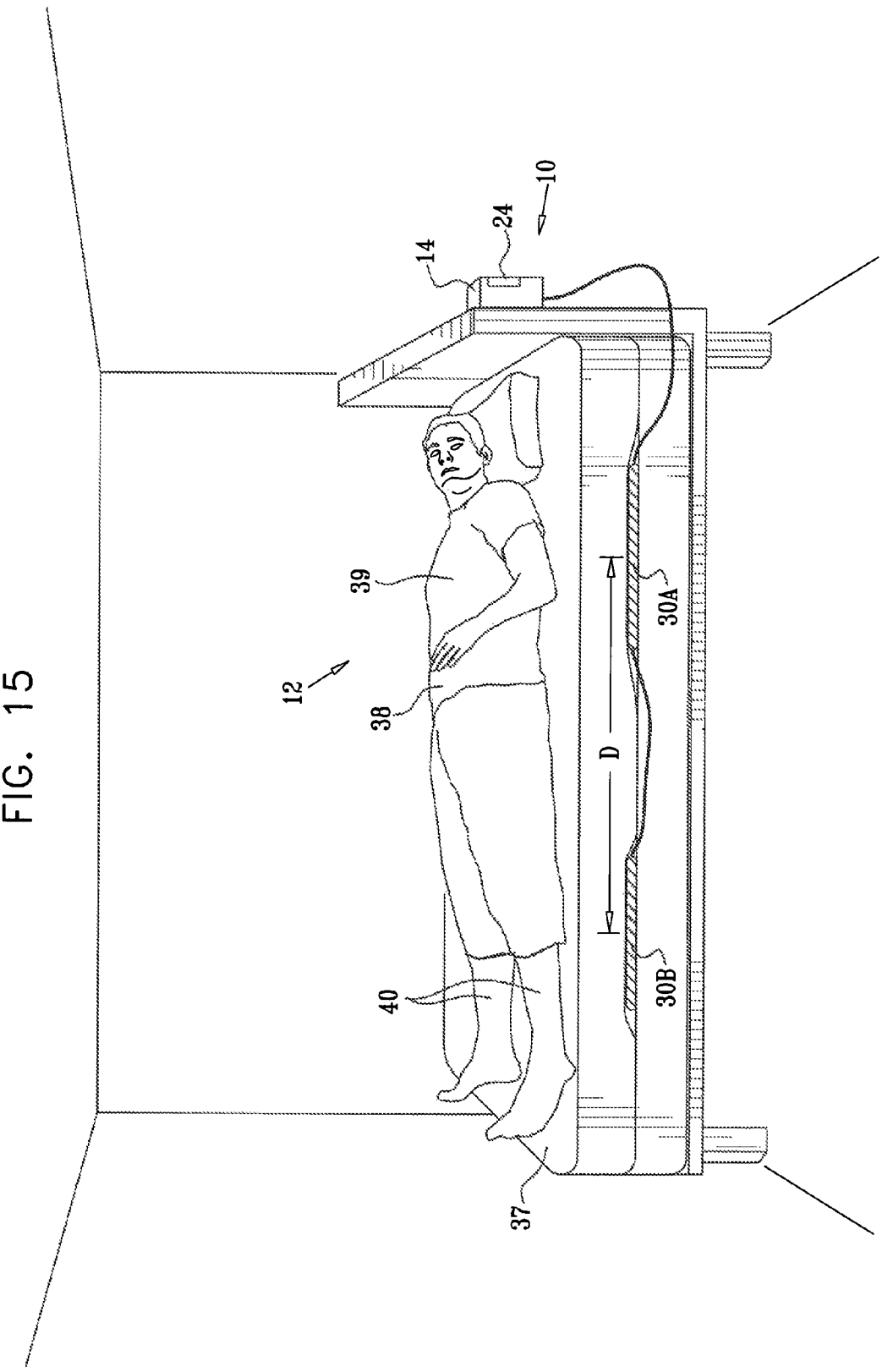

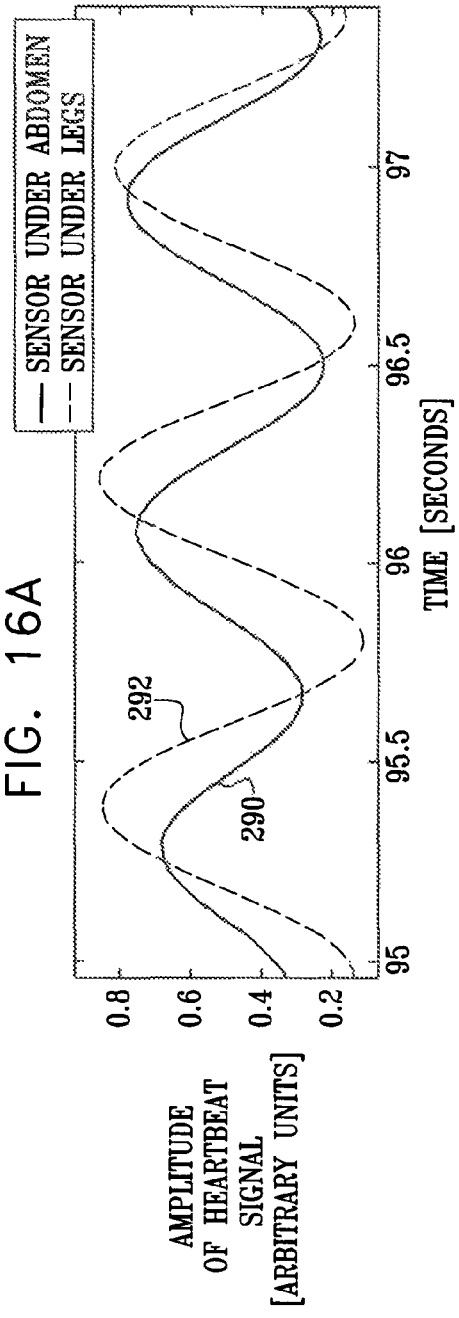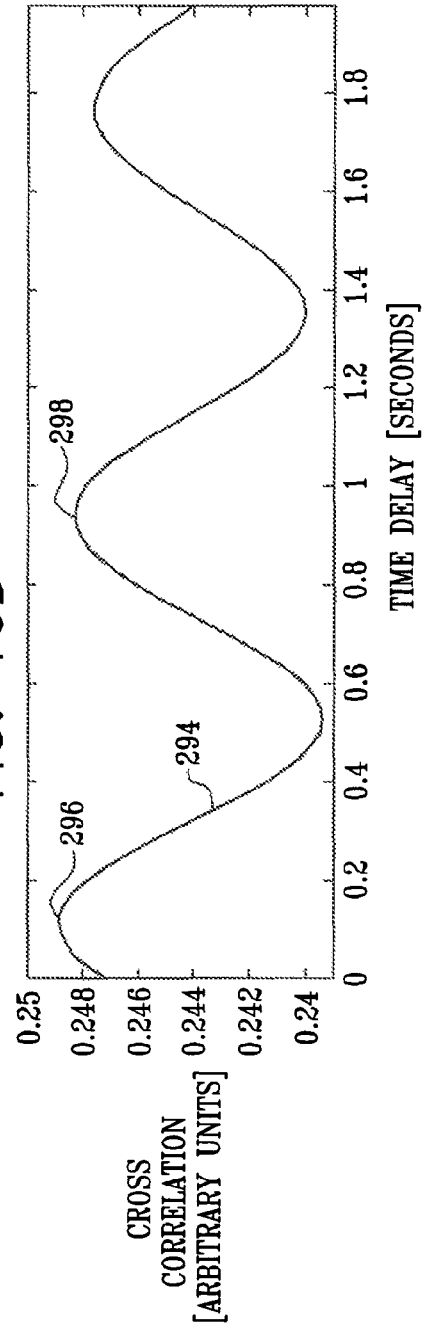

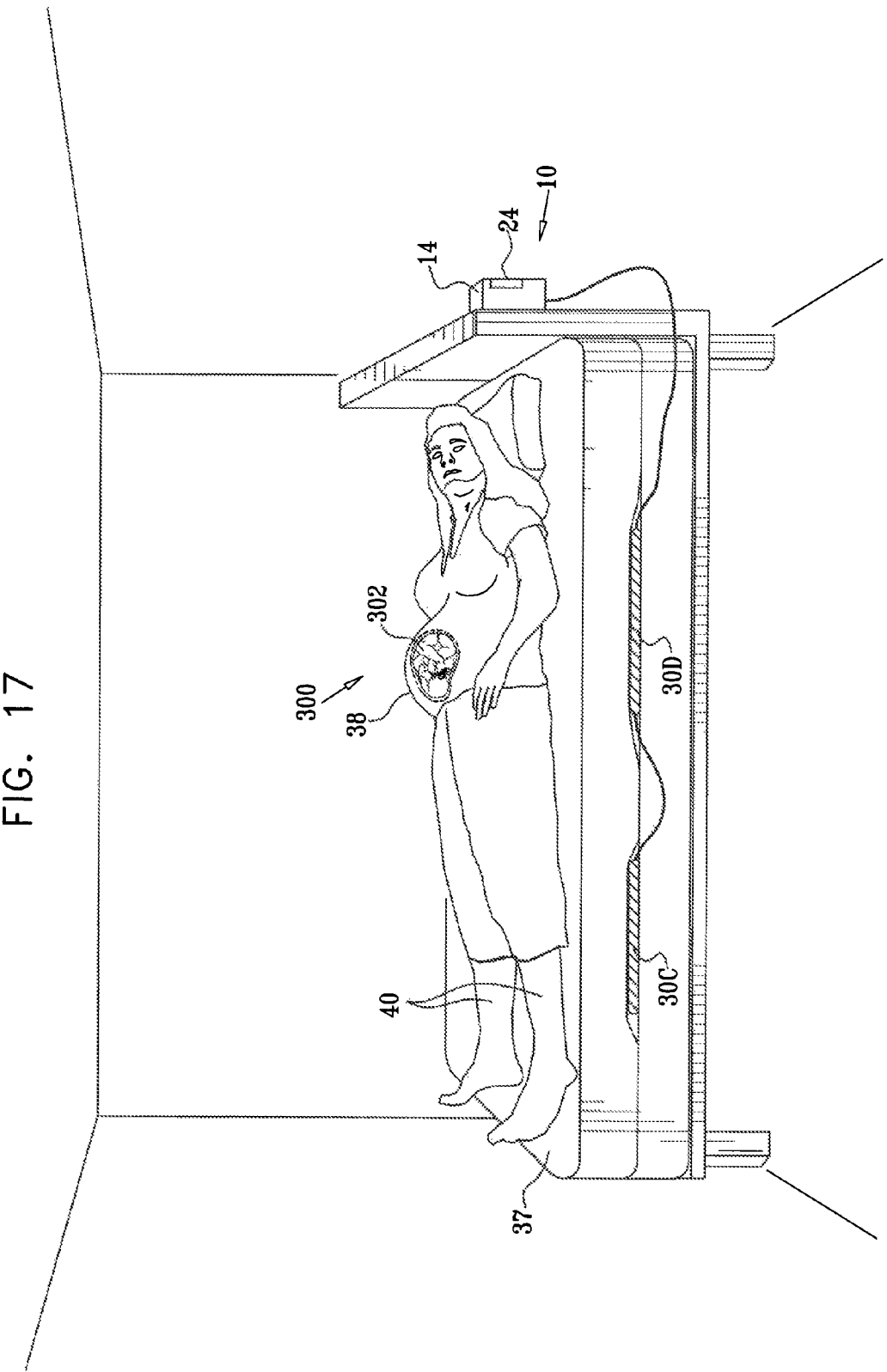

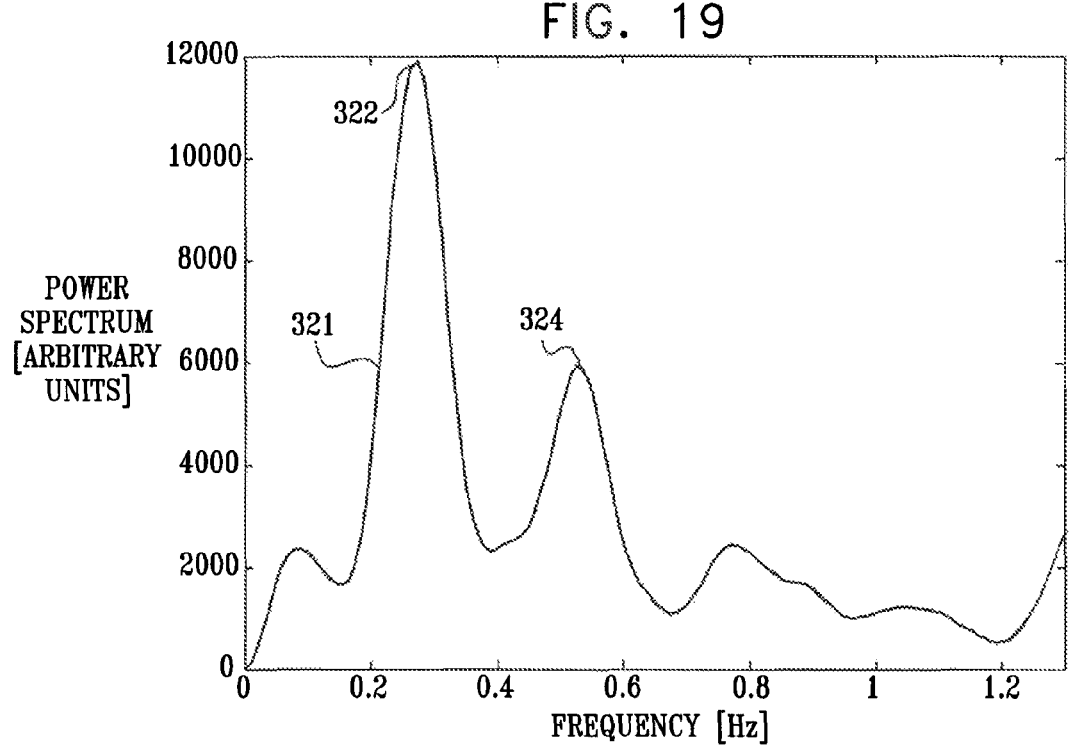
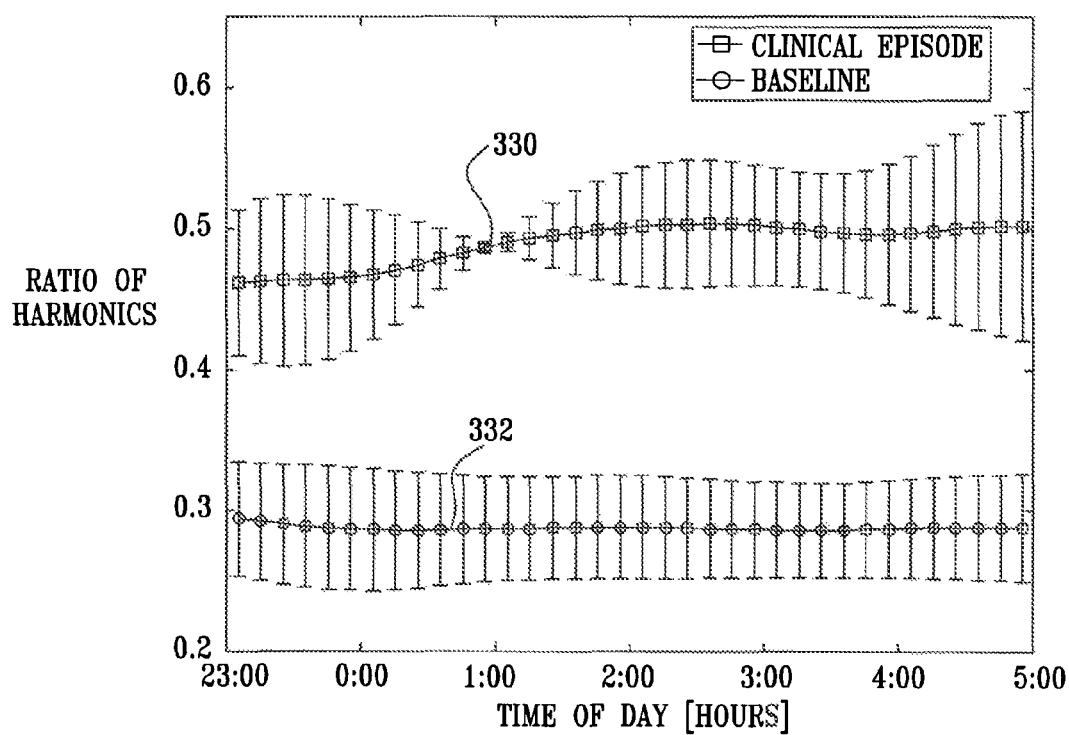

TECHNIQUES FOR PREDICTION AND MONITORING OF CLINICAL EPISODES

CROSS-REFERENCES TO RELATED APPLICATIONS

The present application is a continuation of U.S. patent application Ser. No. 11/782,750 (issued as U.S. Pat. No. 8,403,865 to Halperin), which is a continuation-in-part of:

(i) U.S. patent application Ser. No. 11/197,786 (issued as U.S. Pat. No. 7,314,451 to Halperin), filed Aug. 3, 2005, entitled, "Techniques for prediction and monitoring of clinical episodes," which claims the benefit of: (a) U.S. Provisional Patent Application 60/674,382, filed Apr. 25, 2005, entitled, "Method and apparatus for prediction and monitoring of clinical episodes," and (b) U.S. Provisional Patent Application 60/692,105, filed Jun. 21, 2005, entitled, "Method and apparatus for monitoring vital signs and predicting and monitoring clinical episodes"; and (ii) U.S. patent application Ser. No. 11/446,281 (published as US 2006/0224076 and issued as U.S. Pat. No. 8,376,954 to Lange), filed Jun. 2, 2006, entitled, "Techniques for prediction and monitoring of respiration-manifested clinical episodes," which is a continuation of U.S. patent application Ser. No. 11/048,100, filed Jan. 31, 2005, which issued as U.S. Pat. No. 7,077,810, which claims the benefit of U.S. Provisional Patent Application 60/541,779, filed Feb. 5, 2004, entitled, "Method and apparatus for prediction and monitoring of respiration manifested clinical episodes."

Each of the above-mentioned applications is incorporated herein by reference thereto

FIELD OF THE INVENTION

The present invention relates generally to predicting and monitoring abnormal physiological conditions, and specifically to methods and apparatus for predicting and monitoring abnormal physiological conditions by non-contact measurement and analysis of characteristics of physiological and/or physical parameters.

BACKGROUND OF THE INVENTION

Chronic diseases are often expressed by episodic worsening of clinical symptoms. Preventive treatment of chronic diseases reduces the overall dosage of required medication and associated side effects, and lowers mortality and morbidity. Generally, preventive treatment should be initiated or intensified as soon as the earliest clinical symptoms are detected, in order to prevent progression and worsening of the clinical episode and to stop and reverse the pathophysiological process. Therefore, the ability to accurately monitor pre-episodic indicators increases the effectiveness of preventive treatment of chronic diseases.

Many chronic diseases cause systemic changes in vital signs, such as breathing and heartbeat patterns, through a variety of physiological mechanisms. For example, common respiratory disorders, such as asthma, chronic obstructive pulmonary disease (COPD), and cystic fibrosis (CF), are direct modifiers of breathing and/or heartbeat patterns. Other chronic diseases, such as diabetes, epilepsy, and certain heart conditions (e.g., congestive heart failure (CHF)), are also known to modify cardiac and breathing activity. In the case of certain heart conditions, such modifications typically occur because of pathophysiologies related to fluid retention and general cardiovascular insufficiency. Other signs such as coughing and sleep restlessness are also known to be of importance in some clinical situations.

Many chronic diseases induce systemic effects on vital signs. For example, some chronic diseases interfere with normal breathing and cardiac processes during wakefulness and sleep, causing abnormal breathing and heartbeat patterns.

Breathing and heartbeat patterns may be modified via various direct and indirect physiological mechanisms, resulting in abnormal patterns related to the cause of modification. Some respiratory diseases, such as asthma, and some heart conditions, such as CHF, are direct breathing modifiers. Other metabolic abnormalities, such as hypoglycemia and other neurological pathologies affecting autonomic nervous system activity, are indirect breathing modifiers.

Asthma is a chronic disease with no known cure. Substantial alleviation of asthma symptoms is possible via preventive therapy, such as the use of bronchodilators and anti-inflammatory agents. Asthma management is aimed at improving the quality of life of asthma patients. Asthma management presents a serious challenge to the patient and physician, as preventive therapies require constant monitoring of lung function and corresponding adaptation of medication type and dosage. However, monitoring of lung function is not simple, and requires sophisticated instrumentation and expertise, which are generally not available in the non-clinical or home environment.

Monitoring of lung function is viewed as a major factor in determining an appropriate treatment, as well as in patient follow-up. Preferred therapies are often based on aerosol-type medications to minimize systemic side-effects. The efficacy of aerosol type therapy is highly dependent on patient compliance, which is difficult to assess and maintain, further contributing to the importance of lung-function monitoring.

Asthma episodes usually develop over a period of several days, although they may sometimes seem to appear unexpectedly. The gradual onset of the asthmatic episode provides an opportunity to start countermeasures to stop and reverse the inflammatory process. Early treatment at the pre-episode stage may reduce the clinical episode manifestation considerably, and may even prevent the transition from the pre-clinical stage to a clinical episode altogether.

Two techniques are generally used for asthma monitoring. The first technique, spirometry, evaluates lung function using a spirometer, an instrument that measures the volume of air inhaled and exhaled by the lungs. Airflow dynamics are measured during a forceful, coordinated inhalation and exhalation effort by the patient into a mouthpiece connected via a tube to the spirometer. A peak-flow meter is a simpler device that is similar to the spirometer, and is used in a similar manner. The second technique evaluates lung function by measuring nitric-oxide concentration using a dedicated nitric-oxide monitor. The patient breathes into a mouthpiece connected via a tube to the monitor.

Efficient asthma management requires daily monitoring of respiratory function, which is generally impractical, particularly in non-clinical or home environments. Peak-flow meters and nitric-oxide monitors provide a general indication of the status of lung function. However, these monitoring devices do not possess predictive value, and are used as during-episode markers. In addition, peak-flow meters and nitric-oxide monitors require active participation of the patient, which is difficult to obtain from many children and substantially impossible to obtain from infants.

CHF is a condition in which the heart is weakened and unable to circulate blood to meet the body's needs. The subsequent buildup of fluids in the legs, kidneys, and lungs characterizes the condition as congestive. The weakening may be associated with either the left, right, or both sides of the heart, with different etiologies and treatments associated with each type. In most cases, it is the left side of the heart which fails, so that it is unable to efficiently pump blood to the systemic circulation. The ensuing fluid congestion of the lungs results in changes in respiration, including alterations in rate and/or pattern, accompanied by increased difficulty in breathing and tachypnea.

Quantification of such abnormal breathing provides a basis for assessing CHF progression. For example, Cheyne-Stokes Respiration (CSR) is a breathing pattern characterized by rhythmic oscillation of tidal volume with regularly recurring periods of alternating apnea and hyperpnea. While CSR may be observed in a number of different pathologies (e.g., encephalitis, cerebral circulatory disturbances, and lesions of the bulbar center of respiration), it has also been recognized as an independent risk factor for worsening heart failure and reduced survival in patients with CHF. In CHF, CSR is associated with frequent awakening that fragments sleep, and with concomitant sympathetic activation, both of which may worsen CHF. Other abnormal breathing patterns may involve periodic breathing, prolonged expiration or inspiration, or gradual changes in respiration rate usually leading to tachypnea.

Fetal well-being is generally monitored throughout pregnancy using several sensing modalities, including ultrasonic imaging as a screening tool for genetic and developmental defects and for monitoring fetal growth, as well as fetal heartbeat monitoring using Doppler ultrasound transduction. It has been found that a healthy baby responds to activity by increased heart rate, similar to the way an adult's heart rate changes during activity and rest. Fetal heart rate typically varies between 80 and 250 heartbeats per minute, and accelerates with movement in a normal, healthy fetus. Lack of such variability has been correlated with a high incidence of fetal mortality when observed prenatally. In late stages of pregnancy, particularly in high-risk pregnancies, fetal heartbeat is commonly monitored on a regular basis to monitor fetal well-being and to identify initial signs of fetal distress, which usually result in active initiation of an emergency delivery. Current solutions to monitor fetal well-being are generally not suitable for home environments.

Ballistocardiography is the measurement of the recoil movements of the body which result from motion of the heart and blood in the circulatory system. Transducers are available which are able to detect minute movements of the body produced by the acceleration of the blood as it moves in the circulatory system. For example, U.S. Pat. No. 4,657,025 to Orlando, which is incorporated herein by reference, describes a device for sensing heart and breathing rates in a single transducer. The transducer is an electromagnetic sensor constructed to enhance sensitivity in the vertical direction of vibration produced on a conventional bed by the action of patient's heartbeat and breathing functions, and is described as achieving sufficient sensitivity with no physical coupling between the patient resting in bed and the sensor placed on the bed away from the patient.

Pulsus paradoxus is a physical sign present in a variety of cardiac and extra-cardiac conditions, which is of valuable diagnostic and prognostic significance. Pulsus paradoxus is generally defined as a fall in systolic blood pressure of over 10 mmHg during inspiration. Pulsus paradoxus has been associated with the following conditions: cardiac tamponade, pericardial effusion, constrictive pericarditis, restrictive cardiomyopathy, pulmonary embolism, acute myocardial infarction, cardiogenic shock, bronchial asthma, tension pneumothorax, anaphylactic shock, volvulus of the stomach, diaphragmatic hernia, superior vena cava obstruction. In bronchial asthma, pulsus paradoxus is of significance because it has often been associated with mild obstructions and can therefore serve as an early warning sign. Pulsus paradoxus is generally difficult to assess in children, particularly in an emergency room (see, for example, Brenner B E et al., "The clinical presentation of acute asthma in adults and children," In Brenner, B E, ed. *Emergency Asthma* (New York: Marcel Dekker, 1999:201-232)).

U.S. Pat. No. 6,468,234 to Van der Loos et al., which is incorporated herein by reference, describes apparatus for measuring sleep quality that utilizes sensors incorporated in a sheet which is laid on top of a conventional mattress on which the subject sleeps. The sensors can collect information such as the subject's position, temperature, sound/vibration/movement, and optionally other physical properties. The apparatus comprises one or more layers of arrays of integrated sensors, which can be incorporated in layer pads, which is then placed on a conventional mattress; one or more controllers coupled with the arrays of integrated sensors in each layer pad for the purpose of acquiring data from the sensors; real-time analysis software for analyzing data acquired by the controller from the array of integrated sensors; interface software for collecting user lifestyle data; lifestyle correlation software for correlating the lifestyle data with the data acquired by said array of sensors; and one or more active components to improve sleep quality based on the data acquired through the sensors and the lifestyle data. The array of sensors provide one or more of the following data: position, temperature, sound, vibration, and movement data.

U.S. Pat. No. 6,547,743 to Brydon, which is incorporated herein by reference, describes a movement-sensitive mattress having a plurality of independent, like movement sensors for measuring movement at different locations on the mattress to generate a plurality of independent movement signals. The signals are processed to derive respiratory variables including rate, phase, maximum effort or heart rate. Such variables can be combined to derive one or more diagnostic variables including apnea and labored breathing classifications.

U.S. Pat. No. 6,840,907 to Brydon, which is incorporated herein by reference, describes a respiratory analysis system for monitoring a respiratory variable of a patient. The system comprises a sensor array for accommodating a patient to be in contact therewith and a processing means. The array has a plurality of independent like sensors for measuring respiratory movement at different locations on the patient to generate a set of independent respiratory movement signals. The processing means receives and processes the movement signals to derive a classification of individual breaths using, for each breath, the respective phase and/or amplitude of each movement sensor signal within the set for that breath.

U.S. Pat. No. 6,485,441 to Woodward, which is incorporated herein by reference, describes a mattress device including sensors placed in correspondence with a mattress core layer and a mattress top layer of the mattress device, in order to monitor a patient's sleep behavior. The mattress core and top layers provide a static position transmission characteristic and a dynamic impulse transmission characteristic enabling the sensors to recognize body imprint position and body impulses induced by the sleeping patient with a broad bandwidth.

U.S. Pat. No. 5,448,996 to Bellin et al., which is incorporated herein by reference, describes a patient monitor sheet device for measuring respiration, heart beat, and body position. Sensors are located in a bed sheet with which a subject comes in contact. One sensor produces a signal corresponding to respiratory induced, pulmonary motion, and myocardial pumping sounds. A second sensor produces a signal corresponding to changes in body position. A processor amplifies and filters the induced signals to produce an output correlated to respiration rate, heart beat rate, and changes in body position.

U.S. Pat. No. 6,517,497 to Rymut et al., which is incorporated herein by reference, describes techniques for monitoring and/or quantitatively measuring a patient's respiration using a flexible piezoelectric film sensor. The apparatus includes a piezoelectric film which converts acoustical waves generated by the patient's respiration into electrical signals. The piezoelectric film sensor can be used to monitor the respiration of a patient by correlating the sound generated in the patient's airway with respiratory activity. The data generated by the sensor may be further analyzed by a patient monitor to diagnose respiratory conditions.

U.S. Pat. No. 5,002,060 to Nedivi, which is incorporated herein by reference, describes a monitoring system adapted to simultaneously monitor cardiac and respiratory rates and characteristics and substantial changes in temperature of a subject. The system uses sensors which are passive and non-invasive, and located remotely from (i.e., completely off of) the subject. The system is adapted to distinguish the desired signals from undesired environmental noise. The signals are processed in order to provide an alarm accompanied with displayed indication of any irregularities in the cardiac and respiratory rates and characteristics, and substantial changes in temperature. The system also includes a device to transmit said displayed data and alarm to a remote location as desired.

U.S. Pat. No. 6,450,957 to Yoshimi et al., which is incorporated herein by reference, describes a respiration monitoring system that monitors the state of disorder of the respiratory system of a sleeping patient based on the detection of respiratory body movement, without the need to put sensors directly on the patient's body. The system includes weight sensors that produce weight signals attributable to the patient's respiratory body movement. From weight signals having a frequency band of respiration, a respiratory body movement signal is produced. The fall of blood oxygen saturation which occurs during obstructive apnea of the sleeping patient is determined based on the variation pattern of the amplitude of respiratory body movement signal. The occurrence and frequency of the fall of blood oxygen saturation are displayed on a display unit.

U.S. Pat. No. 5,853,005 to Scanlon, which is incorporated herein by reference, describes a transducer in communication with fluid in a pad. The pad is held in close contact against a sound or movement source, and monitors acoustic signals transferred into the fluid. The signal pattern is monitored aurally and/or compared to predetermined reference patterns, and optional control and stimulation means can be activated in response to the comparison results. The sensed acoustic signal can be transmitted to a remote receiver or processed locally. Typically, the acoustic signal is representative of the heartbeat or breathing of a living organism. The monitoring system may be applied to diverse situations including SIDS, apnea, home baby monitoring, medical transport devices, blood pressure cuffs, seats, combat casualty care and handheld devices. An embodiment is described in which the system is attached to home or institution mattresses for health monitoring, recovery, research, or presence detection.

U.S. Pat. No. 6,666,830 to Lehrman et al., which is incorporated herein by reference, describes a system for detecting the onset of an obstructive sleep apnea event before the obstructive sleep apnea event fully develops, and before the cessation of breathing occurs. The system includes one or more microphones capable of detecting breathing sounds within an airway of a person. The microphones generate signals representative of the breathing sounds, and send the signals to a controller. The controller identifies at least one signal pattern that is associated with a breathing pattern of the person that occurs at the onset of an obstructive sleep apnea event. The controller may also identify at least one signal pattern that is associated with a partially-occluded breathing pattern of the person. The controller identifies the signal patterns by using digital signal processing techniques to analyze the signals representative of breathing sounds. The method involves detecting breathing sounds within an airway of a person, generating signals representative of the breathing sounds, and identifying at least one signal pattern that is associated with a breathing pattern of the person that occurs at the onset of an obstructive sleep apnea event.

U.S. Pat. No. 6,790,183 to Murphy, which is incorporated herein by reference, describes a lung sound diagnostic system for use in collecting, organizing and analyzing lung sounds associated with the inspiration(s) and expiration(s) of a patient. The system includes a plurality of transducers that may be placed at various sites around the patient's chest. The microphones are coupled to signal processing circuitry and A/D converters which digitize the data and preferably provides the digital data to a computer station. The system may also include application programs for detecting and classifying abnormal sounds. The resulting information may be displayed in a variety of formats to facilitate diagnosis. Additionally, the system may include an analysis program for comparing selected criteria corresponding to the detected abnormal sounds with predefined thresholds in order to provide a likely diagnosis. Also described are a system and method for differentiating between the crackles produced by an patient with interstitial pulmonary fibrosis (IPF) from the crackles produced by a CHF patient.

U.S. Pat. No. 6,168,568 to Gavriely, which is incorporated herein by reference, describes a phonopneumograph system for analyzing breath sounds. The system includes a plurality of breath-related sensors placed around the respiratory system of a patient for measuring breath-related activity, and a breath analyzer. The breath analyzer matches the breath sound data produced by the breath-related sensors to a plurality of breath sound templates, each of which parameterizes one type of breath sound, and determines the presence of regular and/or adventitious breath sounds only when the breath sound data matches, within predetermined goodness of fit criteria, one or more of the breath sound templates.

U.S. Pat. No. 6,261,238 to Gavriely, which is incorporated herein by reference, describes a method for analyzing breath sounds produced by a respiratory system. The method includes measuring breath sounds produced by the respiratory system; tentatively identifying a signal as being caused by a breath sound of a given type if it meets a first criterion characteristic of the breath sound of the given type; and confirming the identification if a tentatively identified signal meets a second criterion characteristic of the breath sound of the given type.

U.S. Pat. No. 5,738,102 to Lemelson, which is incorporated herein by reference, describes a system for monitoring and computer analyzing select physiological variables of a patient in real time in order to alert medical personnel to the need for medical treatment or automatically administering such treatment under computer control. Such physiological variables monitored by the system may include lung sounds, respiratory rate and rhythm, heart rate and rhythm, heart sounds, and body temperature. Coded signals relating to the physiological variables are produced and compared with reference versions of same by a decision computer in order to evaluate the patient's condition. If the evaluation indicates medical treatment is needed, the decision computer activates a local and/or a remote alarm to alert medical personnel and/or activates one or more actuators for administering a medical treatment such as the injection or infusion of a drug. Examples of body sounds which may be detected are respiratory sounds and heart sounds. In the case of the former, the computer produces coded signals representing the rate and rhythm of breathing derived from the respiratory sounds. The system is described as being able to detect abnormal breathing patterns such as apnea, tachypnea, hyperpnea (e.g., Kussmaul breathing associated with metabolic acidosis), bradypnea, Cheyne-Stokes breathing, ataxic breathing, and obstructive breathing. Coded signals may also be generated from the respiratory sounds which indicate the presence of added lung sounds such as rales associated with pneumonia and pulmonary edema, wheezes associated with obstructive lung disease, and pleural rubs due to inflammation of the pleural membranes.

US Patent Application Publication 2005/0085866, issued as U.S. Pat. No. 8,255,056, and PCT Publication WO 05/037366 to Tehrani, which are incorporated herein by reference, describe methods for sensing breathing disorders, irregularities, or insufficiencies. One aspect includes sensing a precursor to an onset of a breathing disorder or episode of a breathing disorder and responding to sensing the precursor. Another aspect includes responding to treat the breathing disorder before manifestation of the disorder. Another aspect includes identifying a likelihood of a breathing disorder and responding using the likelihood and other information indicating onset or occurrence of a breathing disorder. In one embodiment, the breathing disorder event is apnea or the onset of an episode of apnea. In another embodiment, the breathing disorder event is an episode of Cheyne-Stokes respiration.

PCT Publication WO 05/037077 to Tehrani, which is incorporated herein by reference, describes techniques for detecting and managing heart failure patient symptoms. Respiration and/or cardiac parameters are sensed to determine the status of a patient's condition. These symptoms may be classified for appropriate patient disease management. A patient's activity level may be monitored in conjunction with respiration and/or cardiac parameters to provide additional patient status information. Pulmonary edema is one condition that may be determined to exist when a respiration parameter is out of range for a given sensed activity level.

U.S. Pat. No. 6,599,251 to Chen et al., which is incorporated herein by reference, describes non-invasive techniques for monitoring the blood pressure of a subject. A pulse signal is detected at both a first and second location on the subject's body. The elapsed time between the arrival of corresponding points of the pulse signal at the first and second locations is determined. Blood pressure is related to the elapsed time by mathematical relationships.

U.S. Pat. No. 6,290,654 to Karakasoglu, U.S. Pat. No. 6,375,623 to Gavriely, U.S. Pat. No. 6,223,064 to Lynn et al., and US Patent Application Publication 2004/0225226, issued as U.S. Pat. No. 7,819,823, to Lehrman et al., which are incorporated herein by reference, describe various techniques for detecting and/or analyzing episodes of sleep apnea.

US Patent Application Publication 2004/0133079 to Mazar et al., which is incorporated herein by reference, describes techniques for predicting patient health and patient relative well-being within a patient management system. An embodiment utilizes an implantable medical device comprising an analysis component and a sensing component further comprising a three-dimensional accelerometer, a transthoracic impedance sensor, a cardio-activity sensor, an oxygen saturation sensor, and a blood glucose sensor. One analysis described is detecting changes in transthoracic impedance variation patterns that are indicative of the early occurrence of a new disease state (such as Chronic Obstructive Pulmonary Disease), the onset of an illness (such as asthma), or the progression of a disease (such as DC impedance indicating lung fluid accumulation which corresponds to the progression of heart failure).

U.S. Pat. No. 5,522,382 to Sullivan et al., which is incorporated herein by reference, describes an air flow device for treating upper airway disordered breathing. The airflow device has means for delivering variable pressure levels of breathable air to a patient's respiratory system, and means for controlling the time during which the delivered pressurized air rises from an initial pressure level to a higher operating pressure level.

PCT Publication WO 05/028029 to Stahmann et al., which is incorporated herein by reference, describes techniques for monitoring, diagnosing, and/or treating a patient. The techniques include detecting or predicting events, such as disordered breathing (apnea, hypopnea, tachypnea), coughing and/or breathing irregularities associated with pulmonary diseases and disorders such as asthma, pulmonary edema, chronic obstructive pulmonary disease, and/or pleural effusion. A pre-apnea or pre-hypopnea condition may be detected by analyzing the patient's respiration patterns. Respiration cycles just prior to a disordered breathing event, e.g., an apnea or hypopnea event, may exhibit a characteristic pattern. For example, an apnea event for many patients is preceded by a period of hyperventilation with a number of rapid, deep breaths. The pattern of hyperventilation may be detected by analyzing patient's transthoracic impedance signal to determine respiration rate and tidal volume.

US Patent Application Publication 2005/0043644, issued as U.S. Pat. No. 7,396,333, to Stahmann et al., which is incorporated herein by reference, describes an approach for predicting disordered breathing by detecting one or more conditions associated with disordered breathing. The detected conditions are compared to disordered breathing prediction criteria. A prediction of disordered breathing is performed based on the comparison of the detected conditions to the prediction criteria. At least one of comparing the detected conditions to the prediction criteria and predicting disordered breathing is performed at least in part using an implantable device.

U.S. Provisional Patent Application 60/504,229 to Stahmann et al., which is incorporated herein by reference, describes techniques for coordinated functioning of a cardiac device and a respiratory device. The cardiac and the respiratory devices operate cooperatively to provide one or more of patient monitoring, diagnosis, and therapy. The system may include a processing system external and coupled to the cardiac and respiratory devices. The processing system may operate cooperatively with the cardiac and respiratory devices to coordinate one or more medical procedures.

U.S. Pat. No. 6,047,203 to Sackner et al., which is incorporated herein by reference, describes a non-invasive physiological signs monitoring device, including a shirt having electrocardiogram electrodes and various inductive plethysmographic sensors. When an adverse condition or other preprogrammed condition occurs, a message is communicated to the patient and/or to a remote receiving unit for monitoring by a health care professional or other machine. For example, if a patient has asthma, pertinent signs such as respiratory drive/ventilation (peak inspiratory flow/ventilation and/or peak inspiratory acceleration/ventilation) may be monitored as non-invasive signs of increasing bronchospasm above a predetermined threshold. This measure is utilized to provide directions to the monitored patient, such as, for example, "You have signs of bronchospasm; please take your aerosol medication now!" If aerosol medication is taken correctly and the proper breathholding pattern is observed, then the output device may state, "Aerosol taken, good!"

US Patent Application Publication 2003/0135127, issued as U.S. Pat. No. 7,670,295, to Sackner et al., which is incorporated herein by reference, describes physiological monitoring apparel worn by a monitored individual, the apparel having attached sensors for monitoring parameters reflecting pulmonary function, cardiac function, or the function of other organ systems. In an embodiment, an alarm is generated based on a trend progressing over one to a few hours. For example, in a congestive heart failure patient, over two hours of increasing respiratory rate, perhaps coupled with sustained cardiac rate changes, may signal early the onset of pulmonary edema.

U.S. Pat. No. 6,015,388 to Sackner et al., which is incorporated herein by reference, describes a method for measuring respiratory drive, including determining a peak inspiratory flow and a peak inspiratory acceleration from a breath waveform derived from rib cage motion and abdominal motion using a plethysmograph or other external respiratory measuring device. The respiratory drive is described as being ascertainable even during complete blockage of the respiratory system. The peak inspiratory drive is used to initiate inspiration in a mechanical ventilator and for determining an index describing a shape of the waveform for controlling a continuous positive air pressure (CPAP) device.

US Patent Application Publication 2004/0111040, issued as U.S. Pat. No. 7,252,640, to Ni et al., which is incorporated herein by reference, describes techniques for detecting disordered breathing, including sensing one or more signals associated with disordered breathing indicative of sleep-disordered breathing while the patient is sleeping. Sleep-disordered breathing is detected using the sensed signals associated with disordered breathing. The sensed signals associated with disordered breathing may also be used to acquire a respiration pattern of one or more respiration cycles. Characteristics of the respiration pattern are determined, and the respiration pattern is classified as a disordered breathing episode based on the characteristics of the respiration pattern. One or more processes involved in the detection of disordered breathing are performed using an implantable device.

US Patent Application Publication 2005/0061315, issued as U.S. Pat. No. 7,469,697, to Lee et al., which is incorporated herein by reference, describes techniques for monitoring one or more patient conditions using a monitoring device that is fully or partially implantable. Feedback information is developed based on the monitored conditions and is provided to a device delivering therapy to treat sleep disordered breathing. Components of the monitoring device are disposed within an implantable housing that is separate from the housing of the therapy device. The therapy device may comprise a housing that is implantable or patient-external. The feedback information may be used to adjust the sleep disordered breathing therapy.

US Patent Application Publication 2003/0004423, issued as U.S. Pat. No. 7,806,831, to Lavie et al., which is incorporated herein by reference, describes techniques for monitoring the sleep state condition of an individual using an external probe applied to a peripheral body location, such as the individual's finger or toe, for detecting changes in the peripheral vascular bed volume of the individual. Such information is described as being useful for diagnosing and/or treating a number of sleep disorders, as well as other conditions, such as impotence, diabetes, and various disorders in children. For example, Cheyne-Stokes breathing may be detected using a finger-probe, or nocturnal asthmatic activity may be recognized.

U.S. Pat. No. 6,512,949 to Combs et al., which is incorporated herein by reference, describes an impedance monitor for discerning edema through evaluation of respiratory rate.

U.S. Pat. No. 6,454,719 to Greenhut, which is incorporated herein by reference, describes techniques for determining the cardiac condition of a patient by a cardiac monitor apparatus using a respiration parameter such as a current respiration signal or a respiration rate. The variability of the respiration parameter is used to generate a signal indicative of the current heart failure status of the patient, and, more particularly, whether the patient's condition has improved, worsened, or remained unchanged over a predetermined time period. The circuitry for detecting the respiration parameter may be implanted in the patient, for example as part of a pacemaker, while at least some of the analyzing circuitry may be external and remote from the patient. Alternatively the whole device may be implantable.

U.S. Pat. No. 6,600,949 to Turcott, which is incorporated herein by reference, describes a method for monitoring the condition of a heart failure patient using respiration patterns. An implantable or other ambulatory monitor senses the patient's respiratory patterns to identify the presence of periodic breathing or Cheyne-Stokes respiration. In a first embodiment, mechanical changes of the thorax due to breathing are detected and this data is used to recognize hyperventilation and apnea or hypoventilation. In a second embodiment, Cheyne-Stokes respiration is recognized by detecting changes in blood or tissue pH or CO2 concentration and partial pressure. In another embodiment, changes in pulse amplitude associated with Cheyne-Stokes respiration are detected. Alternating loss and return of respiration-induced amplitude modulation or pulse-interval variation may also be used to identify the presence of Cheyne-Stokes respiration. In yet another embodiment, modulation of the average heart rate over time is monitored and its absence is used as an indicator of Cheyne-Stokes respiration. This information may be used to warn the patient or healthcare provider of changes in the patient's condition warranting attention.

U.S. Pat. No. 6,527,729 to Turcott, which is incorporated herein by reference, describes a method for monitoring the progression of disease of a heart failure patient. An implantable or other ambulatory monitor senses acoustic signals including heart and lung sounds within the patient. Significant changes in the energy content of either the heart or lung sounds is indicative of a heart failure exacerbation. This information may be used to warn the patient or healthcare providers of changes in the patient's condition warranting attention.

U.S. Pat. No. 6,641,542 to Cho et al., which is incorporated herein by reference, describes apparatus for detecting and treating sleep respiratory events, including a plurality of sensors gathering physiological data related to sleep respiratory events. A processor extracts an average cycle length and a frequency of at least one of Cheyne-Stokes respiration and periodic breathing based upon the physiological data, and determines whether therapy is required based on the average cycle length and the frequency.

U.S. Pat. No. 6,830,548 to Bonnet et al., which is incorporated herein by reference, describes apparatus for diagnosing a patient respiratory profile. The apparatus measures respiratory activity and delivers a signal representative of the periodicity and amplitude of the successive respiratory cycles of the patient, in particular, a minute ventilation signal. The device analyzes the signal and discriminates between various types of respiratory profiles, in particular Cheyne-Stokes breathing.

U.S. Pat. No. 6,589,188 to Street et al., which is incorporated herein by reference, describes a method for detecting and monitoring periodic breathing to provide an indication of changes in the hemodynamic status of a heart failure patient. The method includes monitoring at least one of four independent physiologic parameters: respiratory tidal volume, respiratory rate (B-B interval), arterial oxygen saturation, and heart rate (R-R interval). These parameters may be analyzed by performing power spectral analysis or thresholding/binning. Each analysis method can be applied to each measure or combination thereof. In a preferred embodiment, the patient is monitored when at rest or asleep to prevent interference from activity-related respiratory variations.

U.S. Pat. No. 5,902,250 to Verner et al., which is incorporated herein by reference, describes a method for determining the sleep state of a patient, including monitoring heart rate variability of the patient and determining sleep state based on the heart rate variability. Also described is a method for determining respiratory pattern, including monitoring heart rate variability by receiving heart beat signals and determining respiratory pattern from the strength of the signals. A home-based, wearable, self-contained system determines sleep-state and respiratory pattern, and assesses cardiorespiratory risk of a patient based on the frequency of eyelid movements, the frequency of head movements, and heart rate variability of the patient. The system includes an automatic alarm system for awakening a patient should a dangerous breathing or heart-related event occur. The system is described as being particularly useful for patients in heart failure, particularly those with an existing respiratory disorder, a combination which may provoke Cheyne-Stokes respiration.

U.S. Pat. No. 5,590,650 to Genova, which is incorporated herein by reference, describes apparatus for monitoring physiological vital signs of a human body without physically contacting the body. The apparatus includes a sensor for transforming a movement and/or acoustical wave produced by the body into an electrical signal, and a signal processor coupled to the sensor for receiving the electrical signal from the sensor, and for processing the electrical signal adaptively using wavelet correlator analysis. Typically, the apparatus is used to monitor heart rate, respiration rate and related sounds, digestive system sounds, as well as other physiological vital signs.

U.S. Pat. No. 6,893,404 to Ragnarsdottir, which is incorporated herein by reference, describes techniques for measuring breathing movements and determining breathing patterns, by measuring the simultaneous movement of a plurality of points of a human subject, such that a breathing pattern may be determined based on data obtained in a single acquisition.

U.S. Pat. No. 6,752,766 to Kowallik et al., which is incorporated herein by reference, describes a method for identifying a minimum of one breathing parameter which is characteristic of the breathing status of a sleeping individual. The method comprises: measuring the derivative trend with respect to time of a minimum of one variable of state of the cardiovascular system of the individual, which variable recurrently changes with the respiration; determining breath-to-breath intervals, each of which represents the duration of one breath, from the results of the measurement; and identifying the breathing parameter which is defined by the variability of the breath-to-breath intervals in phases of unobstructed breathing and/or statistical variables derived therefrom.

U.S. Pat. No. 6,368,287 to Hadas, which is incorporated herein by reference, describes a device, described as suitable for use without professional medical supervision, for screening for sleep apnea. All elements of the device are housed in a small, flexible, plastic housing which is placed on the user's philtrum. A thermistor acquires data describing the respiratory pattern. A processor analyzes the respiratory pattern in real time and outputs a study result, describing the occurrence of any episodes of apnea.

U.S. Pat. No. 6,375,621 to Sullivan, which is incorporated herein by reference, describes apparatus that monitors the acoustic and electromechanical signals of a patient, and calculates an energy spectrum periodogram or histogram using time series analysis techniques. The patient lies down on a large piezoelectric film (a few microns thick) that has the capability of measuring signals from very high to very low frequencies. The heart and respiration rates as well as obstructive apnea can be observed, detected and measured from the spectral peaks in the resulting energy spectrum. An alarm calls for assistance in the event of an apnea, including obstructive apnea, or a Sudden Infant Death Syndrome (SIDS) episode.

U.S. Pat. No. 5,964,720 to Pelz, which is incorporated herein by reference, describes a system for the monitoring of a patient's physiological condition, including a measuring device for measuring the mechanical activity of a patient's body, including a module for detecting mechanical vibrations and transmitting them to a sensing element for converting the mechanical movements into electric signals. Also described is a device for transmitting the electric signals for processing the electric signals and separating from them cardiac, respiration, and body movement signals. Further described is a device for measuring a pulse wave propagation rate. Still further described is a device for determining characteristics and derived parameters of cardiac and respiratory cycles, as well as for storing and displaying the data. Additionally described is a comparator for comparing parameters of data with predetermined parameters, and a device for actuating an alarm signal when signals of the data exceed a preset range.

U.S. Pat. No. 6,239,706 to Yoshiike et al., which is incorporated herein by reference, describes an in-bed state detection system including a load detection section for detecting a load applied to a bed and providing a corresponding load signal; a determination section for determining an in-bed state based on the load signal; and a transmission section for transmitting a result of the determination.

U.S. Pat. No. 5,879,313 to Raviv et al., which is incorporated herein by reference, describes a method for classifying respiratory sounds, including selecting a first set of respiratory sounds, manually determining a classification content of the first set of respiratory events, and extrapolating the classification content of the first set of respiratory events to an at least second set of respiratory events.

U.S. Pat. No. 6,064,910 to Andersson et al., which is incorporated herein by reference, describes a device for determining the respiration rate and/or respiration depth of a patient, including a sensor for sensing heart sounds, and an analyzer for analyzing the variation of the amplitude of the sensed heart sounds to determine the respiration rate and/or respiration depth from this amplitude variation. Apparatus for monitoring the respiration of a patient includes such a device and the analyzer is arranged to determine an anomaly in the amplitude variation of the sensed heart sounds as an indication of a respiration anomaly.

U.S. Pat. No. 6,126,595 to Amano et al., which is incorporated herein by reference, describes a device for diagnosing physiological state based on blood pulse waves detected in the body. The device includes a blood pulse wave detector and stroke-volume-per-beat measurer, which respectively detect blood pulse wave and stroke volume in the body; a blood pulse wave extraction memory, which extracts characteristic information from the detected blood pulse wave; and an output portion which outputs an alarm.

U.S. Pat. No. 5,520,176 to Cohen, which is incorporated herein by reference, describes a sleep analysis system for analyzing a sleep episode of a subject based on measured values of a plurality of parameters characterizing that subject. Portions of the measured parameter signals are classified as significant events, and the significant events are segregated based on parameter signal criteria and time correlation as a basis for the analysis.

U.S. Pat. No. 5,944,680 to Christopherson et al., which is incorporated herein by reference, describes a method of predicting critical points in patient respiration, including monitoring at least one characteristic of a respiratory effort waveform of a patient to detect a respiratory event.

U.S. Pat. No. 6,033,370 to Reinbold et al., which is incorporated herein by reference, describes a capacitive force sensor which has a plurality of layers forming a force sensing detector, the detector providing a signal in response to pressure; a feedback element that provides feedback in response to the signal from the force sensing detector; and a housing for encompassing the force sensing detector and the feedback element.

U.S. Pat. No. 6,135,970 to Kadhiresan et al., which is incorporated herein by reference, describes techniques for assessing the status of well-being of patients being treated for CHF using cardiac pacing as a therapy. By sampling the output from an activity sensor or the like, and by noting the frequency with which the averaged rectified sensor output exceeds a preset threshold following changes in the pacing mode, the efficacy of the new mode compared to the previous one can be evaluated.

U.S. Pat. No. 6,751,498 to Greenberg et al., which is incorporated herein by reference, describes techniques for fetal heart and maternal heart and uterine monitoring. The techniques acquire biopotential waveforms indicative of the mother's heart beat from sensors located at or near the mother's chest, and waveforms indicative of the combined maternal and fetal heart beats from abdominal sensors located on the mother's abdomen, lower back, or both. The signals from the abdominal sensors are divided into a plurality of channels. An adaptive signal processing filter (ASPF) algorithm or other suitable algorithm is then used to cancel the estimated maternal waveform from each channel derived from the abdominal sensors. The system then selects from the resulting waveforms at least one waveform to serve as the reference fetal waveform. The reference waveform is then processed against the other abdominal waveforms preferably using the ASPF algorithm again to form an enhanced fetal signal that is a representation of the fetus's biopotential electrocardiogram (ECG). The fetus's biopotential ECG is subsequently be used to measure fetal heart rate and other biophysical profile parameters. Surface electromyogram (EMG) signals are described as allowing for concurrent monitoring of uterine contractions and afford improved cancellation of motion artifacts.

US Patent Application Publication 2004/0210155, issued as U.S. Pat. No. 7,428,468, to Takemura et al., which is incorporated herein by reference, describes a monitoring device for detecting conditions of a sleeping person. The device comprises multiple independent distance sensors installed facing different positions in a monitored target area to be monitored, for measuring a distance to a monitored target; a calculating unit for calculating changes over time in the outputs of the distance sensors; and a detection processor for detecting changes in shape of the monitored target based on the calculated changes over time in one or multiple distance sensor among the multiple distance sensors.

The following patents and patent application publication, all of which are incorporated herein by reference, may also be of interest:

U.S. Pat. No. 4,657,026 to Tagg;
U.S. Pat. No. 5,235,989 to Zomer;
U.S. Pat. No. 5,957,861 to Combs;
U.S. Pat. No. 6,383,142 to Gavriely;
U.S. Pat. No. 6,436,057 to Goldsmith et al.; and
U.S. Pat. No. 6,856,141 to Ariay.

An article by Shochat M et al., entitled, "PedemaTOR: Innovative method for detecting pulmonary edema at the pre-clinical stage," undated, available at http://www.isramed-.info/rsmm_rabinovich/pedemator.htm, which is incorporated herein by reference, describes an impedance monitor for pre-clinical detection of pulmonary edema. The impedance monitor measures "internal thoracic impedance," which is roughly equal to lung impedance, by automatically calculating skin-electrode impedance and subtracting it from the measured transthoracic impedance.

It has been suggested that bio-modification of breathing and heart rate might prove beneficial for chronic conditions such as asthma and CHF, as well as for other conditions such as stress (see, for example, U.S. Pat. Nos. 5,076,281, 5,800, 337, and 6,090,037 to Gavish, U.S. Pat. No. 6,662,032 to Gavish et al., and US Patent Application Publication 2004/ 0116784 to Gavish, all of which are incorporated herein by reference). Such bio-modification has been attempted using biofeedback techniques based on continuous measurement and providing visual/auditory feedback related to the magnitude of the monitored parameters.

Some researchers believe that optimal awakening occurs if an individual is awakened during light or REM sleep, rather than during deep sleep stages. For example, Axon Sleep Research Laboratories (Providence, R.I., USA) is developing an intelligent alarm clock (called "SleepSmart") that monitors sleep cycles and attempts to awaken the user at an optimal point in the sleep cycle. SleepSmart requires the user to sleep with a headband that measures physiological data. It has also been suggested that sleep staging can be obtained from respiration and heart rate information during sleep (see, for example, Shinar Z et al., "Identification of arousals using heart rate beat-to-beat variability," Sleep 21(3 Suppl):294 (1998), which is incorporated herein by reference).

The following articles, which are incorporated herein by reference, may be of interest:

Alihanka J et al., "A new method for long-term monitoring of the ballistocardiogram, heart rate, and respiration," Am J Physiol Regul Integr Comp Physiol 240:384-392 (1981).

Bentur L et al., "Wheeze monitoring in children for assessment of nocturnal asthma and response to therapy," Eur Respir J 21(4):621-626 (2003).

Chang A B et al., "Cough, airway inflammation, and mild asthma exacerbation," Archives of Disease in Childhood 86:270-275 (2002).

Hsu J Y et al., "Coughing frequency in patients with persistent cough: assessment using a 24 hour ambulatory recorder," Eur Respir J 7:1246-1253 (1994).

Mack D et al., "Non-invasive analysis of physiological signals: NAPS: A low cost, passive monitor for sleep quality and related applications," University of Virginia Health System (undated).

Korpas J, "Analysis of the cough sound: an overview," Pulmonary Pharmacology 9:261-268 (1996).

Piirila P et al., "Objective assessment of cough," Eur Respir J 8:1949-1956 (1995).

Salmi T et al., "Long-term recording and automatic analysis of cough using filtered acoustic signals and movements on static charge sensitive bed," Chest 94:970-975 (1988).

Salmi T et al., "Automatic analysis of sleep records with static charge sensitive bed," Electroencephalography and Clinical Neurophysiology 64:84-87 (1986).

Stegmaier-Stracca P A et al., "Cough detection using fuzzy classification," Symposium on Applied Computing, Proceedings of the 1995 ACM Symposium on Applied Computing, Nashville, Tenn., United States, pp. 440-444 (1995).

Van der Loos H F M et al., "Unobtrusive vital signs monitoring from a multisensor bed sheet," RESNA'2001, Reno, Nev., Jun. 22-26, 2001.

Waris M et al., "A new method for automatic wheeze detection," Technol Health Care 6(1):33-40 (1998).

"British Guideline on the Management of Asthma: A national clinical guideline," British Thoracic Society, Scottish Intercollegiate Guidelines Network, Revised edition April 2004.

Brenner B E et al., "The clinical presentation of acute asthma in adults and children," In Brenner, B E, ed. Emergency Asthma (New York: Marcel Dekker, 1999:201-232).

Baren et al., "Current concepts in the ED treatment of pediatric asthma," Respiratory Medicine Consensus Reports (Thomson American Health Consultants, Dec. 28, 2003).

"Managing Asthma," KidsHealth website, (kidshealth.org/parentimedical/lungs/asthmamgmt.html).

"Signs and symptoms of asthma," Indian Chest Society (Mumbai, India) (http://www.indianchestsociety.org/symptomsofasthma.htm).

"Breathing easier with asthma," Intermountain Health Care Clinical Education Services (http://www.ihc.com/xp/ihc/documents/clinical/101/3/1/asthma_breathe.pdf).

"Medical Mutual clinical practice guidelines for asthma: 2004," Medical Mutual (Cleveland, Ohio) (http://www.medmutual.com/provider/pdf/resources/asthma4.pdf)

"Peak flow learning center," National Jewish Medical and Research Center (http://www.njc.org/disease-info/diseases/asthma/living/tools/peak/index.aspx).

Mintzer R, "What the teacher should know about asthma attacks," Family Education Network (http://www.familyeducation.com/article/0,1120,65-415,00.html).

"'Does my child have asthma?'," Solano Asthma Coalition, American Lung Association of the East Bay (http://www.alaebay.org/misc_pdf/solano_asthma_coalition_child_asthma.pdf).

Poteet J, "Asthma" (http://www.nku.edu/~rad350/asthma-jp.html).

Plaut T, "Tracking and treating asthma in young children," J Respir Dis Pediatrician 5(2):67-72 (2003).

The inclusion of the foregoing references in this Background section does not imply that they constitute prior art or analogous art with respect to the invention disclosed herein.

SUMMARY OF THE INVENTION

In some embodiments of the present invention, a method for monitoring a chronic medical condition comprises non-invasively monitoring at least one breathing pattern and/or at least one heartbeat pattern of a subject, typically during sleep at night. The patterns are analyzed in order to (a) predict an approaching clinical episode, such as an asthma attack or congestive heart failure deterioration, and/or (b) monitor the severity and progression of a clinical episode as it occurs. Analyzing the patterns typically comprises comparing the patterns to respective baseline patterns. Prediction of an approaching clinical episode facilitates early preventive treatment, which generally reduces the required dosage of medication. For some applications, the method additionally comprises monitoring additional potential indicators of the approaching clinical episode, such as body temperature, coughing, sleep restlessness, and/or blood pressure. For some applications, prediction or monitoring of a clinical episode is based only on one or more of these additional potential indicators.

In some embodiments of the present invention, the breathing and heartbeat patterns are monitored by substantially continuously acquiring breathing- and heartbeat-related body motion data of the subject during sleep, typically throughout night sleep (e.g., during at least 80% of night sleep). The motion data is processed to yield at least one periodic breathing-related movement pattern, from which the breathing pattern is extracted, and/or at least one periodic heartbeat-related movement pattern, from which the heartbeat pattern is extracted. For some applications, the motion data is acquired using a sensing device that does not come in contact with or view the subject or clothes the subject is wearing. For example, the sensing device may comprise a pressure or strain gauge, which is typically adapted to be installed under or in a mattress, mattress pad, mattress cover, or sheet upon which the subject sleeps, and to detect mechanical perturbations caused by breathing and cardiac activity. For some applications, additional potential indicators, such as coughing and sleep restlessness, are also extracted from the motion data. Because the data acquisition is non-invasive (and typically not noticeable), it is generally suitable for monitoring both children and adults in a home environment.

Use of the techniques described herein generally enables detection of the approaching clinical episode before the subject becomes aware of the episode. For example, an asthma attack is typically predicted before the subject becomes aware of any perceptible early warning signs, such as increased respiration rate. Typically, an asthma attack is predicted before the subject's respiration rate has substantially increased, e.g., before the respiration rate has increased by 20%, such as by 10% or 5%, vs. baseline (i.e., normal breathing rate when the subject is experiencing substantially no symptoms of asthma). Furthermore, an asthma attack is typically predicted before forced expiratory volume in one second (FEV1) of the subject has declined 10% vs. baseline. A clinical episode is typically predicted at least one hour, e.g., at least four hours, prior to its onset.

The sensing techniques described herein typically do not require compliance by the subject or another human (e.g., the subject's parent or healthcare worker). "Compliance" is to be understood herein, including in the claims, as the active involvement of a human in measuring one or more physiological parameters for use in predicting or monitoring a clinical episode, such as by observing a physiological parameter of the subject, either manually or by performing a test (e.g., by standing on a scale). Merely performing an action that would otherwise be performed, such as lying down in bed to go to sleep at night, does not fall within the scope of "compliance." Similarly, the initial, one-time placement of a sensor in its proper location (e.g., under a mattress, or at an implantation site within a patient), or performance of periodic maintenance, such as battery replacement, is not considered to fall within the scope of "compliance" in facilitating ongoing measurements. Likewise, post-sensing on-site or remote interpretation of the measured physiological parameters by a human is not considered to fall within the scope of "compliance."

The effectiveness of the techniques described herein is in part based on the observation that some chronic medical conditions interfere with normal breathing and cardiac cycles during sleep and while awake, resulting in condition-specific abnormal breathing and heartbeat patterns. Various physiological mechanisms modify breathing and heartbeat patterns, resulting in specific patterns related to the cause of modification. Respiratory diseases, such as asthma, chronic obstructive pulmonary disease (COPD), and cystic fibrosis (CF), and physiological abnormalities associated with some conditions modify breathing and heartbeat patterns. For example, such breathing pattern-modifying physiological abnormalities include: (a) congestive heart failure (CHF), which sometimes causes abnormal breathing patterns such as Cheyne-Stokes Respiration (CSR) or periodic breathing, (b) hypoglycemia, such as caused by diabetes, and (c) abnormal autonomic nervous system activity, such as caused by some neurological conditions.

Fluid retention in lung tissue, which often occurs during periodic worsening of a heart condition, is correlated with changes in cardiac activity and respiratory patterns. In some embodiments of the present invention, a method is provided for monitoring a chronic heart failure subject, typically in his home. In other embodiments of the present invention, a method is provided for prediction and assessment of cardiac status of a subject, by non-invasively monitoring breathing and heartbeat patterns during night sleep. In still other embodiments, a method is provided for generating an early warning of an impending clinical worsening of the heart condition, upon early buildup of lung fluid, thereby facilitating treatment before the clinical symptoms become more severe.

In some embodiments of the present invention, coughing episodes associated with approaching or occurring clinical episodes are detected and/or assessed. In asthma, mild coughing is often an important early pre-episode marker indicating an upcoming onset of a clinical asthma episode. In congestive heart failure (CHF), coughing may provide an early warning of fluid retention in the lungs caused by worsening of heart failure or developing cardiovascular insufficiency.

In some embodiments of the present invention, a method is provided comprising monitoring restlessness manifested by excessive body movement during sleep. The restlessness is quantified to provide an objective measure of nocturnal restlessness. Typically, body movement is acquired using a sensing device that does not come in contact with or view the subject or clothes the subject is wearing. For some applications, Periodic Limb Movements in Sleep (PLMS) is identified. The occurrence and level of this syndrome is used as an indicator of the onset or worsening of chronic conditions, such as CHF, diabetes, anemia, kidney disease, and asthma.

In some embodiments of the present invention, parameters such as respiration, heart rate, and/or coughing are monitored during sleep at night. The parameters are analyzed either continuously or after the conclusion of sleep, such as in the morning, to predict an approaching clinical episode. In the morning, or later in the day, the subject is alerted about the approaching clinical event. Such approaching clinical events generally do not occur until at least several hours after their approach has been predicted. Therefore, delaying notification until the morning or later in the day still generally provides sufficient time for the subject to begin preventive treatment before clinical manifestation of the episode begins, without needlessly interrupting the subject's sleep. For some applications, the parameters are analyzed to estimate a severity and/or urgency of the approaching clinical episode, and to determine whether to wake the subject responsively to the severity and/or urgency.

In some embodiments of the present invention, a clinical episode is predicted or monitored by assessing deviations of measured parameters from baseline parameters, taking into account information regarding medical treatment the subject is currently receiving, such as drug and dosage information. For some applications, drug treatment information is directly received from a drug administration device, while for other applications the information is manually provided by the subject or a healthcare worker.

In some embodiments of the present invention, a method is provided comprising sensing a motion-related parameter of a subject while the subject sleeps, without contacting or viewing the subject or clothes the subject is wearing, and analyzing the parameter. Responsively at least in part to the analysis, a dosage of a drug for administration to the subject is determined, and the dosage is communicated to a drug administration device used by the subject. Typically, the clinical effect of the drug is monitored, and feedback is provided to the drug administration device to maintain or update the drug dosage.

In some embodiments of the present invention, a method is provided for monitoring a fetus in a pregnant subject. The method comprises sensing a motion-related parameter of the subject without contacting or viewing the subject or clothes the subject is wearing. For some applications, the motion-related parameter is sensed by measuring a pressure in, on, or under a reclining surface upon which the subject lies (e.g., a regular bed). The motion-related parameter is analyzed to derive a heartbeat of the fetus, and/or a measure of motion of the fetus.

In some embodiments of the present invention, a method is provided comprising sensing a motion-related parameter of a subject without contacting or viewing the subject or clothes the subject is wearing. Heartbeat- and breathing-related signals are derived from the motion-related parameter. The heartbeat-related signal is demodulated using the breathing-related signal, such as by multiplying the heartbeat-related signal by the breathing-related signal.

In some embodiments of the present invention, a method is provided for predicting an onset of a clinical episode. The method comprises acquiring a breathing-related body motion time-domain signal of a subject, and transforming the time-domain signal into a frequency-domain signal. A breathing rate of the subject is determined by identifying a peak in a breathing-related frequency range of the frequency-domain signal. One or more harmonics of the peak frequency are identified. One or more ratios between the energy levels of the one or more harmonics and of a frequency of the peak are calculated and compared with one or more respective baseline ratios. The onset of the episode is predicted at least in part responsively to the comparison.

In some embodiments of the present invention, a method is provided for identifying early signs of an onset of hypoglycemia in a diabetic subject, by identifying an increase in a level of physiological tremor. Typically, physiologic tremor is detected by monitoring body motion at between about 4 Hz and about 18 Hz, such as between about 8 Hz and about 12 Hz. Alternatively, the increase in the level of physiological tremor is considered indicative of an onset or progression of a condition selected from the list consisting of: Parkinson's disease, Alzheimer's disease, stroke, essential tremor, epilepsy, stress, fibrillation, and anaphylactic shock. In some embodiments, the hypoglycemia is identified by analyzing the heart signal to identify palpitations.

In some embodiments of the present invention, a system for monitoring chronic medical conditions comprises a breathing-related motion acquisition module, a breathing pattern analysis module, and an output module.

In some embodiments of the present invention, a method is provided for identifying a change in the condition of at least one patient in a hospital, such as in a surgical or medical ward. The change typically includes a deterioration that requires rapid intervention. The method is typically performed without contacting or viewing the patient or clothes the patient is wearing, without limiting the mobility of the patient, and without requiring any effort by the nursing staff or other healthcare workers.

There is therefore provided, in accordance with an embodiment of the present invention, a method for predicting an onset of a clinical episode, including:

sensing breathing of a subject;

determining at least one breathing pattern of the subject responsively to the sensed breathing;

comparing the breathing pattern with a baseline breathing pattern; and predicting the onset of the episode at least in part responsively to the comparison.

For some applications, the breathing pattern includes a breathing rate pattern of the subject, the baseline breathing pattern includes a baseline breathing rate pattern, and comparing the breathing pattern with the baseline breathing pattern includes comparing the breathing rate pattern with the baseline breathing rate pattern.

For some applications, comparing includes determining the baseline breathing pattern by analyzing breathing of the subject during at least one non-symptomatic period. For some applications, comparing includes setting the baseline breathing pattern responsively to a population average breathing pattern.

For some applications, predicting the onset includes predicting the onset responsively to a prolonged inspirium time of the subject, and/or to a prolonged expirium time of the subject. For some applications, the breathing pattern includes successive segments of inspirium and expirium, and predicting the onset includes predicting the onset responsively to a trend towards greater durations of at least one of: the inspirium segments and the expirium segments.

In an embodiment, the clinical episode includes an episode associated with a condition selected from the list consisting of: asthma, chronic obstructive pulmonary disease (COPD), cystic fibrosis (CF), CHF, diabetes, and epilepsy.

In an embodiment, the breathing pattern includes a breathing duty-cycle pattern, and predicting the onset includes predicting the onset responsively to an increase in a breathing duty-cycle of the subject.

For some applications, sensing breathing of the subject includes sensing at least one breathing-related sound selected from the list consisting of: a sound caused by wheezing, and a sound caused by coughing, and predicting the onset includes predicting the onset responsively to an aspect of the breathing-related sound.

For some applications, sensing breathing of the subject includes sensing at least one type of breathing-related mechanical vibrations selected from the list consisting of: mechanical vibrations caused by wheezing, and mechanical vibrations caused by coughing, and predicting the onset includes predicting the onset responsively to an aspect of the breathing-related mechanical vibrations.

In an embodiment, the breathing pattern includes a breathing rate variability pattern, the baseline breathing pattern includes a baseline breathing rate variability pattern, and predicting the onset includes predicting the onset responsively to a decrease in breathing rate variability over time compared to the baseline breathing rate variability pattern. For some applications, determining the at least one breathing pattern includes determining the breathing rate variability pattern and a slow trend breathing rate pattern, comparing the breathing pattern with the baseline breathing pattern includes comparing the breathing rate variability pattern with the baseline breathing rate variability pattern, and comparing the slow trend breathing rate pattern with a baseline slow trend breathing rate pattern, and predicting the onset includes predicting the onset responsively to both comparisons. For some applications, sensing the breathing includes sensing at least one of: breathing sounds of the subject, and respiratory air-flow of the subject. For some applications, the clinical episode includes an asthma attack, and predicting the onset of the episode includes predicting the onset of the asthma attack.

In an embodiment, the breathing pattern and the baseline breathing pattern include respective slow trend breathing rate patterns, and comparing the breathing pattern with the baseline breathing pattern includes comparing the slow trend breathing rate pattern with the baseline slow trend breathing rate pattern. For some applications, the baseline slow trend breathing rate pattern includes a monotonic decline in breathing rate over at least 1 hour, and predicting the onset includes predicting the onset responsively to a difference between the slow trend breathing rate pattern and the monotonic decline in breathing rate.

In an embodiment, sensing the breathing includes acquiring breathing-related body motion data of the subject. For some applications, acquiring the body motion data includes acquiring the body motion data while the subject is sleeping. For some applications, determining the breathing pattern includes analyzing the body motion data to determine a breathing-related movement pattern, and determining the breathing pattern responsively to the breathing-related movement pattern. For some applications, determining the breathing pattern includes removing non-breathing-related motion data from the body motion data. For example, removing the non-breathing-related motion data from the body motion data may include applying analysis techniques such as frequency-domain spectral analysis or time-domain regression analysis.

In an embodiment, acquiring the body motion data includes acquiring the body motion data without contacting the subject or clothes the subject is wearing. For some applications, the clinical episode includes an asthma attack, and predicting the onset of the episode includes predicting the onset of the asthma attack. For some applications, acquiring the breathing-related body motion data includes measuring a pressure. For some applications, measuring the pressure includes measuring a pressure at a mattress upon which the subject lies. Alternatively or additionally, measuring the pressure includes measuring a pressure under or in a mattress upon which the subject lies. Further alternatively or additionally, measuring the pressure includes measuring a pressure under or in a mattress covering upon which the subject lies, for example, a sheet, a mattress pad, or a mattress cover.

For some applications, the breathing pattern includes a breathing rate variability pattern, the baseline breathing pattern includes a baseline breathing rate variability pattern, and predicting the onset includes predicting the onset responsively to a decrease in breathing rate variability over time compared to the baseline breathing rate variability pattern. For some applications, determining the at least one breathing pattern includes determining the breathing rate variability pattern and a slow trend breathing rate pattern; comparing the breathing pattern with the baseline breathing pattern includes comparing the breathing rate variability pattern with the baseline breathing rate variability pattern, and comparing the slow trend breathing rate pattern with a baseline slow trend breathing rate pattern; and predicting the onset includes predicting the onset responsively to both comparisons.

There is also provided, in accordance with an embodiment of the present invention, a method including:

sensing breathing of a subject during a clinical episode;

determining at least one breathing pattern of the subject responsively to the sensed breathing;

comparing the breathing pattern with a baseline breathing pattern; and assessing a progression of the episode at least in part responsively to the comparison.

For some applications, the breathing pattern includes a breathing rate pattern of the subject, the baseline breathing pattern includes a baseline breathing rate pattern, and comparing the breathing pattern with the baseline breathing pattern includes comparing the breathing rate pattern with the baseline breathing rate pattern.

For some applications, assessing the progression includes assessing the progression responsively to a prolonged inspirium time of the subject, and/or to a prolonged expirium time of the subject.

For some applications, the breathing pattern includes successive segments of inspirium and expirium, and assessing the progression includes assessing the progression responsively to a trend towards greater durations of at least one of: the inspirium segments and the expirium segments.

In an embodiment, the clinical episode includes an episode associated with a condition selected from the list consisting of: asthma, chronic obstructive pulmonary disease (COPD), cystic fibrosis (CF), CHF, diabetes, and epilepsy.

In an embodiment, the breathing pattern includes a breathing duty-cycle pattern, and assessing the progression includes assessing the progression responsively to an increase in a breathing duty-cycle of the subject.

For some applications, sensing breathing of the subject includes sensing at least one breathing-related sound selected from the list consisting of: a sound caused by wheezing, and a sound caused by coughing, and assessing the progression includes assessing the progression responsively to an aspect of the breathing-related sound. For some applications, the clinical episode includes an asthma attack, and assessing the progression includes assessing the progression of the asthma attack responsively to the aspect.

For some applications, sensing breathing of the subject includes sensing at least one type of breathing-related mechanical vibrations selected from the list consisting of: mechanical vibrations caused by wheezing, and mechanical vibrations caused by coughing, and assessing the progression includes assessing the progression responsively to an aspect of the breathing-related mechanical vibrations. For some applications, the clinical episode includes an asthma attack, and assessing the progression includes assessing the progression of the asthma attack responsively to the aspect.

In an embodiment, the breathing pattern includes a breathing rate variability pattern, the baseline breathing pattern includes a baseline breathing rate variability pattern, and assessing the progression includes assessing the progression responsively to a decrease in breathing rate variability over time compared to the baseline breathing rate variability pattern. For some applications, determining the at least one breathing pattern includes determining the breathing rate variability pattern and a slow trend breathing rate pattern; comparing the breathing pattern with the baseline breathing pattern includes comparing the breathing rate variability pattern with the baseline breathing rate variability pattern, and comparing the slow trend breathing rate pattern with a baseline slow trend breathing rate pattern; and assessing the progression includes assessing the progression responsively to both comparisons. For some applications, the clinical episode includes an asthma attack, and assessing the progression of the episode includes assessing a severity of the asthma attack.

In an embodiment, the breathing pattern and the baseline breathing pattern include respective slow trend breathing rate patterns, and comparing the breathing pattern with the baseline breathing pattern includes comparing the slow trend breathing rate pattern with the baseline slow trend breathing rate pattern. For some applications, the baseline slow trend breathing rate pattern includes a monotonic decline in breathing rate over at least 1 hour, and assessing the progression includes assessing the progression responsively to a difference between the slow trend breathing rate pattern and the monotonic decline in breathing rate.

In an embodiment, sensing the breathing includes acquiring breathing-related body motion data of the subject. For some applications, determining the breathing pattern includes analyzing the body motion data to determine a breathing-related movement pattern, and determining the breathing pattern responsively to the breathing-related movement pattern.

In an embodiment, acquiring the body motion data includes acquiring the body motion data without contacting the subject or clothes the subject is wearing. For some applications, the clinical episode includes an asthma attack, and assessing the progression of the episode includes assessing a severity of the asthma attack. For some applications, acquiring the breathing-related body motion data includes measuring a pressure. For some applications, measuring the pressure includes measuring a pressure at a mattress upon which the subject lies. Alternatively or additionally, measuring the pressure includes measuring a pressure under or in a mattress upon which the subject lies. Further alternatively or additionally, measuring the pressure includes measuring a pressure under or in a mattress covering upon which the subject lies, for example, a sheet, a mattress pad, or a mattress cover.

For some applications, the breathing pattern includes a breathing rate variability pattern, the baseline breathing pattern includes a baseline breathing rate variability pattern, and assessing the progression includes assessing the progression responsively to a decrease in breathing rate variability over time compared to the baseline breathing rate variability pattern. For some applications, determining the at least one breathing pattern includes determining the breathing rate variability pattern and a slow trend breathing rate pattern; comparing the breathing pattern with the baseline breathing pattern includes comparing the breathing rate variability pattern with the baseline breathing rate variability pattern, and comparing the slow trend breathing rate pattern with a baseline slow trend breathing rate pattern; and assessing the progression includes assessing the progression responsively to both comparisons.

There is further provided, in accordance with an embodiment of the present invention, a method including:

sensing breathing of a subject;

determining at least one breathing pattern of the subject responsively to the sensed breathing;

comparing the breathing pattern with a baseline breathing pattern; and detecting an abnormal breathing pattern associated with congestive heart failure (CHF), at least in part responsively to the comparison.

For some applications, determining the breathing pattern includes determining a breathing rate pattern of the subject, and comparing the breathing pattern with the baseline breathing pattern includes comparing the breathing rate pattern with a baseline breathing rate pattern.

For some applications, detecting the abnormal breathing pattern includes detecting Cheyne-Stokes Respiration (CSR), detecting periodic breathing, and/or detecting tachypnea.

In an embodiment, sensing the breathing includes acquiring breathing-related body motion data of the subject. For some applications, acquiring the body motion data includes acquiring the body motion data while the subject is sleeping.

In an embodiment, acquiring the body motion data includes acquiring the body motion data without contacting the subject or clothes the subject is wearing. For some applications, detecting the abnormal breathing pattern includes detecting Cheyne-Stokes Respiration (CSR), detecting periodic breathing, and/or tachypnea.

For some applications, acquiring the breathing-related body motion data includes measuring a pressure. For some applications, measuring the pressure includes measuring a pressure at a mattress upon which the subject lies. Alternatively or additionally, measuring the pressure includes measuring a pressure under or in a mattress upon which the subject lies. Further alternatively or additionally, measuring the pressure includes measuring a pressure under or in a mattress covering upon which the subject lies, for example, a sheet, a mattress pad, or a mattress cover.

There is further provided, in accordance with an embodiment of the present invention, a method including:
  sensing breathing of a subject;
  determining at least one breathing pattern of the subject responsively to the sensed breathing;
  comparing the breathing pattern with a baseline breathing pattern; and
  detecting an abnormal breathing pattern associated with a condition of the subject, at least in part responsively to the comparison, the condition selected from the list consisting of: chronic obstructive pulmonary disease (COPD), cystic fibrosis (CF), diabetes, and epilepsy.

For some applications, determining the breathing pattern includes determining a breathing rate pattern of the subject, and comparing the breathing pattern with the baseline breathing pattern includes comparing the breathing rate pattern with a baseline breathing rate pattern.

In an embodiment, sensing the breathing includes acquiring breathing-related body motion data of the subject. For some applications, acquiring the body motion data includes acquiring the body motion data while the subject is sleeping.

In an embodiment, acquiring the body motion data includes acquiring the body motion data without contacting the subject or clothes the subject is wearing.

For some applications, acquiring the breathing-related body motion data includes measuring a pressure. For some applications, measuring the pressure includes measuring a pressure at a mattress upon which the subject lies. Alternatively or additionally, measuring the pressure includes measuring a pressure under or in a mattress upon which the subject lies. Further alternatively or additionally, measuring the pressure includes measuring a pressure under or in a mattress covering upon which the subject lies, for example, a sheet, a mattress pad, or a mattress cover.

There is still further provided, in accordance with an embodiment of the present invention, apparatus for predicting an onset of a clinical episode, including:
  a breathing sensor, adapted to sense breathing of a subject, and to generate a signal responsively thereto; and
  a control unit, adapted to:
  receive the signal,
  determine at least one breathing pattern of the subject responsive to the signal,
  compare the breathing pattern with a baseline breathing pattern, and
  predict the onset of the episode at least in part responsively to the comparison.

There is additionally provided, in accordance with an embodiment of the present invention, apparatus including:
  a breathing sensor, adapted to sense breathing of a subject during a clinical episode, and to generate a signal responsively thereto; and
  a control unit, adapted to:
  receive the signal,
  determine at least one breathing pattern of the subject responsive to the signal,
  compare the breathing pattern with a baseline breathing pattern, and
  assess a progression of the episode at least in part responsively to the comparison.

There is still additionally provided, in accordance with an embodiment of the present invention, apparatus including:
  a breathing sensor, adapted to sense breathing of a subject during a clinical episode, and to generate a signal responsively thereto; and
  a control unit, adapted to:
  receive the signal,
  determine at least one breathing pattern of the subject responsive to the signal,
  compare the breathing pattern with a baseline breathing pattern, and
  detect an abnormal breathing pattern associated with congestive heart failure (CHF), at least in part responsively to the comparison.

There is additionally provided, in accordance with an embodiment of the present invention, apparatus including:
  a breathing sensor, adapted to sense breathing of a subject during a clinical episode, and to generate a signal responsively thereto; and
  a control unit, adapted to:
  receive the signal,
  determine at least one breathing pattern of the subject responsive to the signal,
  compare the breathing pattern with a baseline breathing pattern, and
  detect an abnormal breathing pattern associated with a condition of the subject, at least in part responsively to the comparison, the condition selected from the list consisting of: chronic obstructive pulmonary disease (COPD), cystic fibrosis (CF), diabetes, and epilepsy.

There is also provided, in accordance with an embodiment of the present invention, a method for clinical episode prediction and assessment, including:
  measuring breathing rate variability patterns during night sleep;
  comparing said breathing rate variability patterns to normal breathing rate variability patterns; and
  determining a likelihood of a nearing clinical episode or a progression or severity of an ongoing episode.

For some applications, said measuring of breathing rate variability patterns is executed by means of measurement of a composite body movement signal and extraction of a periodic, breathing-related movement signal from said composite body movement signal. Alternatively, said measuring of breathing rate variability patterns is executed by means of measurement of respiration airflow from a mouth and/or a nose. Further alternatively, said measuring of breathing rate variability patterns is executed by means of acoustic measurement of airway and lung sounds from a chest, a back, a neck, and/or a face.

For some applications, said normal breathing rate patterns are extracted from the patient during non-symptomatic periods. For some applications, the normal breathing rate patterns are extracted from averaged patterns of normal, healthy subjects with similar character of age, height, weight, and/or gender.

For some applications, said breathing rate variability patterns include: (1) cyclic patterns, whose typical durations range from several seconds to several minutes, and/or (2) slow trends of segmented, monotonically declining breathing rate usually lasting several hours.

For some applications, said comparing is based on a calculation of a degree of deviation of said breathing rate variability patterns from said normal breathing rate variability patterns.

In an embodiment, said clinical episode is a clinical asthma episode.

For some applications, said clinical episode relates to any chronic disease affecting breathing rate patterns, such as diabetes, a heart condition, a neurological disorder, or epilepsy.

There is further provided, in accordance with an embodiment of the present invention, apparatus for clinical episode assessment and prediction, including:
a breathing sensor which measures breathing;
an amplifier which amplifies the output signal of the breathing sensor;
an A/D card which digitizes the amplifier output;
a processor, which extracts breathing rate patterns and compares said patterns to normal patterns; and
an output device presenting the result on a numerical, textual or graphical display, or transmitting the results to a clinical follow-up center.

For some applications, the breathing sensor is implemented as a motion-sensitive sensor installed under or in a bed mattress. Alternatively, the breathing sensor is implemented as an airflow detector aimed at a face of the subject. Further alternatively, the breathing sensor is implemented as an acoustic detector aimed or attached to a face, chest, or back of the subject.

There is also provided, in accordance with an embodiment of the present invention, a method including:
sensing a motion-related parameter of a subject without contacting or viewing the subject or clothes the subject is wearing;
deriving heartbeat- and breathing-related signals from the motion-related parameter; and
demodulating the heartbeat-related signal using the breathing-related signal.

For some applications, demodulating the heartbeat-related signal includes multiplying the heartbeat-related signal by the breathing-related signal. For some applications, deriving the heartbeat- and breathing-related signals includes filtering the motion-relating signals at heartbeat- and breathing-related frequency ranges, respectively. For some applications, the heartbeat-related frequency range is between 0.8 and 5 Hz. For some applications, the breathing-related frequency range is between 0.05 and 0.8 Hz.

There is further provided, in accordance with an embodiment of the present invention, a method for measuring a heartbeat of a fetus in a pregnant subject, including:
sensing a motion-related parameter of the pregnant subject without contacting or viewing the subject or clothes the subject is wearing; and
deriving the fetal heartbeat from the motion-related parameter.

In an embodiment, sensing the motion-related parameter includes measuring a pressure in, on, or under a reclining surface upon which the subject lies.

In an embodiment, the method includes generating an acoustic signal of the derived fetal heartbeat by simulating a sound generated by a fetal monitor.

For some applications, the method includes determining a measure of fetal heart rate variability by analyzing the derived fetal heartbeat. For some applications, deriving the fetal heartbeat includes deriving a first signal from the motion-related parameter that is indicative of both the fetal heartbeat and a maternal heartbeat, and deriving, from the first signal, a second signal indicative of the fetal heartbeat and not indicative of the maternal heartbeat.

For some applications, deriving the fetal heartbeat includes deriving from the motion-related parameter: (a) a maternal breathing-related signal and (b) a fetal heartbeat-related signal; and demodulating the fetal heartbeat-related signal using the maternal breathing-related signal.

There is still further provided, in accordance with an embodiment of the present invention, a method for monitoring movement of a fetus in a pregnant subject, including:
sensing a motion-related parameter of the pregnant subject without contacting or viewing the subject or clothes the subject is wearing; and
deriving a measure of motion of the fetus from the motion-related parameter.

In an embodiment, sensing the motion-related parameter includes measuring a pressure in, on, or under a reclining surface upon which the subject lies.

There is additionally provided, in accordance with an embodiment of the present invention, a method including:
sensing at least one parameter of a subject while the subject sleeps;
analyzing the parameter;
predicting an onset of a clinical episode at least in part responsively to the analysis; and
alerting the subject to the predicted onset only after the subject awakes.

There is still additionally provided, in accordance with an embodiment of the present invention, a method for predicting an onset of a clinical episode, including:
acquiring a breathing-related time-domain signal of a subject;
transforming the time-domain signal into a frequency-domain signal;
determining a breathing rate of the subject by identifying a peak in a breathing-related frequency range of the frequency-domain signal;
determining one or more harmonics of the peak frequency;
determining a relationship between:
(a) a first energy level, selected from the list consisting of: an energy level associated with one of the one or more harmonics, and an energy level associated with a frequency of the peak, and
(b) a second energy level, associated with one of the one or more harmonics;
comparing the relationship with a baseline level of the relationship; and predicting the onset of the episode at least in part responsively to the comparison.

There is additionally provided, in accordance with an embodiment of the present invention, a method for monitoring blood pressure, including:

sensing a motion-related parameter of a subject without contacting or viewing the subject or clothes the subject is wearing; and analyzing the parameter to determine a measure of blood pressure of the subject.

For some applications, sensing the motion-related parameter includes sensing first and second motion-related parameters of the subject in a vicinity of a first site and in a vicinity of a second site of the subject, respectively, without contacting or viewing the subject or clothes the subject is wearing.

There is also provided, in accordance with an embodiment of the present invention, a method for treating a subject, including:

sensing a motion-related parameter of a subject without contacting or viewing the subject or clothes the subject is wearing;

analyzing the parameter;

responsively at least in part to the analysis, determining an initial dosage of a drug for administration to the subject; and communicating the initial dosage to a drug administration device used by the subject.

For some applications, analyzing the parameter includes:

analyzing a clinical effect of the drug administered by the drug administration device at the communicated initial dosage;

responsively to the analysis, determining an updated dosage of the drug, which updated dosage is different from the initial dosage; and communicating the updated dosage to the drug administration device.

There is further provided, in accordance with an embodiment of the present invention, a method for predicting an onset of a clinical episode, including:

sensing at least one parameter of a subject;

analyzing the parameter;

receiving data regarding a drug administered to the subject; and predicting the onset of a clinical episode at least in part responsively to the analysis and the drug administration data in combination.

For some applications, receiving the drug administration data includes receiving the drug administration data from a drug administration device that administers the drug to the subject. For some applications, the drug administration data includes a dosage of the drug. For some applications, sensing the at least one parameter includes sensing the at least one parameter while the subject is sleeping.

There is still further provided, in accordance with an embodiment of the present invention, a method for treating a clinical episode, including:

sensing at least one parameter of a subject without contacting or viewing the subject or clothes the subject is wearing;

analyzing the parameter;

detecting the clinical episode at least in part responsively to the analysis; and responsively to detecting the clinical episode, treating the clinical episode using a device implanted in the subject.

There is additionally provided, in accordance with an embodiment of the present invention, a method including:

sensing at least one parameter of a subject while the subject sleeps, without contacting or viewing the subject or clothes the subject is wearing; and analyzing the parameter to determine a measure of restlessness of the subject.

In an embodiment, the at least one parameter includes at least one motion-related parameter of the subject, and sensing the at least one parameter includes sensing the at least one motion-related parameter.

There is still additionally provided, in accordance with an embodiment of the present invention, a method including:

sensing at least one parameter of a subject while the subject sleeps, without contacting or viewing the subject or clothes the subject is wearing; and detecting Periodic Limb Movements in Sleep (PLMS) of the subject by analyzing the parameter.

In an embodiment, the at least one parameter includes at least one motion-related parameter of the subject, and sensing the at least one parameter includes sensing the at least one motion-related parameter.

There is additionally provided, in accordance with an embodiment of the present invention, a method including:

sensing at least one parameter of a subject, using exactly one sensor placed in or under a reclining surface upon which the subject lies, which sensor does not contact the subject or clothes the subject is wearing; and detecting coughing of the subject by analyzing the parameter.

In an embodiment, the at least one parameter includes at least one motion-related parameter of the subject, and sensing the at least one parameter includes sensing the at least one motion-related parameter.

There is also provided, in accordance with an embodiment of the present invention, a method for predicting an onset of an asthma attack, including:

sensing breathing of a subject;

sensing a heartbeat of the subject;

determining at least one breathing pattern of the subject responsively to the sensed breathing, and at least one heart pattern of the subject responsively to the sensed heartbeat;

comparing the breathing pattern with a baseline breathing pattern, and the heart pattern with a baseline heart pattern; and predicting the onset of the asthma attack at least in part responsively to the comparisons.

In an embodiment, determining the at least one breathing pattern and the at least one heart pattern includes determining at least one breathing rate pattern of the subject and at least one heart rate pattern of the subject, respectively; comparing the breathing pattern with the baseline breathing pattern includes comparing the breathing rate pattern with a baseline breathing rate pattern; and comparing the heart pattern with the baseline heart pattern includes comparing the heart rate pattern with a baseline heart rate pattern.

In an embodiment, sensing the breathing and the heartbeat include sensing at least one motion-related parameter of the subject, and deriving the breathing and heartbeat from the motion-related parameter. For some applications, the method includes deriving at least one additional physiological parameter from the motion-related parameter, and predicting the onset includes predicting the onset at least in part responsively to the comparison and to the additional physiological parameter. For some applications, the additional physiological parameter is selected from the list consisting of: a measure of coughs of the subject, a ratio of expiration to inspiration time of the subject, a blood pressure of the subject, a measure of restlessness during sleep of the subject, and a measure of arousals during sleep of the subject.

There is further provided, in accordance with an embodiment of the present invention, a method for predicting an onset of an asthma attack, including:

sensing breathing of a subject;

determining at least one breathing pattern of the subject responsively to the sensed breathing;

comparing the breathing pattern with a baseline breathing pattern;

determining a measure of coughing of the subject; and predicting the onset of the asthma attack at least in part responsively to the comparison and the measure of coughing.

There is still further provided, in accordance with an embodiment of the present invention, a method for predicting an onset of an episode associated with congestive heart failure (CHF), including:

sensing breathing of a subject;

sensing a blood pressure of the subject;

determining at least one breathing pattern of the subject responsively to the sensed breathing;

comparing the breathing pattern with a baseline breathing pattern; and predicting the onset of the episode at least in part responsively to the comparison and the blood pressure.

There is additionally provided, in accordance with an embodiment of the present invention, a method for determining a heart rate of a subject, including:

sensing a first pulse signal of the subject in a vicinity of a first location of the subject selected from: a chest of the subject, and an abdomen of the subject, without contacting the subject or clothes the subject is wearing;

sensing a second pulse signal of the subject in a vicinity of a second location of the subject anatomically below a waist of the subject, without contacting the subject or clothes the subject is wearing; and determining the heart rate responsively to the first and second pulse signals.

For some applications, determining the heart rate includes calculating a cross correlation signal of the first and second pulse signals, and determining the heart rate to be a frequency of the cross correlation signal. For some applications, the second location of the subject includes a location in a vicinity of legs of the subject.

In an embodiment, sensing the first and second pulse signals includes sensing the first and second pulse signals without contacting or viewing the subject or clothes the subject is wearing.

For some applications, sensing the first pulse signal includes sensing a first motion-related parameter of the subject in the vicinity of the first location, and deriving the first pulse signal from the first motion-related parameter, and sensing the second pulse signal includes sensing a second motion-related parameter of the subject in the vicinity of the second location, and deriving the second pulse signal from the second motion-related parameter.

For some applications, the method includes predicting an onset of a clinical episode responsively to the heart rate.

There is still additionally provided, in accordance with an embodiment of the present invention, a method including:

sensing first and second motion-related parameters of a subject in a vicinity of a first site and in a vicinity of a second site of the subject, respectively, without contacting or viewing the subject or clothes the subject is wearing;

deriving first and second breathing-related signals from the first and second motion-related parameters, respectively; and analyzing the first and second breathing-related signals to determine a measure of thoracoabdominal asynchrony (TAA) of the subject.

For some applications, analyzing the first and second breathing-related signals includes calculating a phase shift between the first and second breathing-related signals.

For some applications, the first site includes lungs of the subject, the second site includes a lower abdomen of the subject, and sensing includes sensing the first and second motion-related parameters in the vicinity of the lungs and lower abdomen, respectively.

There is additionally provided, in accordance with an embodiment of the present invention, a method including:

sensing first and second motion-related parameters of a subject in a vicinity of a first site and in a vicinity of a second site of the subject, respectively, without contacting or viewing the subject or clothes the subject is wearing;

deriving first and second breathing-related signals from the first and second motion-related parameters, respectively; and analyzing the first and second breathing-related signals to determine a measure of accessory muscle activity of the subject.

For some applications, analyzing the first and second breathing-related signals includes calculating a ratio of the first and second breathing-related signals. For some applications, the first site includes lungs of the subject, the second site includes a lower abdomen of the subject, and sensing includes sensing the first and second motion-related parameters in the vicinity of the lungs and lower abdomen, respectively.

There is also provided, in accordance with an embodiment of the present invention, a method for monitoring a subject, including:

setting respective first and second thresholds that are different;

sensing at least one parameter of a subject without contacting or viewing the subject or clothes the subject is wearing;

analyzing the parameter to generate a score;

if the score is between the first and second thresholds, generating a first output indicative of a predicted onset of a clinical episode; and if the score passes the second threshold, generating a second output indicative of a currently occurring clinical episode.

For some applications, sensing the at least one parameter includes sensing a plurality of parameters of the subject without contacting or viewing the subject or the clothes the subject is wearing, and analyzing the parameter to generate the score includes analyzing the plurality of parameters to generate the score.

For some applications, the parameter includes a breathing-related parameter of the subject, and analyzing the parameter includes determining at least one breathing pattern of the subject responsively to the parameter, and comparing the breathing pattern with a baseline breathing pattern.

For some applications, the at least one parameter includes at least one motion-related parameter of the subject, and sensing the at least one parameter includes sensing the at least one motion-related parameter.

There is further provided, in accordance with an embodiment of the present invention, a method for detecting pulsus paradoxus of a subject, including:

sensing at least one parameter of a subject without contacting or viewing the subject or clothes the subject is wearing;

analyzing the parameter to generate a measure of blood pressure change of the subject over an inspiration/expiration cycle;

comparing the measure of blood pressure change to a threshold; and responsively to the measure being greater than the threshold, detecting the pulsus paradoxus.

In an embodiment, the at least one parameter includes at least one motion-related parameter of the subject, and sensing the at least one parameter includes sensing the at least one motion-related parameter.

There is still further provided, in accordance with an embodiment of the present invention, a method for predicting an onset of an asthma attack, including:

sensing at least one parameter of a subject without contacting or viewing the subject or clothes the subject is wearing; and predicting the onset of the asthma attack at least in part responsively to the sensed parameter.

In an embodiment, the at least one parameter includes at least one motion-related parameter of the subject, and sensing the at least one parameter includes sensing the at least one motion-related parameter.

For some applications, predicting the onset includes predicting the onset before the subject or a caretaker of the subject becomes aware of the onset.

For some applications, predicting the onset includes generating subject-specific data regarding the parameter by analyzing previous occurrences of the asthma attack, and predicting the onset at least in part responsively to the data.

For some applications, predicting the onset includes determining a measure of restlessness of the subject, and predicting the onset at least in part responsively to the measure of restlessness. Alternatively or additionally, the method includes determining a measure of coughing of the subject, and predicting the onset includes predicting the onset at least in part responsively to the sensed parameter and the measure of coughing.

In an embodiment, sensing the at least one parameter includes sensing the at least one parameter without requiring human compliance. For some applications, sensing the at least one parameter includes sensing the at least one parameter while the subject is sleeping. In an embodiment, the method includes alerting the subject to the predicted onset only after the subject awakes.

In an embodiment, the at least one parameter includes at least one breathing-related parameter of the subject, and sensing the at least one parameter includes sensing the at least one breathing-related parameter. For some applications, the at least one parameter includes at least one heartbeat-related parameter of the subject, sensing the at least one parameter includes sensing the at least one heartbeat-related parameter, and predicting the onset of the asthma attack includes predicting the onset of the asthma attack at least in part responsively to the breathing-related and the heartbeat-related parameters.

For some applications, predicting the onset includes determining at least one breathing pattern of the subject responsively to the sensed breathing-related parameter, comparing the breathing pattern with a baseline breathing pattern, and predicting the onset at least in part responsively to the comparison.

In an embodiment, sensing the at least one parameter includes measuring a pressure in, on, or under a reclining surface upon which the subject lies. For some applications, sensing the at least one parameter includes measuring the pressure using exactly one sensor placed in, on, or under the reclining surface.

There is additionally provided, in accordance with an embodiment of the present invention, a method for predicting an onset of an episode associated with congestive heart failure (CHF), including:

sensing at least one parameter of a subject without contacting or viewing the subject or clothes the subject is wearing; and predicting the onset of the episode at least in part responsively to the sensed parameter.

In an embodiment, the at least one parameter includes at least one motion-related parameter of the subject, and sensing the at least one parameter includes sensing the at least one motion-related parameter.

In an embodiment, sensing the at least one parameter includes measuring a pressure in, on, or under a reclining surface upon which the subject lies.

For some applications, sensing the at least one parameter includes sensing the at least one parameter while the subject is sleeping.

In an embodiment, sensing the at least one parameter includes sensing a breathing-related parameter of the subject, and a blood pressure of the subject, and predicting the onset includes predicting the onset at least in part responsively to the breathing-related parameter and the blood pressure. For some applications, sensing the at least one parameter includes sensing the at least one parameter without requiring human compliance.

There is still additionally provided, in accordance with an embodiment of the present invention, a method for predicting an onset of a clinical episode, including:

sensing at least one parameter of a subject; and while a breathing rate of the subject is less than 120% of a baseline asymptomatic breathing rate of the subject, predicting the onset of the clinical episode at least in part responsively to the sensed parameter.

In an embodiment, sensing the at least one parameter includes sensing the at least one parameter without contacting or viewing the subject or clothes the subject is wearing.

In an embodiment, the clinical episode includes an asthma attack, and predicting the onset of the clinical episode includes predicting the onset of the asthma attack.

For some applications, predicting the onset includes predicting the onset while the breathing rate is less than 110% of the baseline asymptomatic breathing rate, such as less than 105% of the baseline asymptomatic breathing rate.

There is additionally provided, in accordance with an embodiment of the present invention, a method for predicting an onset of an asthma attack, including:

sensing at least one parameter of a subject; and while a forced expiratory volume in one second (FEV1) of the subject is greater than 90% of a baseline asymptomatic FEV1 of the subject, predicting the onset of the asthma attack at least in part responsively to the sensed parameter.

For some applications, sensing the at least one parameter includes sensing the at least one parameter without contacting or viewing the subject or clothes the subject is wearing.

There is also provided, in accordance with an embodiment of the present invention, a method for predicting an onset of a clinical episode, including:

sensing at least one parameter of a subject without contacting or viewing the subject or clothes the subject is wearing; and at least one hour prior to the onset of the clinical episode, predicting the onset at least in part responsively to the sensed parameter.

For some applications, sensing the at least one parameter includes sensing at least two parameters of the subject without contacting or viewing the subject or clothes the subject is wearing, and predicting the onset includes predicting the onset at least in part responsively to the sensed parameters.

For some applications, predicting the onset includes predicting the onset at least four hours prior to the onset.

For some applications, sensing the at least one parameter includes sensing the at least one parameter substantially continuously for a period having a duration of at least one hour.

For some applications, the clinical episode includes an asthma attack, and predicting the onset of the clinical episode includes predicting the onset of the asthma attack.

There is further provided, in accordance with an embodiment of the present invention, a method for predicting an onset of a clinical episode, including:

sensing at least one parameter of a subject substantially continuously during a period having a duration of at least one hour; and at least one hour prior to the onset of the clinical episode, predicting the onset at least in part responsively to the sensed parameter.

In an embodiment, sensing the at least one parameter includes sensing the at least one parameter without contacting or viewing the subject or clothes the subject is wearing.

For some applications, sensing the at least one parameter includes sensing at least two parameters of the subject substantially continuously during the period, and predicting the onset includes predicting the onset at least in part responsively to the sensed parameters.

In an embodiment, the clinical episode includes an asthma attack, and predicting the onset of the clinical episode includes predicting the onset of the asthma attack.

For some applications, predicting the onset includes predicting the onset at least four hours prior to the onset.

For some applications, the period has a duration of at least four hours, and sensing the at least one parameter includes sensing the at least one parameter substantially continuously during the period having the duration of at least four hours.

There is still further provided, in accordance with an embodiment of the present invention, a method for predicting an onset of a clinical episode, including:

sensing at least one parameter of a subject substantially continuously during at least 80% of a period of time a subject is sleeping at night; and at least in part responsively to the sensed parameter, predicting the onset of the clinical episode at least one hour prior to the onset.

For some applications, sensing the at least one parameter includes sensing at least two parameters of the subject substantially continuously during the 80% of the period, and predicting the onset includes predicting the onset at least in part responsively to the sensed parameters.

In an embodiment, the clinical episode includes an asthma attack, and predicting the onset of the clinical episode includes predicting the onset of the asthma attack.

In an embodiment, sensing the at least one parameter includes sensing the at least one parameter without contacting or viewing the subject or clothes the subject is wearing.

There is additionally provided, in accordance with an embodiment of the present invention, method including:

sensing at least one parameter of a subject; and at least in part responsively to the sensed parameter, calculating a probability that a clinical episode will occur within a predetermined period of time after the calculating.

For some applications, sensing the at least one parameter includes sensing at least two parameters of the subject, and calculating a probability includes calculating the probability at least in part responsively to the sensed parameters.

For some applications, the method includes notifying the subject if the probability exceeds a threshold value.

In an embodiment, the clinical episode includes an asthma attack, and predicting the onset of the clinical episode includes predicting the onset of the asthma attack.

In an embodiment, sensing the at least one parameter includes sensing the at least one parameter without contacting or viewing the subject or clothes the subject is wearing.

In an embodiment, calculating the probability includes calculating the probability at least in part responsively to data including a population-based average of the parameter. Alternatively or additionally, calculating the probability includes generating subject-specific data regarding the parameter by analyzing previous occurrences of the clinical episode, and calculating the probability at least in part responsively to the data.

There is still additionally provided, in accordance with an embodiment of the present invention, a method for predicting an onset of a clinical episode, including:

sensing at least one parameter of a subject without requiring human compliance; and predicting the onset at least in part responsively to the sensed parameter.

In an embodiment, sensing the at least one parameter includes sensing the at least one parameter without contacting or viewing the subject or clothes the subject is wearing.

In an embodiment, the at least one parameter includes at least one motion-related parameter of the subject, and sensing the at least one parameter includes sensing the at least one motion-related parameter without requiring human compliance.

For some applications, sensing the at least one parameter includes sensing the at least one parameter while the subject is sleeping, and including alerting the subject to the predicted onset only after the subject awakes.

For some applications, the subject is hospitalized, and the method includes alerting a healthcare worker upon the predicting.

For some applications, sensing the at least one parameter without requiring human compliance includes measuring a pressure in, on, or under a reclining surface upon which the subject lies.

In an embodiment, the clinical episode includes an asthma attack, and predicting the onset includes predicting the onset of the asthma attack. Alternatively, the clinical episode includes an episode associated with congestive heart failure (CHF) of the subject, and predicting the onset includes predicting the onset of the episode associated with the CHF. Further alternatively, the clinical episode includes an episode of hypoglycemia caused by diabetes, and predicting the onset includes predicting the onset of the episode of hypoglycemia. Still further alternatively, the clinical episode is selected from the list consisting of: an episode of abnormal autonomic nervous system activity caused by a neurological condition, an epileptic seizure, an episode of Periodic Limb Movements in Sleep (PLMS), a stroke, an episode of essential tremor, an episode of stress, an episode of fibrillation, an episode associated with chronic obstructive pulmonary disease (COPD), an episode associated with cystic fibrosis (CF), and an episode of anaphylactic shock, and predicting the onset includes predicting the onset of the selected clinical episode.

In an embodiment, the at least one parameter includes at least one breathing-related parameter of the subject, and sensing the at least one parameter includes sensing the at least one breathing-related parameter without requiring human compliance. For some applications, predicting the onset includes determining at least one breathing pattern of the subject responsively to the sensed breathing-related parameter, comparing the breathing pattern with a baseline breathing pattern, and predicting the onset at least in part responsively to the comparison.

There is additionally provided, in accordance with an embodiment of the present invention, apparatus including:

a non-contact sensor, adapted to sense a motion-related parameter of a subject without contacting the subject or clothes the subject is wearing; and a control unit, adapted to:

derive heartbeat- and breathing-related signals from the motion-related parameter, and demodulate the heartbeat-related signal using the breathing-related signal.

There is also provided, in accordance with an embodiment of the present invention, apparatus for measuring a heartbeat of a fetus in a pregnant subject, including:

a non-contact sensor, adapted to sense a motion-related parameter of the pregnant subject without contacting the subject or clothes the subject is wearing; and a control unit, adapted to derive the fetal heartbeat from the motion-related parameter.

There is further provided, in accordance with an embodiment of the present invention, apparatus for monitoring movement of a fetus in a pregnant subject, including:

a non-contact sensor, adapted to sense a motion-related parameter of the pregnant subject without contacting the subject or clothes the subject is wearing; and a control unit, adapted to derive a measure of motion of the fetus from the motion-related parameter.

There is still further provided, in accordance with an embodiment of the present invention, apparatus including:

a sensor, adapted to sense at least one parameter of a subject while the subject sleeps;

a user interface; and a control unit, adapted to:

analyze the parameter, predict an onset of a clinical episode at least in part responsively to the analysis, and drive the user interface to alert the subject to the predicted onset only after the subject awakes.

There is additionally provided, in accordance with an embodiment of the present invention, apparatus for predicting an onset of a clinical episode, including:

a sensor, adapted to acquire a breathing-related time-domain signal of a subject; and a control unit, adapted to:

transform the time-domain signal into a frequency-domain signal, determine a breathing rate of the subject by identifying a peak in a breathing-related frequency range of the frequency-domain signal, determine one or more harmonics of the peak frequency, determine a relationship between:

(a) a first energy level, selected from the list consisting of: an energy level associated with one of the one or more harmonics, and an energy level associated with a frequency of the peak, and (b) a second energy level, associated with one of the one or more harmonics;

compare the relationship with a baseline level of the relationship, and predict the onset of the episode at least in part responsively to the comparison.

There is still additionally provided, in accordance with an embodiment of the present invention, apparatus for monitoring blood pressure, including:

a non-contact sensor, adapted to sense a motion-related parameter of a subject without contacting the subject or clothes the subject is wearing; and a control unit, adapted to analyze the parameter to determine a measure of blood pressure of the subject.

There is additionally provided, in accordance with an embodiment of the present invention, apparatus for treating a subject, including:

a non-contact sensor, adapted to sense a motion-related parameter of a subject without contacting the subject or clothes the subject is wearing;

a drug administration device, adapted to administer a drug to the subject; and a control unit, adapted to:

analyze the parameter, responsively at least in part to the analysis, determine an initial dosage of the drug, and communicate the initial dosage to the drug administration device.

There is also provided, in accordance with an embodiment of the present invention, apparatus for predicting an onset of a clinical episode, including:

a sensor, adapted to sense at least one parameter of a subject; and a control unit, adapted to:

analyze the parameter, receive data regarding a drug administered to the subject, and predict the onset of a clinical episode at least in part responsively to the analysis and the drug administration data in combination.

For some applications, the apparatus includes a drug administration device adapted to administer the drug to the subject, and the control unit is adapted to receive the drug administration data from the drug administration device.

There is further provided, in accordance with an embodiment of the present invention, apparatus for treating a clinical episode, including:

a non-contact sensor, adapted to sense at least one parameter of a subject without contacting the subject or clothes the subject is wearing;

a treatment device, adapted to be implanted in the subject; and a control unit, adapted to:

analyze the parameter, detect the clinical episode at least in part responsively to the analysis, and responsively to detecting the clinical episode, drive the treatment device to treat the clinical episode.

There is still further provided, in accordance with an embodiment of the present invention, apparatus including:

a non-contact sensor, adapted to sense at least one parameter of a subject while the subject sleeps, without contacting the subject or clothes the subject is wearing; and a control unit, adapted to analyze the parameter to determine a measure of restlessness of the subject.

There is additionally provided, in accordance with an embodiment of the present invention, apparatus including:

a non-contact sensor, adapted to sense at least one parameter of a subject while the subject sleeps, without contacting the subject or clothes the subject is wearing; and a control unit, adapted to detect Periodic Limb Movements in Sleep (PLMS) of the subject by analyzing the parameter.

There is still additionally provided, in accordance with an embodiment of the present invention, apparatus including:

exactly one non-contact sensor, adapted to be placed in or under a reclining surface upon which the subject lies such that the sensor is not in contact with the subject or clothes the subject is wearing, and to sense at least one parameter of a subject; and a control unit, adapted to detect coughing of the subject by analyzing the parameter.

There is additionally provided, in accordance with an embodiment of the present invention, apparatus for predicting an onset of an asthma attack, including:

a sensor, adapted to sense breathing of a subject and a heartbeat of the subject; and a control unit, adapted to:

determine at least one breathing pattern of the subject responsively to the sensed breathing, and at least one heart pattern of the subject responsively to the sensed heartbeat, compare the breathing pattern with a baseline breathing pattern, and the heart pattern with a baseline heart pattern, and predict the onset of the asthma attack at least in part responsively to the comparisons.

For some applications, the sensor includes a first sensor, adapted to sense the breathing, and a second sensor, adapted to sense the heartbeat.

There is also provided, in accordance with an embodiment of the present invention, apparatus for predicting an onset of an asthma attack, including:

a sensor, adapted to sense breathing of a subject; and a control unit, adapted to:

determine at least one breathing pattern of the subject responsively to the sensed breathing, compare the breathing pattern with a baseline breathing pattern, determine a measure of coughing of the subject, and predict the onset of the asthma attack at least in part responsively to the comparison and the measure of coughing.

There is further provided, in accordance with an embodiment of the present invention, apparatus for predicting an onset of an episode associated with congestive heart failure (CHF), including:

a sensor, adapted to sense breathing of a subject and a blood pressure of the subject; and a control unit, adapted to:

determine at least one breathing pattern of the subject responsively to the sensed breathing, compare the breathing pattern with a baseline breathing pattern, and predict the onset of the episode at least in part responsively to the comparison and the blood pressure.

For some applications, the sensor includes a first sensor, adapted to sense the breathing, and a second sensor, adapted to sense the blood pressure.

There is still further provided, in accordance with an embodiment of the present invention, apparatus for determining a heart rate of a subject, including:

a first non-contact sensor, adapted to sense a first pulse signal of the subject in a vicinity of a first location of the subject selected from: a chest of the subject, and an abdomen of the subject;

a second non-contact sensor, adapted to sense a second pulse signal of the subject in a vicinity of a second location of the subject anatomically below a waist of the subject; and a control unit, adapted to determine the heart rate responsively to the first and second pulse signals.

There is additionally provided, in accordance with an embodiment of the present invention, apparatus including:

a first sensor and a second sensor, adapted to sense first and second motion-related parameters of a subject in a vicinity of a first site and in a vicinity of a second site of the subject, respectively, without contacting the subject or clothes the subject is wearing; and a control unit, adapted to:

derive first and second breathing-related signals from the first and second motion-related parameters, respectively, and analyze the first and second breathing-related signals to determine a measure of thoracoabdominal asynchrony (TAA) of the subject.

There is still additionally provided, in accordance with an embodiment of the present invention, apparatus including:

a first sensor and a second sensor, adapted to sense first and second motion-related parameters of a subject in a vicinity of a first site and in a vicinity of a second site of the subject, respectively, without contacting the subject or clothes the subject is wearing; and a control unit, adapted to:

derive first and second breathing-related signals from the first and second motion-related parameters, respectively, and analyze the first and second breathing-related signals to determine a measure of accessory muscle activity of the subject.

There is additionally provided, in accordance with an embodiment of the present invention, apparatus for monitoring a subject, including:

a non-contact sensor, adapted to sense at least one parameter of a subject without contacting the subject or clothes the subject is wearing;

a user interface; and a control unit, adapted to:

set respective first and second thresholds that are different, analyze the parameter to generate a score, if the score is between the first and second thresholds, drive the user interface to generate a first output indicative of a predicted onset of a clinical episode, and if the score passes the second threshold, drive the user interface to generate a second output indicative of a currently occurring clinical episode.

There is also provided, in accordance with an embodiment of the present invention, apparatus for detecting pulsus paradoxus of a subject, including:

a non-contact sensor, adapted to sense at least one parameter of a subject without contacting the subject or clothes the subject is wearing; and a control unit, adapted to:

analyze the parameter to generate a measure of blood pressure change of the subject over an inspiration/expiration cycle, compare the measure of blood pressure change to a threshold, and responsively to the measure being greater than the threshold, detect the pulsus paradoxus.

There is further provided, in accordance with an embodiment of the present invention, apparatus for predicting an onset of an asthma attack, including:

a non-contact sensor, adapted to sense at least one parameter of a subject without contacting the subject or clothes the subject is wearing; and a control unit, adapted to predict the onset of the asthma attack at least in part responsively to the sensed parameter.

For some applications, the apparatus include a user interface, and the control unit is adapted to drive the user interface to alert the subject to the predicted onset only after the subject awakes.

For some applications, the sensor includes a pressure gauge, configured to measure a pressure in, on, or under a reclining surface upon which the subject lies. For some applications, the pressure gauge includes exactly one pressure gauge.

There is still further provided, in accordance with an embodiment of the present invention, apparatus for predicting an onset of an episode associated with congestive heart failure (CHF), including:

a non-contact sensor, adapted to sense at least one parameter of a subject without contacting the subject or clothes the subject is wearing; and a control unit, adapted to predict the onset of the episode at least in part responsively to the sensed parameter.

For some applications, the sensor includes a pressure gauge, configured to measure a pressure in, on, or under a reclining surface upon which the subject lies.

There is additionally provided, in accordance with an embodiment of the present invention, apparatus for predicting an onset of a clinical episode, including:

a sensor, adapted to sense at least one parameter of a subject; and a control unit, adapted to predict, while a breathing rate of the subject is less than 120% of a baseline asymptomatic breathing rate of the subject, the onset of the clinical episode at least in part responsively to the sensed parameter.

There is still additionally provided, in accordance with an embodiment of the present invention, apparatus for predicting an onset of an asthma attack, including:

a sensor, adapted to sense at least one parameter of a subject; and a control unit, adapted to predict, while a forced expiratory volume in one second (FEV1) of the subject is greater than 90% of a baseline asymptomatic FEV1 of the subject, the onset of the asthma attack at least in part responsively to the sensed parameter.

There is additionally provided, in accordance with an embodiment of the present invention, apparatus for predicting an onset of a clinical episode, including:

a non-contact sensor, adapted to sense at least one parameter of a subject without contacting the subject or clothes the subject is wearing; and a control unit, adapted to predict, at least one hour prior to the onset of the clinical episode, the onset at least in part responsively to the sensed parameter.

There is also provided, in accordance with an embodiment of the present invention, apparatus for predicting an onset of a clinical episode, including:

a sensor, adapted to sense at least one parameter of a subject substantially continuously during a period having a duration of at least one hour; and a control unit, adapted to predict, at least one hour prior to the onset of the clinical episode, the onset at least in part responsively to the sensed parameter.

There is further provided, in accordance with an embodiment of the present invention, apparatus for predicting an onset of a clinical episode, including:

a sensor, adapted to sense at least one parameter of a subject substantially continuously during at least 80% of a period of time a subject is sleeping at night; and a control unit, adapted to predict, at least one hour prior to the onset, the onset of the clinical episode at least in part responsively to the sensed parameter.

There is still further provided, in accordance with an embodiment of the present invention, apparatus including:

a sensor, adapted to sense at least one parameter of a subject; and a control unit, adapted to calculate, at least in part responsively to the sensed parameter, a probability that a clinical episode will occur within a predetermined period of time after the calculating.

There is further provided, in accordance with an embodiment of the present invention, apparatus for predicting an onset of a clinical episode, including:

a sensor, adapted to sense at least one parameter of a subject without requiring human compliance; and a control unit, adapted to predict the onset at least in part responsively to the sensed parameter.

In an embodiment, the sensor includes a non-contact sensor, adapted to sense the at least one parameter without contacting the subject or clothes the subject is wearing.

For some applications, the sensor is adapted to sense the at least one parameter while the subject is sleeping, the apparatus includes a user interface, and the control unit is adapted to drive the user interface to alert the subject to the predicted onset only after the subject awakes.

For some applications, the sensor includes a pressure gauge, configured to measure a pressure in, on, or under a reclining surface upon which the subject lies.

In some embodiments of the present invention, the apparatuses described hereinabove are adapted to perform one or more of the methods described hereinabove, as appropriate. For example, the control unit of the apparatuses may be adapted to carry out one or more steps of the methods (such as analytical steps), and/or the sensor of the apparatuses may be adapted to carry out one or more of the sensing steps of the methods.

The present invention will be more fully understood from the following detailed description of embodiments thereof, taken together with the drawings, in which:

BRIEF DESCRIPTION OF THE DRAWINGS

FIGS. 8A-B are graphs showing different frequency components of a motion signal, in accordance with an embodiment of the present invention;

FIG. 9 includes graphs showing several signals in time and corresponding frequency domains, in accordance with an embodiment of the present invention;

FIGS. 10A-C are graphs showing frequency spectra, measured in accordance with an embodiment of the present invention;

FIG. 12 is a graph showing body movement, in accordance with an embodiment of the present invention;

FIG. 13 is a graph showing restlessness events during normal sleep and during a clinical episode of asthma, in accordance with an embodiment of the present invention;

FIGS. 14A-B are graphs showing power spectrum densities of signals measured in accordance with an embodiment of the present invention;

FIG. 15 is a schematic illustration of a configuration of the system of FIG. 1 comprising two motion sensors, in accordance with an embodiment of the present invention;

FIGS. 16A-B are graphs showing pulse signals measured simultaneously under the legs and abdomen of a subject, and the cross correlation between the signals of FIG. 16A, respectively, as measured and calculated in accordance with an embodiment of the present invention;

FIG. 17 is a schematic illustration of the system of FIG. 1 adapted to monitor a pregnant subject and her fetus, in accordance with an embodiment of the present invention;

FIG. 19 is a graph illustrating an exemplary power spectrum used for carrying out the method described with reference to FIG. 18, in accordance with an embodiment of the present invention;

FIG. 20 is a graph showing the ratio of two harmonics of a respiration signal of an asthma patient, measured in accordance with an embodiment of the present invention;

DETAILED DESCRIPTION OF EMBODIMENTS

Figure 1:
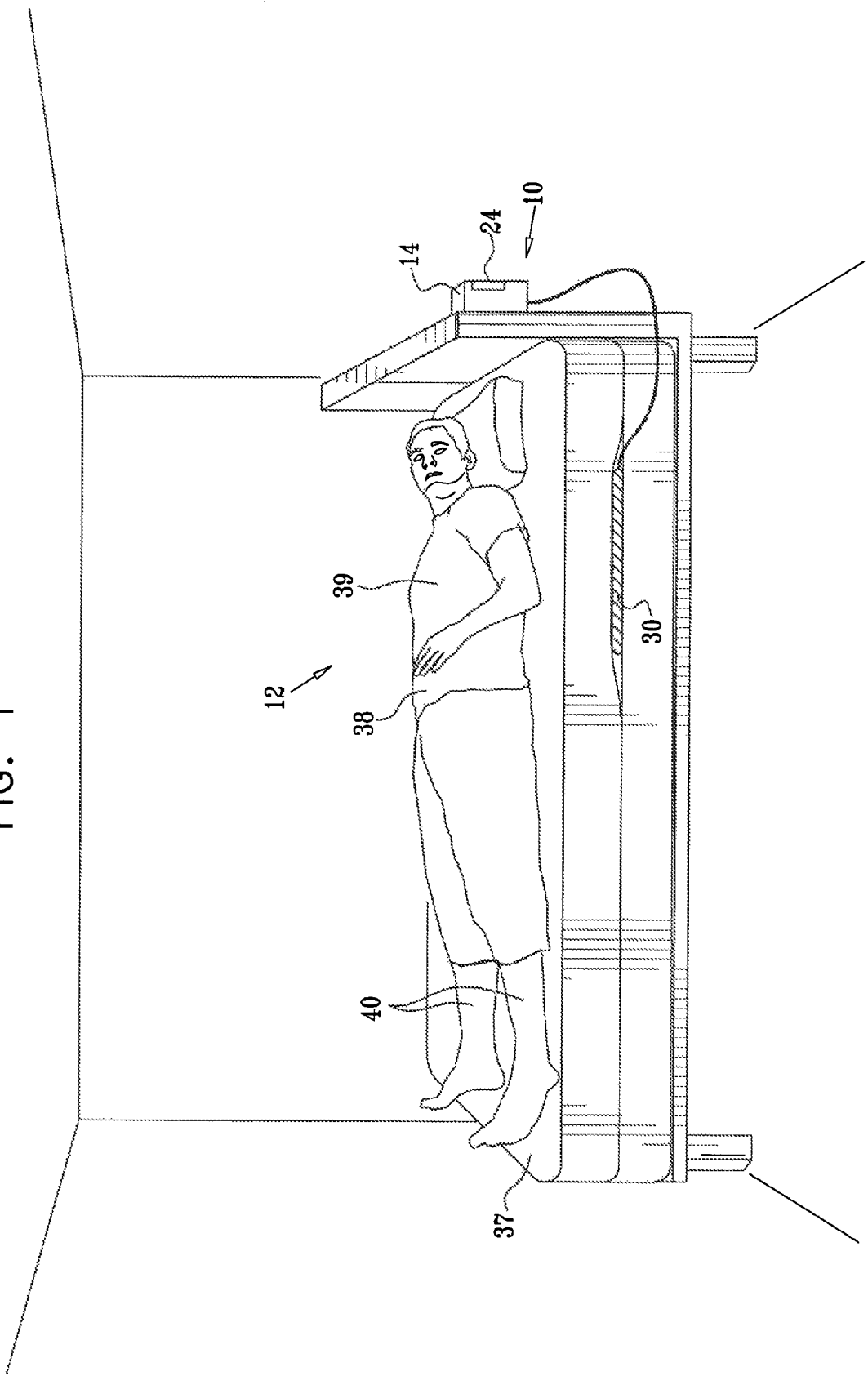
FIG. 1 is a schematic illustration of a system for monitoring a chronic medical condition of a subject, in accordance with an embodiment of the present invention.

FIG. 1 is a schematic illustration of a system 10 for monitoring a chronic medical condition of a subject 12, in accordance with an embodiment of the present invention. System 10 typically comprises a motion sensor 30, a control unit 14, and a user interface 24. For some applications, user interface 24 is integrated into control unit 14, as shown in the figure, while for other applications, the user interface and control unit are separate units. For some applications, motion sensor 30 is integrated into control unit 14, in which case user interface 24 is either also integrated into control unit 14 or remote from control unit 14.

Figure 2:
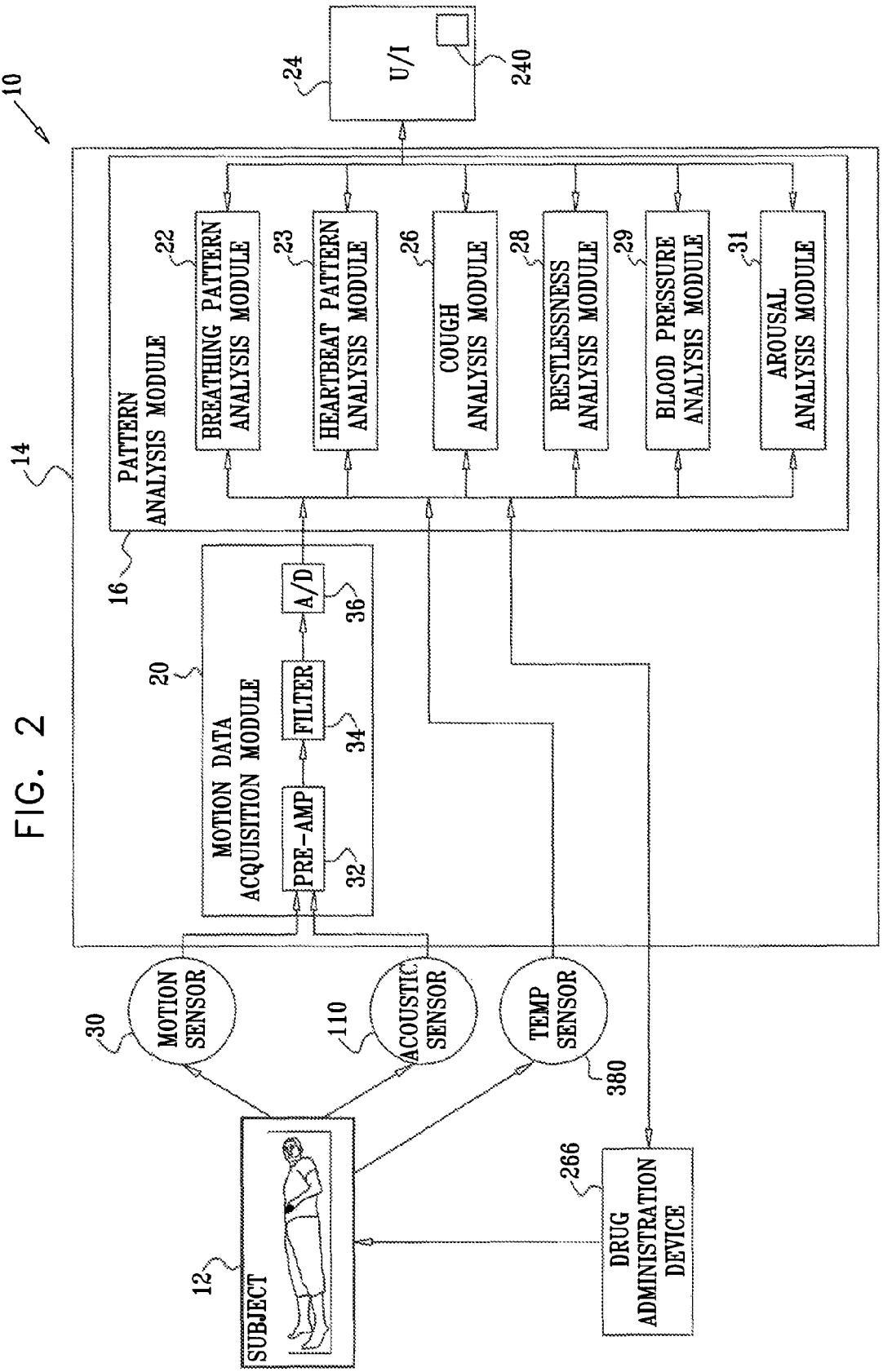
FIG. 2 is a schematic block diagram illustrating components of control unit of the system of FIG. 1, in accordance with an embodiment of the present invention.

FIG. 2 is a schematic block diagram illustrating components of control unit 14, in accordance with an embodiment of the present invention. Control unit 14 typically comprises a motion data acquisition module 20 and a pattern analysis module 16. Pattern analysis module 16 typically comprises one or more of the following modules: a breathing pattern analysis module 22, a heartbeat pattern analysis module 23, a cough analysis module 26, a restlessness analysis module 28, a blood pressure analysis module 29, and an arousal analysis module 31. For some applications, two or more of analysis modules 20, 22, 23, 26, 28, 29, and 31 are packaged in a single housing. For other applications, the modules are packaged separately (for example, so as to enable remote analysis by one or more of the pattern analysis modules of breathing signals acquired locally by data acquisition module 20). For some applications, user interface 24 comprises a dedicated display unit such as an LCD or CRT monitor. Alternatively or additionally, user interface 24 includes a communication line for relaying the raw and/or processed data to a remote site for further analysis and/or interpretation.

In an embodiment of the present invention, data acquisition module 20 is adapted to non-invasively monitor breathing and heartbeat patterns of subject 12. Breathing pattern analysis module 22 and heartbeat pattern analysis module 23 are adapted to analyze the respective patterns in order to (a) predict an approaching clinical episode, such as an asthma attack or heart condition-related lung fluid buildup, and/or (b) monitor the severity and progression of a clinical episode as it occurs. User interface 24 is adapted to notify subject 12 and/or a healthcare worker of the predicted or occurring episode. Prediction of an approaching clinical episode facilitates early preventive treatment, which generally reduces the required dosage of medication, and/or lowers mortality and morbidity. When treating asthma, such a reduced dosage generally minimizes the side-effects associated with high dosages typically required to reverse the inflammatory condition once the episode has begun.

In an embodiment of the present invention, pattern analysis module 16 combines parameter data generated from two or more of analysis modules 20, 22, 23, 26, 28, 29, and analyzes the combined data in order to predict and/or monitor a clinical event. For some applications, pattern analysis module 16 derives a score for each parameter based on the parameter's deviation from baseline values (either for the specific patient or based on population averages). Pattern analysis module 16 combines the scores, such as by taking an average, maximum, standard deviation, or other function of the scores. The combined score is compared to one or more threshold values (which may be predetermined) to determine whether an episode is predicted, currently occurring, or neither predicted nor occurring, and/or to monitor the severity and progression of an occurring episode. For some applications, pattern analysis module 16 learns the criteria and/or functions for combining the individual parameter scores for the specific patient or patient group based on personal history. For example, pattern analysis module 16 may perform such learning by analyzing parameters measured prior to previous clinical events.

Although system 10 may monitor breathing and heartbeat patterns at any time, for some conditions it is generally most effective to monitor such patterns during sleep at night. When the subject is awake, physical and mental activities unrelated to the monitored condition often affect breathing and heartbeat patterns. Such unrelated activities generally have less influence during most night sleep. For some applications, system 10 monitors and records patterns throughout all or a large portion of a night. The resulting data set generally encompasses typical long-term respiratory and heartbeat patterns, and facilitates comprehensive analysis. Additionally, such a large data set enables rejection of segments contaminated with movement or other artifacts, while retaining sufficient data for a statistically significant analysis.

Reference is again made to FIG. 2. Data acquisition module 20 typically comprises circuitry for processing the raw motion signal generated by motion sensor 30, such as at least one pre-amplifier 32, at least one filter 34, and an analog-todigital (A/D) converter 36. Filter 34 typically comprises a band-pass filter or a low-pass filter, serving as an anti-aliasing filter with a cut-off frequency of less than one half of the sampling rate. The low-passed data is typically digitized at a sampling rate of at least 10 Hz and stored in memory. For example, the anti-aliasing filter cut-off may be set to 5 Hz and the sampling rate set to 40 Hz.

Reference is again made to FIG. 1. In an embodiment of the present invention, motion sensor 30 comprises a pressure gauge (e.g., a piezoelectric sensor) or a strain gauge (e.g., a silicon or other semiconductor strain gauge, or a metallic strain gauge), which is typically adapted to be installed in, on, or under a reclining surface 37 upon which the subject lies, e.g., sleeps, and to sense breathing- and heartbeat-related motion of the subject. "Pressure gauge," as used in the claims, includes, but is not limited to, all of the gauges mentioned in the previous sentence. Typically, reclining surface 37 comprises a mattress, a mattress covering, a sheet, a mattress pad, and/or a mattress cover. For some applications, motion sensor 30 is integrated into reclining surface 37, e.g., into a mattress, and the motion sensor and reclining surface are provided together as an integrated unit. For some applications, motion sensor 30 is adapted to be installed in, on, or under reclining surface 37 in a vicinity of an abdomen 38 or chest 39 of subject 12. Alternatively or additionally, motion sensor 30 is installed in, on, or under reclining surface 37 in a vicinity of a portion of subject 12 anatomically below a waist of the subject, such as in a vicinity of legs 40 of the subject. For some applications, such positioning provides a clearer pulse signal than positioning the sensor in a vicinity of abdomen 38 or chest 39 of the subject. For some applications, motion sensor 30 comprises a fiber optic sensor, for example as described by Butter and Hocker in Applied Optics 17: 2867-2869 (Sep. 15, 1978).

For some applications, the pressure or strain gauge is encapsulated in a rigid compartment, which typically has a surface area of at least 10 cm^2, and a thickness of less than 5 mm. The gauge output is channeled to an electronic amplifier, such as a charge amplifier typically used with piezoelectric accelerometers and capacitive transducers to condition the extremely high output impedance of the transducer to a low impedance voltage suitable for transmission over long cables. The strain gauge and electronic amplifier translate the mechanical vibrations into electrical signals. Alternatively, the strain gauge output is amplified using a Wheatstone bridge and an amplifier such as Analog Device Module Numbers 3B16, for a minimal bandwidth, or 3B18, for a wider bandwidth (National Instruments Corporation, Austin, Tex., USA).

In an embodiment of the present invention, motion sensor 30 comprises a grid of multiple pressure or strain gauge sensors, adapted to be installed in, on, or under reclining surface 37. The use of such a grid, rather than a single gauge, may improve breathing and heartbeat signal reception.

Breathing pattern analysis module 22 is adapted to extract breathing patterns from the motion data, as described hereinbelow with reference to FIG. 3, and heartbeat pattern analysis module 23 is adapted to extract heartbeat patterns from the motion data. Alternatively or additionally, system 10 comprises another type of sensor, such as an acoustic or air-flow sensor, attached or directed at the subject's face, neck, chest and/or back.

Figure 3:
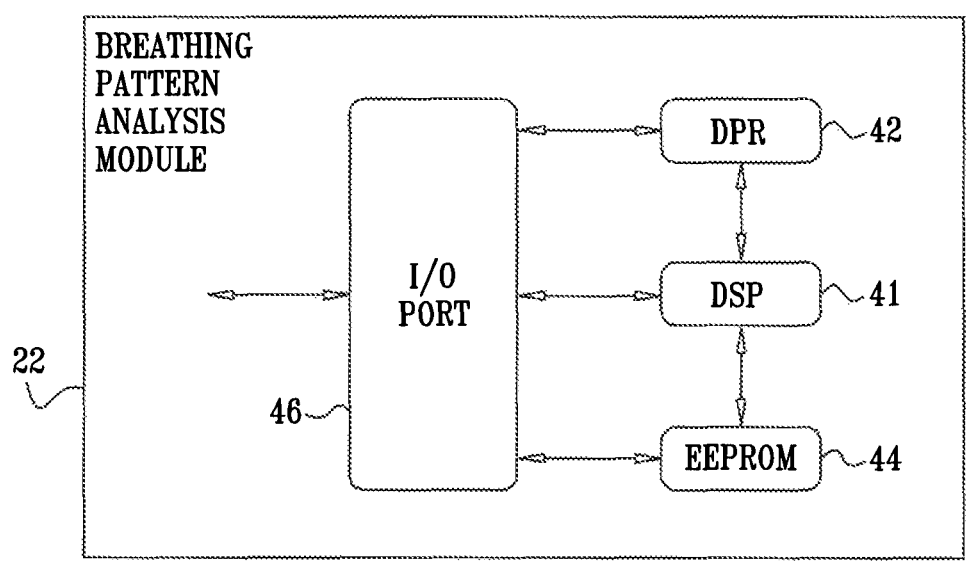
FIG. 3 is a schematic block diagram illustrating a breathing pattern analysis module of the control unit of FIG. 2, in accordance with an embodiment of the present invention.

FIG. 3 is a schematic block diagram illustrating breathing pattern analysis module 22, in accordance with an embodiment of the present invention. Breathing pattern analysis module 22 typically comprises a digital signal processor (DSP) 41, dual port RAM (DPR) 42, EEPROM 44, and an I/O port 46. Breathing pattern analysis module 22 is adapted to extract breathing patterns from the raw data generated by data acquisition module 20, and to perform processing and classification of the breathing patterns. Breathing pattern analysis module 22 analyzes changes in breathing patterns, typically during sleep. Responsively to the analysis, module 22 (a) predicts an approaching clinical episode, and/or (b) monitors episode severity and progression.

Reference is again made to FIG. 1. User interface 24 typically comprises a dedicated display unit, such as an LCD or CRT monitor. Alternatively or additionally, the output module comprises a wireless or wired communication port for relaying the acquired raw data and/or processed data to a remote site for further analysis, interpretation, expert review, and/or clinical follow-up. For example, the data may be transferred over a telephone line, and/or over the Internet or another wide-area network, either wirelessly or via wires.

Figure 4:
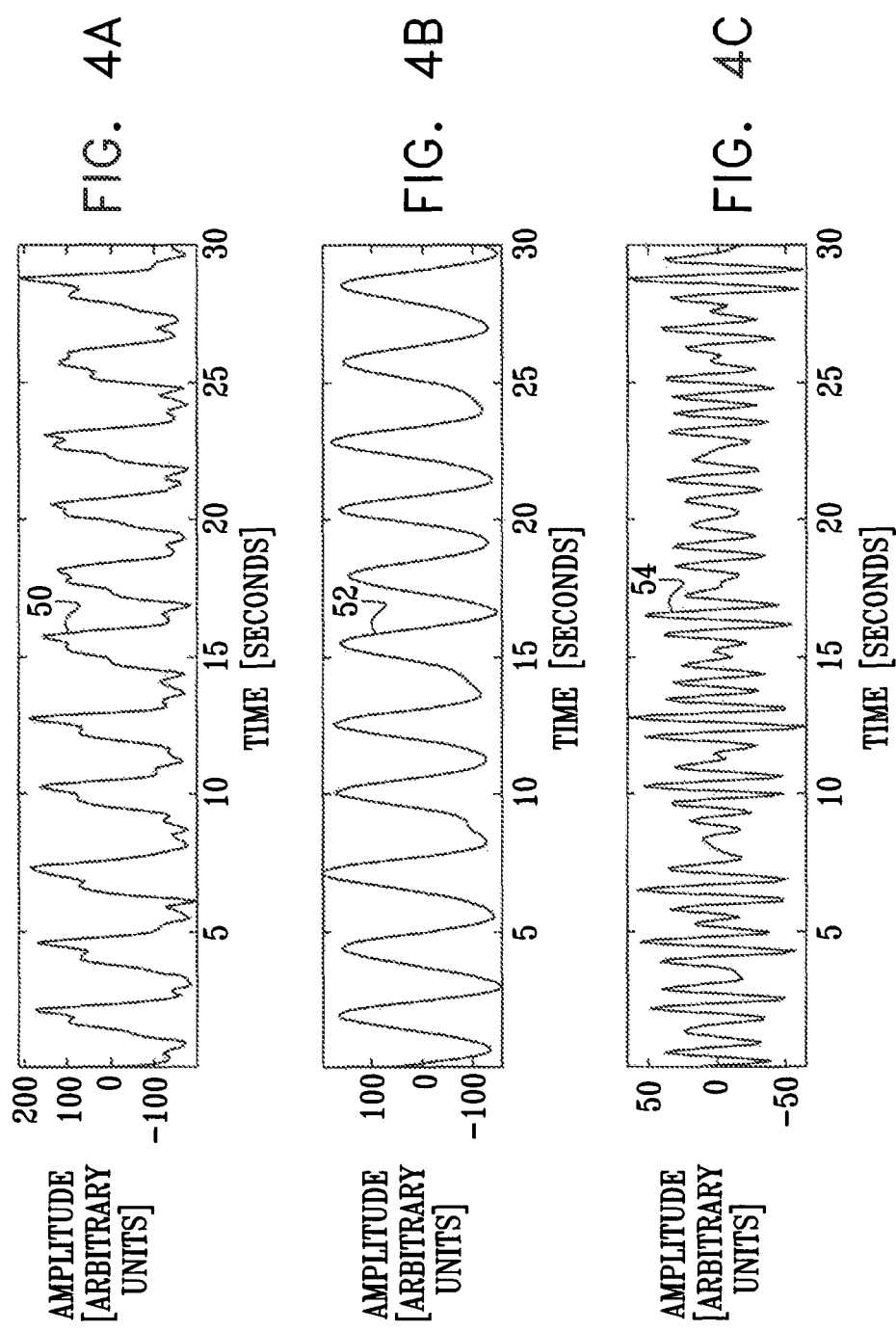
FIGS. 4A-C are graphs illustrating the analysis of motion signals, measured in accordance with an embodiment of the present invention.

Reference is made to FIGS. 4A-C, which are graphs illustrating the analysis of motion signals, measured in accordance with an embodiment of the present invention. As mentioned above, in an embodiment, motion sensor 30 comprises a pressure or strain gauge adapted to be installed under reclining surface 37, and to sense motion of subject 12. Motion of the subject during sleep includes regular breathing movement, heartbeat-related movement, and other, unrelated body movements, as discussed below. FIG. 4A shows raw mechanical signal 50 as measured by a piezoelectric strain gauge sensor under a mattress, including the combined contributions of breathing- and heartbeat-related signals. Signal 50 was decomposed into a breathing-related component 52, shown in FIG. 4B, and a heartbeat-related component 54, shown in FIG. 4C, using techniques described hereinbelow. All experimental results presented in the present application were measured using one or more piezoelectric sensors (nevertheless, the scope of the present invention includes performing measurements with other motion sensors 30, such as other pressure gauges, as described hereinabove with reference to FIG. 1).

Reference is again made to FIG. 2. For some applications, filter 34 comprises a band-pass filter having a low cutoff frequency between about 0.03 Hz and about 0.2 Hz, e.g., about 0.05 Hz, and a high cutoff frequency between about 1 Hz and about 10 Hz, e.g., about 5 Hz. Alternatively or additionally, the output of motion sensor 30 is channeled through several signal-conditioning channels, each with its own gain and filtering settings tuned according to the desired signal. For example, for breathing signals, a relatively low gain and a frequency passband of up to about 5 Hz may be used, while for heartbeat signals, a moderate gain and a slightly higher frequency cutoff of about 10 Hz may be used. For some applications, motion sensor 30 is additionally used for registration of acoustic signals, for which a frequency passband of about 100 Hz to about 8 kHz is useful.

In an embodiment of the present invention, motion data acquisition module 20 extracts breathing-related signals by performing spectral filtering in the range of about 0.05 to about 0.8 Hz, and heartbeat-related signals by performing spectral filtering in the range of about 0.8 to 5.0 Hz. For some applications, motion data acquisition module 20 adapts the spectral filtering based on the age of subject 12. For example, small children typically have higher breathing and heart rates, and therefore spectral filtering is typically set more tightly to the higher end of the frequency ranges, such as between about 0.1 and about 0.8 Hz for breathing, and between about 1.2 and about 5 Hz for heartbeat. For adults, spectral filtering is typically set more tightly to the lower end of the frequency ranges, such as between about 0.05 and about 0.5 Hz for breathing, and between about 0.5 and 2.5 Hz for heartbeat.

For some applications, motion data acquisition module 20 extracts breathing rate and heart rate from the filtered signal using zero-crossings or power spectrum analyses.

As mentioned above, motion of the subject during sleep includes regular breathing-related and heartbeat-related movements as well as other, unrelated body movements. In general, breathing-related motion is the dominant contributor to body motion during sleep. Pattern analysis module 16 is adapted to substantially eliminate the portion of the motion signal received from motion data acquisition module 20 that represents motion unrelated to breathing and heartbeat. For example, the pattern analysis module may remove segments of the signal contaminated by non-breathing- and non-heartbeat-related motion. While breathing- and heartbeat-related motion is periodic, other motion is generally random and non-predictable. For some applications, the pattern analysis module eliminates the non-breathing- and non-heartbeat-related motion using frequency-domain spectral analysis or time-domain regression analysis. Techniques for applying these analysis techniques will be evident to those skilled in art who have read the present application. For some applications, pattern analysis module 16 uses statistical methods, such as linear prediction or outlier analysis, to remove non-breathing-related and non-heartbeat-related motion from the signal. Motion data acquisition module 20 typically digitizes the motion data at a sampling rate of at least 10 Hz, although lower frequencies are suitable for some applications.

Figure 5:
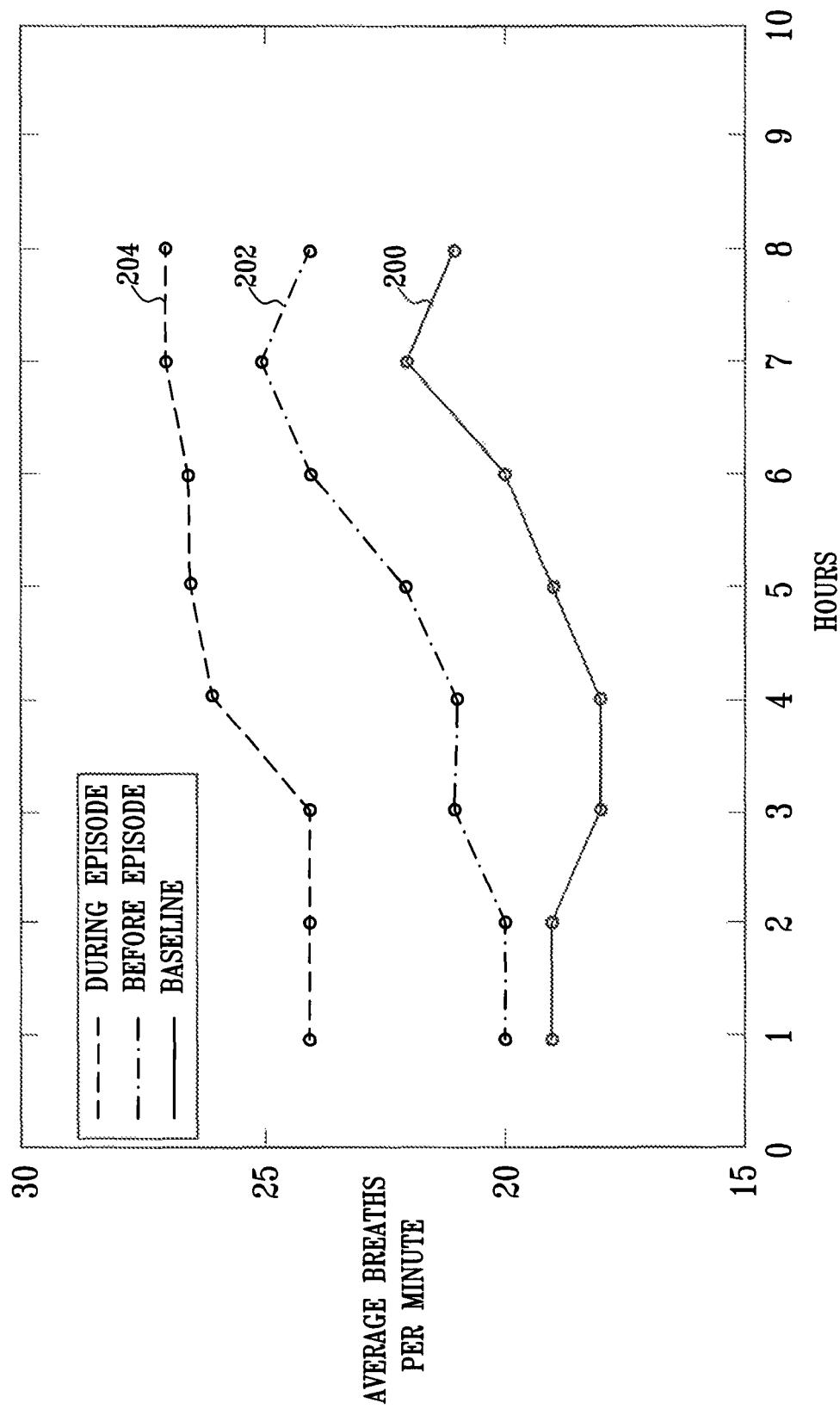
FIG. 5 is a graph illustrating breathing rate patterns of a chronic asthma patient, measured during an experiment conducted in accordance with an embodiment of the present invention.

Breathing pattern analysis module 22 is typically adapted to extract breathing patterns from a train of transient breathing pulses, each pulse including one inhalation-exhalation cycle. Breathing patterns during night sleep generally fall into one of several categories, including:

- relatively fast-changing, random breathing patterns, which occur mainly during REM sleep;
- cyclic breathing rate variability patterns, whose typical duration ranges from several seconds to several minutes, e.g. Cheyne-Stokes Respiration (CSR) or periodic breathing;
- slow trends in breathing rates (typically, during normal sleep of a healthy subject, such slow trends include segmented, substantially monotonically declining breathing rates usually lasting several hours; for subjects suffering chronically from certain conditions, such as asthma, the monotonic decline may be less pronounced or absent, as discussed, for example, hereinbelow with reference to FIG. 5);
- interruptions in breathing patterns such as coughing and other sleep disturbances; and
- interruptions in breathing patterns caused by momentary waking.

These breathing patterns are associated with various physiological parameters, such as sleep-stage, anxiety, and body temperature. For example, REM sleep is usually accompanied by randomly variable breathing patterns, while deep sleep stages are usually accompanied by more regular and stable patterns. Abnormally high body temperature may accelerate breathing rate, but usually maintains normal cyclic breathing rate variability patterns. Psychological variables such as anxiety are also modulators of breathing patterns during sleep, yet their effect is normally reduced with sleep progression. Interruptions in breathing patterns such as coughing or that caused by momentary waking may be normal, associated with asthma, or associated with other unrelated pathology, and are assessed in context.

In an embodiment of the present invention, pattern analysis module 16 is configured to predict the onset of an asthma attack, and/or monitor its severity and progression. Pattern analysis modules 22 and 23 typically analyze changes in breathing rate patterns, breathing rate variability patterns, heart rate patterns, and/or heart rate variability patterns in combination to predict the onset of an asthma attack. For some applications, breathing and/or heart rates are extracted from the signal by computing the Fourier transform of the filtered signal, and finding the frequency corresponding to the highest spectral peak value within allowed ranges corresponding to breathing and heart rate, or by using a zero-crossing method, or by finding the peaks of the time-domain signal and averaging the inter-pulse time over one minute to find heart beats per minute. For some applications, such averaging is performed after removing outlying values.

Although breathing rate typically slightly increases prior to the onset of an attack, this increase alone is not always a specific marker of the onset of an attack. Therefore, in order to more accurately predict the onset of an attack, and monitor the severity and progression of an attack, in an embodiment of the present invention, breathing pattern analysis module 22 additionally analyzes changes in breathing rate variability patterns. For some applications, module 22 compares one or more of the following patterns to respective baseline patterns, and interprets a deviation from baseline as indicative of (a) the onset of an attack, and/or (b) the severity of an attack in progress:

- a slow trend breathing rate pattern. Module 22 interprets as indicative of an approaching or progressing attack an increase vs. baseline, for example, for generally healthy subjects, an attenuation of the typical segmented, monotonic decline of breathing rate typically over at least 1 hour, e.g., over at least 2, 3, or 4 hours, or the transformation of this decline into an increasing breathing rate pattern, depending on the severity of the attack;
- a breathing rate pattern. Module 22 interprets as indicative of an approaching or progressing attack an increase or lack of decrease in breathing rate during the first several hours of sleep, e.g., during the first 2, 3, or 4 hours of sleep.
- a breathing rate variability pattern. Module 22 interprets as indicative of an approaching or progressing attack a decrease in breathing rate variability. Such a decrease generally occurs as the onset of an episode approaches, and intensifies with the progression of shortness of breath during an attack;
- a breathing duty-cycle pattern. Module 22 interprets a substantial increase in the breathing duty-cycle as indicative of an approaching or progressing attack. Breathing duty-cycle patterns include, but are not limited to, inspirium time/total breath cycle time, expirium time/total breath cycle time, and (inspirium+expirium time)/total breath cycle time;
- a change in breathing rate pattern towards the end of night sleep (typically between about 3:00 A.M. and about 6:00 A.M.); and
- interruptions in breathing pattern such as caused by coughs, sleep disturbances, or waking. Module 22 quantifies these events, and determines their relevance to prediction of potential asthma attacks.

Pattern analysis modules 22 and 23 typically determine baseline patterns by analyzing breathing and/or heart rate patterns, respectively, of the subject during non-symptomatic nights. Alternatively or additionally, modules 22 and 23 are programmed with baseline patterns based on population averages. For some applications, such population averages are segmented by characteristic traits such as age, height, weight, and gender.

In an embodiment of the present invention, pattern analysis module 16 determines the onset of an attack, and/or the severity of an attack in progress, by comparing the measured breathing rate pattern to a baseline breathing rate pattern, and/or the measured heart rate pattern to a baseline heart rate pattern.

In an embodiment of the present invention, breathing pattern analysis module 22 passes the respiration rate pattern calculated for the subject's sleep time through a low pass filter (e.g., a Finite Impulse Response filter) to reduce short-term effects such as REM sleep. For some applications, heartbeat pattern analysis module 23 performs similar filtering on the heart rate data.

Reference is made to FIG. 5, which is a graph illustrating breathing rate patterns of a chronic asthma patient, measured during an experiment conducted in accordance with an embodiment of the present invention. Breathing of the asthma patient was monitored during sleep on several nights. The patient's breathing rate was averaged for each hour of sleep (excluding periods of rapid eye movement (REM) sleep, which were removed using a low pass filter, which reduces the short-term effect of REM sleep; alternatively, REM sleep is identified and removed from consideration). During the first approximately two months that the patient was monitored, the patient did not experience any episodes of asthma. A line 200 is representative of a typical slow trend breathing pattern recorded during this non-episodic period, and thus represents a baseline slow trend breathing rate pattern for this patient. It should be noted that, unlike the monotonic decline in breathing rate typically observed in non-asthmatic patients, the baseline breathing rate pattern of the chronically asthmatic patient of the experiment reflects an initial decline in breathing rate during the first few hours of sleep, followed by a gradual increase in breathing rate throughout most of the rest of the night.

Lines 202 and 204 were recorded on two successive nights at the conclusion of the approximately two-month period, line 202 on the first of these two nights, and line 204 on the second of these two nights. The patient experienced an episode of asthma during the second of these nights. Lines 202 and 204 thus represent a pre-episodic slow trend breathing rate pattern and an episodic slow trend breathing rate pattern, respectively. As can be seen in the graph, the patient's breathing rate was elevated by about 1-3 breaths per minute vs. baseline during all hours of the pre-episodic night, and was even further elevated vs. baseline during the episodic night.

Using techniques described herein, breathing pattern analysis module 22 compares the pattern of line 202 with the baseline pattern of line 200, in order to predict that the patient may experience an asthmatic episode. Module 22 compares the pattern of line 204 with the baseline pattern of line 200 in order to assess a progression of the asthmatic episode.

In an embodiment of the present invention, the deviation from baseline is defined as the cumulative deviation of the measured pattern from the baseline pattern. A threshold indicative of a clinical condition is set equal to a certain number of standard errors (e.g., one standard error). Alternatively or additionally, other measures of deviation between measured and baseline patterns are used, such as correlation coefficient, mean square error, maximal difference between the patterns, and the area between the patterns. Further alternatively or additionally, pattern analysis module 16 uses a weighted analysis emphasizing specific regions along the patterns, for example, by giving a double weight to the first two hours of sleep or the hours of 3:00-6:00 a.m.

Figure 6:
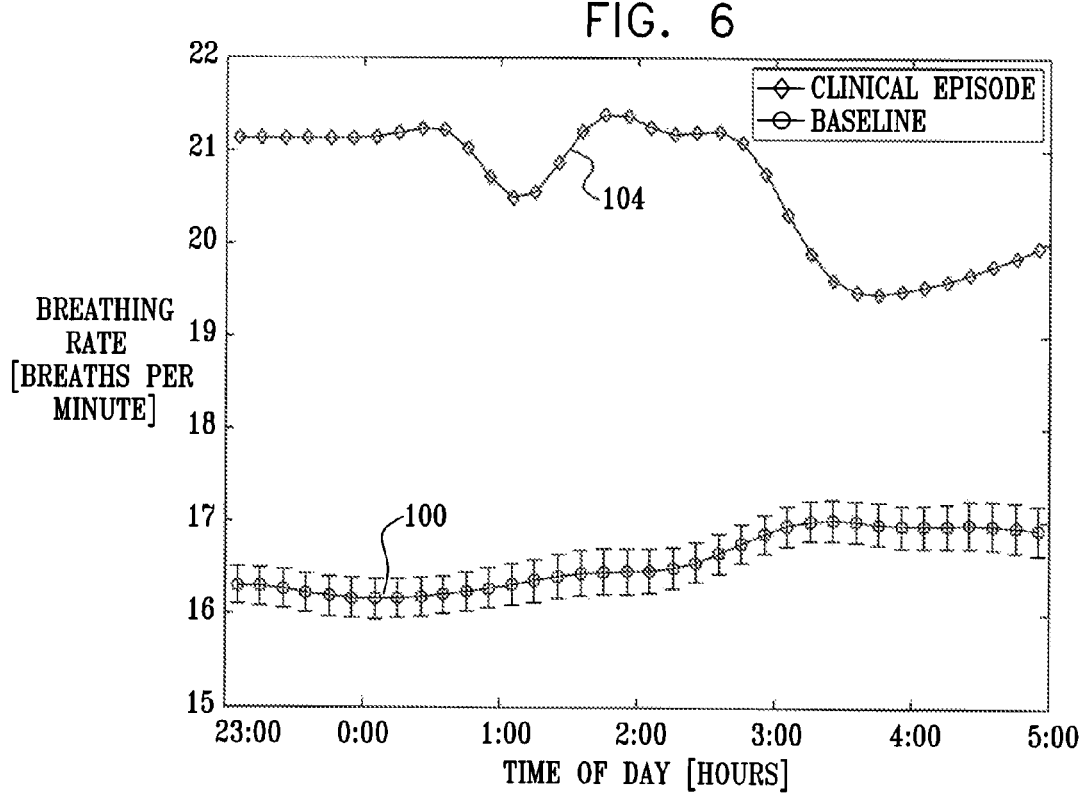
FIGS. 6 and 7 are graphs of exemplary baseline and measured breathing rate and heart rate nighttime patterns, respectively, measured in accordance with an embodiment of the present invention.
Figure 7:
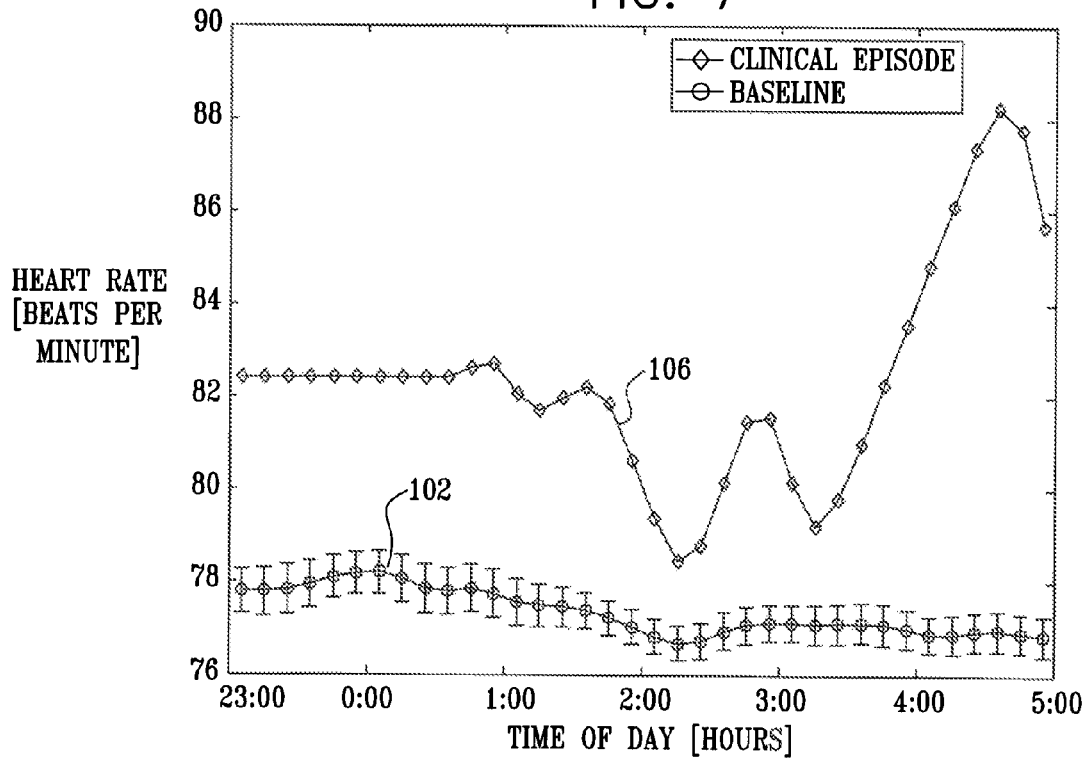

FIGS. 6 and 7 are graphs of exemplary baseline and measured breathing rate and heart rate nighttime patterns, respectively, measured in accordance with an embodiment of the present invention. Lines 100 and 102 (FIGS. 6 and 7, respectively) represent normal baseline patterns in the absence of an asthma attack. The bars represent one standard error. Lines 104 and 106 (FIGS. 6 and 7, respectively) represent patterns during nights prior to an onset of an asthma attack. Detection of the change in pattern between lines 100 and 102 and lines 104 and 106, respectively, enables the early prediction of the approaching asthma attack.

In an embodiment of the present invention, pattern analysis module 16 is configured to predict the onset of a clinical manifestation of heart failure, and/or monitor its severity and progression. Module 16 typically determines that an episode is imminent when the module detects increased breathing rate accompanied by increased heart rate, and/or when the monitored breathing and/or heartbeat patterns have specific characteristics that relate to heart failure, such as characteristics that are indicative of apnea, Cheyne-Stokes Respiration, and/or periodic breathing.

In an embodiment of the present invention, breathing cycles are divided into successive segments of inspirium and expirium. Breathing pattern analysis module 22 interprets as indicative of an approaching or progressing attack a trend towards greater duration of the expirium segments in proportion to the inspirium during sleep (typically night sleep). In another embodiment, the duty cycle of breathing activity (duration of expirium plus inspirium segments) vs. no respiratory motion is interpreted as an indicator of an approaching or progressing attack.

Reference is again made to FIG. 2. In an embodiment of the present invention, system 10 further comprises an acoustic sensor 110 for measurement of breathing-related sounds such as those caused by wheezing or coughing. (For some applications, in which breathing sensor 30 comprises a pressure gauge, acoustic sensor 110 is integrated with the pressure gauge. For example, a single sensor may be used for both acoustic sensing and measuring body motion. Alternatively, acoustic sensor 110 is a separate component.) Pattern analysis module 16 processes such breathing sounds independently, or time-locked to expirium and/or inspirium, e.g., by using spectral averaging to enhance the signal-to-noise ratio of wheezing sounds. For some applications, the level of wheezing and its timing with respect to the timing of inspirium and expirium provides additional information for predicting an upcoming asthma attack and/or monitoring the severity and progression of an attack.

Wheezing can be attributed to specific parts of the breathing cycle (mainly inspirium and expirium), and thus provides a useful insight regarding the type of upcoming or progressing respiratory distress. In addition, wheezing can be filtered according to the periodicity of the breathing cycle, thus enhancing identification of breathing-related sounds of the obstructed airways, and improving the ability to reject ambient noises that are not related to the breathing activity. Periodic, breathing-cycle-related wheezing can provide additional insight regarding the type of upcoming or progressing respiratory distress.

In an embodiment of the present invention, pattern analysis module 16 comprises cough analysis module 26, which is adapted to detect and/or assess coughing episodes associated with approaching or occurring clinical episodes. In asthma, mild coughing is often an important early pre-episode marker indicating an upcoming onset of a clinical asthma episode (see, for example, the above-mentioned article by Chang AB). In congestive heart failure (CHF), coughing may provide an early warning of fluid retention in the lungs caused by worsening of heart failure or developing cardiovascular insufficiency.

For some applications, coughing sounds are extracted from motion sensor 30 installed in, on, or under a reclining surface, typically using acoustic band filtering of between about 50 Hz and about 8 kHz, e.g., between about 100 Hz and about 1 kHz. Alternatively, the signal is filtered into two or more frequency bands, and motion data acquisition module 20 uses at least one frequency band of typically very low frequencies in the range of up to 5 Hz for registering body movements, and at least one other frequency band of a higher frequency range, such as between about 50 Hz and about 8 kHz, for registering acoustic sound. For some applications, the module uses a narrower acoustic band, such as between about 200 Hz and about 1 kHz Reference is made to FIGS. 8A-B, which are graphs showing different frequency components of a motion signal, in accordance with an embodiment of the present invention. Coughing events comprise simultaneous body movement and bursts of non-vocal sounds followed by vocal sounds. Cough analysis module 26 extracts coughing events by correlating coughing signals from the acoustic signal with body movement signals from the motion signal. Typically, module 26 relies on both mechanical and acoustical components for positive detection of coughing events. FIG. 8A shows a low-frequency (less than 5 Hz) component 114 of the measured signal, and FIG. 8B shows a high-frequency (200 Hz to 1 kHz) component 116 of the measured signal. Cough analysis module 26 typically identifies as coughs only events that are present in both low- and high-frequency components 114 and 116. For example, high-frequency event A in component 116 is not accompanied by a corresponding low-frequency event in component 114. Module 26 therefore does not identify event A as a cough. On the other hand, high-frequency events B, C, D, and E in component 116 are accompanied by corresponding low-frequency events in component 114, and are therefore identified as coughs. For some applications, cough analysis module 26 utilizes techniques described in one or more of the above-mentioned articles by Korpas J et al., Piirila P et al., and Salmi T et al.

In an embodiment of the present invention, pattern analysis module 16 extracts breathing rate from a continuous heart rate signal using frequency demodulation, e.g., standard FM demodulation techniques. This is possible because the heart rate signal generally displays a normal breathing-related sinus-arrhythmia pattern.

In an embodiment of the present invention, pattern analysis module 16 extracts breathing rate from a continuous heart rate signal using amplitude demodulation, e.g., using standard AM demodulation techniques. This is possible because respiration-related chest wall movement induces mechanical modulation of the heartbeat signal.

In an embodiment of the present invention, pattern analysis module 16 uses an amplitude- and/or frequency-demodulated heart rate signal to confirm adequate capture of the breathing and heart rate signals, by comparing the breathing rate signal with the demodulated sinus-arrhythmia pattern extracted from the heart-rate signal. For some applications, the sinus-arrhythmia pattern is frequency-demodulated by taking a series of time differences between successive heart beats, providing a non-biased estimate of the ongoing breathing pattern. Alternatively or additionally, the heart beat is amplitude-demodulated using high-pass filtering, full-wave rectification, and low-pass filtering.

Reference is made to FIG. 9, which includes graphs showing several signals in time and corresponding frequency domains, in accordance with an embodiment of the present invention. Graphs 120 and 122 show a respiration signal in the time and frequency domains, respectively. Graphs 124 and 126 show amplitude-demodulated and frequency-demodulated respiratory patterns, respectively, both of which were derived from the heartbeat signal shown in a graph 128. Graphs 130 and 132 show the respiration signals derived from graphs 124 and 126, respectively, in the frequency domain.

These graphs demonstrate the similarity between (a) breathing rate pattern derived directly from a respiration signal, as shown in graphs 120 and 122, and (b) breathing rate pattern derived indirectly from a heartbeat signal, as shown in graphs 124, 126, 130, and 132. This similarity is particularly pronounced in the frequency domain, as shown in graphs 122, 130, and 132.

In an embodiment of the present invention, pattern analysis module 16 derives a heartbeat signal from a breathing-related signal. This approach may be useful, for example, if the breathing-related signal is clearer than the directly-monitored heartbeat signal. This sometimes occurs because the breathing-related signal is generated by more significant mechanical body movement than is the heartbeat-related signal.

In an embodiment of the present invention, the measured breathing-related signal is used to demodulate the heartbeat-related signal and thus enable improved detection of the heartbeat-related signal. For some applications, breathing pattern analysis module 22 extracts breathing-related signals using spectral filtering in the range of about 0.05 to about 0.8 Hz, and heartbeat pattern analysis module 23 extracts heartbeat-related signals using filtering of in the range of about 0.8 to about 5 Hz. Heartbeat pattern analysis module 23 demodulates the heartbeat-related signal using the breathing-related signal, such as by multiplying the heartbeat-related signal by the breathing-related signal. This demodulation creates a clearer demodulated signal of the heart rate-related signal, thereby enabling its improved detection. In some cases, the power spectrum of the demodulated signal will show a clear peak corresponding to the demodulated heart rate.

FIGS. 10A-C are graphs showing frequency spectra, measured in accordance with an embodiment of the present invention. FIG. 10A shows a frequency spectrum signal 140 of a raw heartbeat-related signal (raw signal not shown), and FIG. 10B shows a breathing-related frequency spectrum signal 142, as measured simultaneously. FIG. 10C shows a demodulated spectrum signal 144 that is the product of breathing-related spectrum signal 142 (FIG. 10B) and heartbeat-related spectrum signal 140 (FIG. 10A). A clear peak 150 can be seen in demodulated spectrum signal 144, which represents the demodulated heartbeat frequency.

For some applications, the breathing-related signal used in the demodulation is filtered with a reduced top cut-off frequency (for example 0.5 Hz, instead of the 0.8 Hz mentioned above). Such a reduction generally ensures that only the basic sine wave shape of the breathing-related signal is used in the demodulation calculation.

In an embodiment of the present invention, breathing pattern analysis module 22 is configured to detect, typically during night sleep, an abnormal breathing pattern associated with CHF, such as tachypnea, Cheyne-Stokes Respiration (CSR), or periodic breathing.

In an embodiment of the present invention, system 10 is adapted to determine fetal heart rate. Typically, maternal heart rate in a relaxed setting is below 100 BPM, while healthy fetal heart rate is typically above 110 BPM. Heartbeat pattern analysis module 23 of system 10 distinguishes the fetal heart signal from the maternal heart signal, typically using lower pass-band filtering for the maternal heartbeat signal, and higher pass-band filtering to obtain the fetal heartbeat signal.

Figure 11:
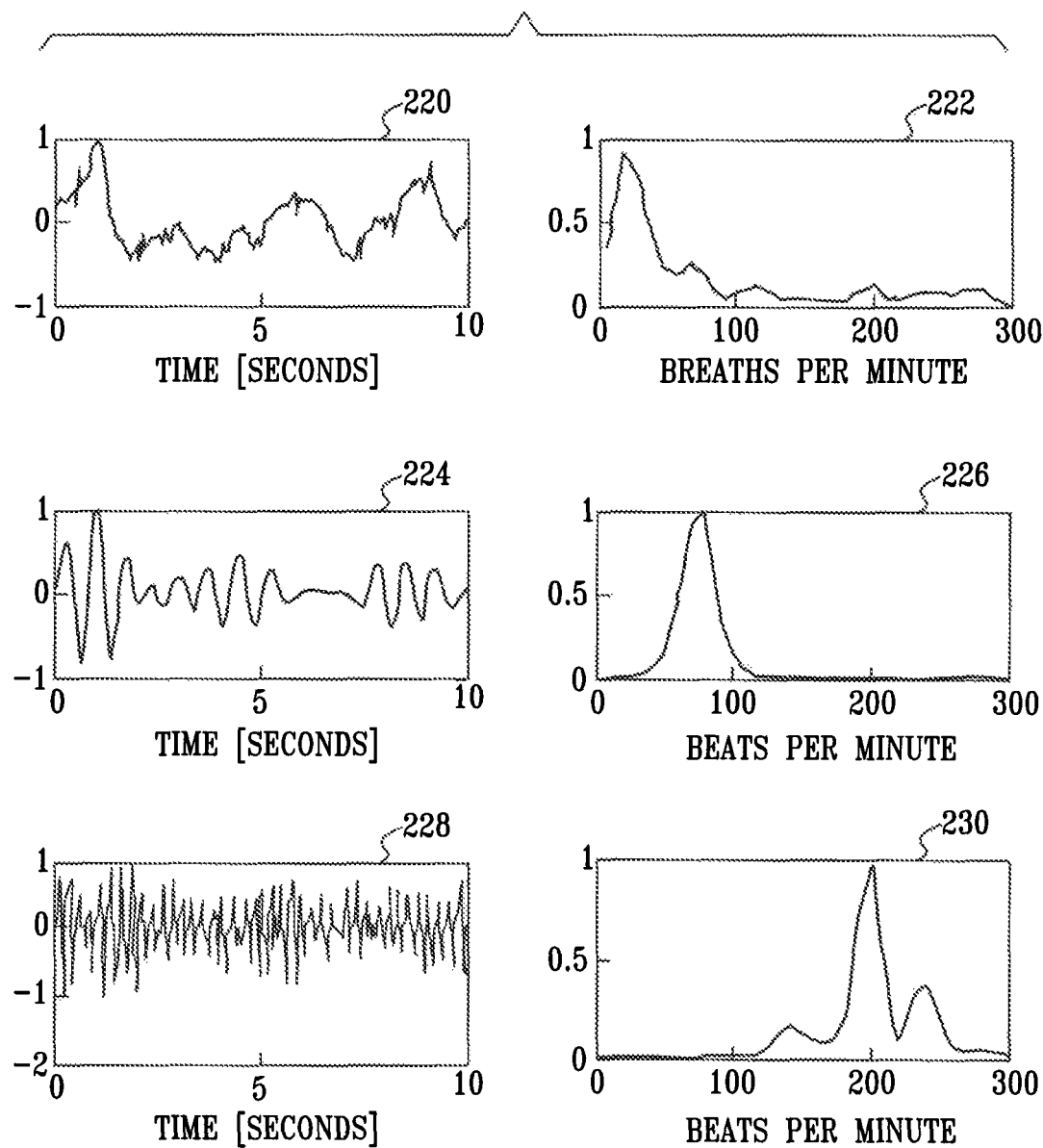
FIG. 11 includes graphs showing combined and decomposed maternal and fetal heartbeat signals, measured in accordance with an embodiment of the present invention.

FIG. 11 includes graphs showing combined and decomposed maternal and fetal heartbeat signals, measured in accordance with an embodiment of the present invention. Graphs 220 and 222 show a measured combined maternal and fetal respiration and heart signal, in the time and frequency domains, respectively. The signal shown in graph 220 was decomposed into its two constituents: (1) maternal heart signal, shown in the time and frequency domains in graphs 224 and 226, respectively, and (2) fetal heart signal, shown in the time and frequency domains in graphs 228 and 230, respectively.

In an embodiment of the present invention, the maternal breathing signal is used to differentiate or confirm maternal heartbeat patterns by matching the maternal breathing pattern with the maternal heart sinus-arrhythmia pattern. This is possible because, as mentioned above, the maternal pulse is frequency- and amplitude-modulated by the maternal breathing rate. Confirmation that maternal heartbeat has been correctly identified enables the identification of fetal heartbeat pattern.

In an embodiment of the present invention, the maternal breathing-related signal (which is often stronger than the fetal heartbeat-related signal) is used to demodulate the fetal heartbeat-related signal. This is possible because in some cases the fetal heart rate signal is amplitude-modulated by the maternal respiration signal. In these cases, the maternal respiration signal, which is relatively easy to detect, is used to extract the fetal heart rate signal, which is relatively difficult to detect, from background noise. For example, the fetal heart rate signal may determined by: (1) determining the maternal respiration rate using techniques described hereinabove; (2) passing the motion signal through a bandpass filter appropriate for fetal heart rate (e.g., about 1.2 Hz to about 3 Hz); (3) multiplying the filtered signal by the respiration signal; (4) performing a Fast Fourier Transform on the resulting signal; and (5) identifying a peak in the transformed signal as corresponding to the fetal heart rate.

In an embodiment of the present invention, system 10 is adapted to measure fetal motion patterns, which have an amplitude or frequency characteristic which is different from maternal movement. The signal generated by fetal motion is weaker than the signal generated by maternal motion, and has a higher frequency (when analyzed in the frequency domain) than the signal generated by maternal motion. In addition, fetal motion is generally registered primarily (or at least most strongly) by the abdominal sensors, while maternal motion is generally registered both by the abdominal sensors and other sensors (e.g., leg sensors). For some applications, system 10 comprises a plurality of motion sensors 30, and system 10 monitors high frequency movement in the vicinity of the mother's abdomen, in order to identify and count fetal movements.

In an embodiment of the present invention, system 10 is adapted to measure both fetal motion and fetal heart rate, as described hereinbelow with reference to FIG. 2. Changes in fetal heart rate correlated with fetal motion may be used as an indication of fetal health. A healthy fetus generally experiences periods of motion, with a correlating increase in fetal heart rate. An unhealthy fetus generally has reduced or no motion, and/or a relatively constant heart rate.

Reference is again made to FIG. 2. In an embodiment of the present invention, system 10 is adapted to measure fetal heart rate, such as by using techniques described herein. For some applications, user interface 24 comprises a speaker 240, and the user interface is adapted to drive the speaker to output an acoustic signal representative of the measured fetal heart rate data. For some applications, user interface 24 outputs the heart rate as a heartbeat, by simulating the sound of fetal heartbeat generated by standard fetal monitors, e.g., by synthesizing the sound or playing a pre-recorded sound. Alternatively, user interface 24 outputs the heart rate using other sounds, such as simple tones.

In an embodiment of the present invention, pattern analysis module 16 compares one or more of the monitored fetal parameters (heart rate, breathing rate, and motion) to a respective baseline pattern, and identifies a deviation from baseline. For some applications, pattern analysis module 16 combines one or more fetal and maternal parameters, such as by using the parameter combination techniques described hereinabove with reference to FIG. 2, and compares the combined parameters to respective combined baseline parameters. The analysis module identifies deviation from baseline as indicative of or predictive of a condition. For example, changes in both maternal and fetal parameters may be indicative of the onset of preeclampsia.

In an embodiment of the present invention, system 10 is adapted to detect fetal heartbeats, and to analyze the heartbeats to determine fetal heart rate variability. The heart rate variability is used as an indication of fetus movement and vitality. For example, fetal heart rate of a healthy fetus is expected to vary by at least 15 beats per minute for 15 to 30 seconds twice or more in a 10 minute period or five times or more in a 20 minute period. Significant deviations from these values are used by system 10 to indicate a possible pathology.

In an embodiment of the present invention in which motion sensor 30 comprises a grid of multiple pressure or strain gauge sensors, system 10 uses the grid: (a) to assess body posture, e.g., to identify the location of the abdomen and/or the lungs, (b) to ensure optimal reception of breathing inspiration and expiration signals, and/or (c) to monitor asthma-related biphasic chest-abdomen breathing patterns known as thoracoabdominal asynchrony (TAA) or phase angle. In TAA, there is a phase shift between the respiratory motion of the rib cage and abdomen. Use of a plurality of sensors enables system 10 to measure the phase difference in the strain or pressure measured by the different sensors in relation to the different body parts located in respective vicinities of the sensors.

In an embodiment of the present invention in which motion sensor 30 comprises a grid of multiple pressure or strain gauge sensors, system 10 uses the grid to assess weight variations in the lungs. During periods of lung congestion in CHF, fluid retention in lung tissue causes significant weight variations in the lungs. Such fluid retention generally requires immediate pharmaceutical intervention. For some applications, system 10 is configured to monitor day-to-day and/or night-to-night weight variations in lungs.

In an embodiment of the present invention, system 10 is configured to provide biofeedback information to the subject and/or to a bio-modification system, for the purpose of controlling and regulating breathing and/or heart rate. For some applications, the bio-modification system uses techniques described in one or more of the above-mentioned patents and/or patent application publication to Gavish or Gavish et al., mutatis mutandis. In this embodiment, motion sensor 30 is typically installed in, on, or under reclining surface 37 (FIG. 1). For some applications, only certain components of system 10 are used, rather than the complete system, such as motion data acquisition module 20, motion sensor 30, breathing pattern analysis module 22, and/or heartbeat pattern analysis module 23 (FIG. 2).

In an embodiment of the present invention, system 10 is configured to monitor sleep cycles by monitoring cardiac and respiratory data, and to identify that a sleeping user is in an optimal sleep stage for awakening, such as light sleep or REM sleep. Upon detection of such sleep stage during a user-selected timeframe for awakening, system 10 drives user interface 24 to generate a visible and/or auditory signal to awaken the user. For some applications, techniques described in the above-mentioned article by Shinar Z et al. are used for obtaining sleep staging information from respiration and heart rate data, mutatis mutandis. In this embodiment, motion sensor 30 is typically installed in, on, or under reclining surface 37 (FIG. 1). For some applications, only certain components of system 10 are used, rather than the complete system, such as motion data acquisition module 20, motion sensor 30, breathing pattern analysis module 22, and/or heartbeat pattern analysis module 23 (FIG. 2).

In an embodiment of the present invention, system 10 performs continuous monitoring and registration, on a night-to-night basis, of multi-sign data, including life signs and auxiliary signs, such as breathing patterns, heartbeat patterns, movement events, and coughing. The registered multi-sign data is used to construct a personalized patient file, which serves as a reference for tracking of pathophysiological deviations from normal patterns.

In an embodiment of the present invention, a plurality of measured parameters are combined using the following formula:

$$F = A1 * \Delta P1 + A2 * \Delta P2 + \ldots + An * \Delta Pn \quad \text{(Equation 1)}$$

where Ai is the relative weight given to parameter Pi, and ΔPi is the difference between the value of Pi for a given night and a baseline value defined for Pi. F is typically calculated on an hourly or a nightly basis and compared to a reference value that is predefined or determined based on personal history. If the value of F exceeds the reference value, the system alerts the subject and/or a healthcare worker. As appropriate for any of the parameters Pi, the absolute value of ΔPi may be evaluated, instead of the signed value of ΔPi. As appropriate for any of the parameters Pi, the square, square root, exponential, log, or any other similar function may be evaluated. Alternatively or additionally, for any of the parameters Pi, instead of using ΔPi, a value generated by inputting ΔPi into a lookup table is used. Further alternatively or additionally, the resulting function F is entered into a lookup table (either predefined or learned) in order to interpret the result.

In an embodiment of the present invention, a plurality of parameters are combined by calculating a score for each parameter and applying a function to combine the scores, such as Equation 1. For some applications, each score represents a probability of an occurrence of the value of the parameter if a clinical episode is not imminent within a certain time period, e.g., within the next 1 hour, 4 hours, 24 hours, or 48 hours. The function estimates a combined probability of an occurrence of the values of the parameters in combination if the clinical episode is not imminent within the time period. For example, for n monitored parameters, each with a respective threshold t(i), and a probability p(i) of crossing threshold t(i) when a clinical episode is not imminent, a binomial distribution is calculated to indicate the probability that an observed combination of threshold crossings is random. If the probability of observing the combination is low, then an alarm signal is generated or other action taken. For example, probability of observing the combination may be compared to a threshold that is either predefined or learned by system 10. If the probability is less than the threshold, system 10 generates an alarm indicating that there is a high probability than an episode is imminent. For some applications, the scores for each parameter are weighted, as described above with reference to Equation 1.

In an embodiment of the present invention, system 10 is adapted to learn the above-described thresholds, weights, and/or probabilities. For some applications, system 10 uses the following method for performing such learning:

upon each occurrence of an episode, the subject or a healthcare worker enters an indication of the occurrence of the episode into system 10 via user interface 24. Alternatively or additionally, the system itself identifies an episode by detecting parameters clearly indicative of an episode (e.g., a respiration rate of over 30 breathers per minute). Further alternatively, system 10 determines that an episode has occurred based on input from drug administration device 266 (e.g., the system interprets a level of usage of an inhaler beyond a certain threshold as indicative of an occurrence of an episode).

from time to time (e.g., once every two weeks), system 10 compares actual episodes with episodes about which the system provided a warning;

for each correctly predicted episode, false negative, and false positive, the system checks the accuracy of the prediction given by the system according to the current thresholds, weights, and probability distribution; and responsively to this check, the system incrementally adjusts one or more of the thresholds, weights, or probability distributions.

For example, some asthma patients have coughs that precede their attacks, while other patients do not. Every two weeks, the system checks whether cough symptoms occurred prior to each attack. The system accordingly adjusts the threshold up or down by a certain percentage (e.g., 5%) for each false positive or false negative. For example, for some applications, for each correctly predicted attack, the system adjusts the weight of the cough parameter (for example, if there was substantial coughing prior to the most recent five attacks, the system increases the weight of the cough parameter). Alternatively or additionally, the system may adjust the weight of the coughing parameter for false positives or false negatives.

In an embodiment of the present invention, system 10 monitors and analyzes episodes of nocturnal restlessness and/or awakening, which are symptoms of several chronic conditions, such as asthma and CHF. Typically, system 10 quantifies these episodes to provide an objective measure of nocturnal restlessness and/or awakening. As described hereinabove, system 10 analyzes a cyclical motion signal of the subject in the frequency domain, and identifies peaks in the frequency domain signal corresponding to respiration rate and heart rate (and, optionally, corresponding harmonics). Body motion of the subject generates a sudden, generally stronger non-cyclical component in the motion signal. System 10 interprets an occurrence of such non-cyclical motion to be a restlessness episode if such motion is transient (e.g., has a duration of between about 2 and about 10 seconds), after which the periodic respiration/heart beat signal returns. System 10 interprets an occurrence of such non-cyclical motion to be an awaking event if such motion continues for more than a certain period of time, or if there is no periodic signal for more than a certain period of time (both of which conditions indicate that the subject is no longer in bed).

Reference is made to FIG. 12, which is a graph showing body movement, in accordance with an embodiment of the present invention. In this embodiment, system 10 monitors restlessness manifested by excessive body movement during sleep. System 10 quantifies the restlessness to provide an objective measure of nocturnal restlessness. As seen in FIG. 12, a restlessness event 250 is characterized by a substantial increase in body movement, compared to normal sleep periods 252. In this embodiment, motion sensor 30 is typically installed in, on, or under reclining surface 37 (FIG. 1). For some applications, system 10 classifies a time segment as indicative of restlessness when the standard deviation of the measured motion signal during the time segment is at least a certain multiple of the average standard deviation of the motion signal during at least a portion of the sleep period. For example, the multiple may be between about 2 and about 5, such as about 3. Alternatively, system 10 uses other mathematical and/or statistical indicators of deviation, such as the frequency domain analysis techniques described above. Alternatively, system 10 uses an integrator function J(i) which is defined by the following equation:

$$J(i)=(1-\text{alpha})*J(i-1)+\text{alpha}*abs(X(i)) \quad \text{(Equation 2)}$$

where X(i) is the raw signal as sampled from motion sensor 30. If for example, X(i) has 10 samples per second, appropriate values for alpha would be between 0.01 and 0.1, e.g., 0.05. The signal J is typically averaged for the whole night, and a standard deviation is calculated. If at any point, J(i) exceeds the average by more than two times the standard deviation for a period lasting at least 2 seconds, a restlessness event is defined.

For some applications, once such restlessness events are identified, system 10 counts the number of events per time epoch (for example, each time epoch may have a duration of 30 minutes). To detect a clinical episode (such as of any of the conditions described herein), system 10 compares measured night patterns with a reference pattern, according to certain criteria. For example, system 10 may generate a clinical episode warning if a restlessness event is detected in more than a certain percentage of time epochs (e.g., more than 10%, 20%, or 30%). Alternatively, system 10 generates a clinical episode warning if the total number of restlessness events per night exceeds a threshold value. For some applications, the reference pattern or threshold value is determined based on population averages, while for other applications, the reference pattern or threshold value is determined by averaging the data from the subject over several non-symptomatic nights.

Reference is made to FIG. 13, which is a graph showing restlessness events during normal sleep and during a clinical episode of asthma, in accordance with an embodiment of the present invention. A line 260 shows the number of restlessness events per 30-minute epoch during normal sleep (the bars indicate standard error). A line 262 shows the number of restlessness events per 30-minute epoch during a night characterized by a clinical episode of asthma.

In an embodiment of the present invention, system 10 monitors episodes of arousal because of general restlessness or coughing, in order to provide additional evidence for certain pathologies such as an approaching or progressing asthma episode.

In an embodiment of the present invention, system 10 records monitored parameters such as respiration, heart rate, and/or coughing during sleep at night. The system analyzes the recorded parameters either continuously or after the conclusion of sleep, such as in the morning, to predict an approaching clinical episode. In the morning, or later in the day, system 10 drives user interface 24 to alert the subject about the approaching clinical event. Such approaching clinical events generally do not occur until at least several hours after system 10 predicts their approach, such as at least 12 or 24 hours. Therefore, delaying notification until the morning or later in the day still generally provides sufficient time for the subject to begin preventive treatment before clinical manifestation of the episode begins, without needlessly interrupting the subject's sleep. For some applications, system 10 analyzes the parameters to estimate a severity and/or urgency of the approaching clinical episode, and to determine whether to wake the subject responsively to the severity and/or urgency.

For applications in which system 10 detects worsening of a clinical episode already in progress, or that an episode will begin within a relatively short period of time (e.g., within four hours), system 10 provides a warning without delay to enable fast treatment of the worsening episode. In addition, system 10 typically records and continuously analyzes monitored parameters throughout sleep.

In an embodiment of the present invention, system 10 is configured to detect episodes of pulse irregularity, such as during ventricular fibrillation or cardiac arrest, and to provide an immediate alert upon detection of such an irregularity. Alternatively or additionally, upon detection of such an irregularity, system 10 automatically administers an appropriate electric or magnetic shock. For example, user interface 24 may comprise an implantable or external cardioverter/defibrillator, as is known in the art.

In an embodiment of the present invention, motion sensor 30 and all or a portion of motion data acquisition module 20 are packaged in a biocompatible housing (or in multiple housings) adapted to be implanted in subject 12. The implantable components comprise a wireless transmitter, which is adapted to transmit the acquired signals to an external receiver using a transmission technology such as RF (e.g., using the Bluetooth® or ZigBee protocols, or a proprietary protocol) or ultrasound. Alternatively, one or more of analysis modules 22, 23, 26, 28, 29, or 31, and/or user interface 24 are also adapted to be implanted in the subject, either in the same housing as the other implantable components, or in separate housings. Further alternatively, motion sensor 30 is adapted to be implanted in subject 12, while motion data acquisition module 20 is adapted to be external to the subject, and in communication with motion sensor 30 either wirelessly or via wires.

In an embodiment in which all or a portion of system 10 is implantable, sensor 30 comprises a multi-sensor, which comprises two or more sensors for measurement of one or more of the following parameters: (a) mechanical vibrations, (b) acoustical vibrations, (c) electrocardiogram, (d) electromyogram, (e) lung impedance, and (f) accelerations. For some applications, system 10 uses the multi-sensor data to perform one or more of the following analyses: (a) respiration analysis, such as respiration rate, duty cycle, expiration/inspiration ratio, and/or respiration depth; (b) cough measurement; (c) pulse analysis, such as heart rate, heart rate variability, and/or inter-pulse timing; and (d) sleep restlessness analysis. For some applications, the multi-sensor data analyses are used for prediction and/or monitoring of clinical episodes in chronic diseases such as asthma, CHF, diabetes, and epilepsy.

For some applications, the implantable components of system 10 communicate with an external device installed in, on, or under a reclining surface, or mounted on an external surface of the subject's body. Responsively to detection of a critical pulse irregularity or pathology, such as ventricular fibrillation or cardiac arrest, the external device is adapted to apply an appropriate electric or magnetic shock. For example, the external device may comprise an implantable or external cardioverter/defibrillator, as is known in the art. Alternatively, the implantable components of system 10 communicate, wirelessly or via wires, to an implantable cardioverter/defibrillator, as is known in the art. Alternatively, the external device monitors a portion of the parameters that are straightforward to monitor externally (e.g., leg movement), while the implantable components of system 10 monitor parameters that are straightforward to monitor internally. An implanted or external processing unit integrates the information to provide the full multi-parameter monitoring functionality described above.

In an embodiment of the present invention, user interface 24 is configured to accept input of information regarding medical treatment the subject is currently receiving, such as drug and dosage information. Prophylactic or clinical pharmacological treatments may affect physiological parameters such as respiration, heart rate, coughing, and restlessness. For example, respiration patterns of asthma patients may be affected by usage of bronchodilator medication. Pattern analysis module 16 therefore takes the entered information into account when assessing deviations of measured parameters from baseline parameters. For example, breathing pattern analysis module 22 may disregard a slight increase of about 10% in respiration rate compared to baseline if the increase occurs within about one hour after use of bronchodilator medication and lasts up to 8 hours thereafter.

Reference is again made to FIG. 2. For some applications, drug treatment information is directly transmitted to system 10 from a drug administration device 266, rather than manually entered into user interface 24. Such drug information treatment may include, for example, which drug has been administered (and/or the drug's active ingredients), the dosage of the administered drug, and/or the timing of the administration. For some applications, system 10 takes the drug treatment information into account when determining the dosage and/or drug administration timing information that the system provides to drug administration device 266. Transmission of data to system 10 may be performed wirelessly or via wires. For example, drug administration device 266 may comprise a commercially-available drug administration device having communication capability, such as the Nebulizer Chronolog (Medtrac Technologies, Inc., Lakewood, Colo., USA), or the Doser (MEDITRACK Products, Hudson, Mass.).

In an embodiment of the present invention, system 10 automatically detects and extracts parameter pattern changes related to a specific pharmacological treatment, and considers the extracted pattern changes in assessment of parameter deviation from baseline patterns. For example, an increase of about 10% in respiration rate of an asthma patient, followed by a return to normal after about 6 to 8 hours, may be identified by system 10 as being associated with use of a bronchodilator.

Reference is yet again made to FIG. 2. In an embodiment of the present invention, system 10 is used in an automatic closed-loop with drug administration device 266. The drug administration device delivers a drug to subject 12. System 10 monitors the clinical effect of the drug, and provides feedback to the drug administration device to maintain or update the drug dosage. For some applications, drug administration device 266 comprises one or more of the following: a nebulizer, an inhaler, a vaporizer (e.g., in a room in which the subject is), a continuous positive airway pressure device, a spraying system, or an intravenous drug administration system. Alternatively or additionally, system 10 is configured to determine the optimal level of humidity in the room in which the subject is, in order to optimize one or more physiological parameters of the subject, and to drive a vaporizer or other humidifying device to appropriately control the humidity. Further alternatively or additionally, system 10 is configured to determine the optimal room temperature, in order to optimize one or more physiological parameters of the subject, and to drive an air conditioner and/or heater to appropriately control the temperature.

For some applications, drug treatment information is directly transmitted to system 10 from drug administration device 266, rather than manually entered into user interface 24. Such drug information treatment may include, for example, which drug has been administered (and/or the drug's active ingredients), the dosage of the administered drug, and/or the timing of the administration. For some applications, system 10 takes the drug treatment information into account when determining the dosage and/or drug administration timing information that the system provides to drug administration device 266.

For some applications, drug administration device 266 regulates the dosage of several drugs. For example, the drug administration device may regulate the dosage of drugs belonging to one or more of the following categories: bronchodilators, anti-inflammatories, antibiotics, and placebos. For some applications for treating asthma patients, drug administration device 266 comprises a metered-dose inhaler (MDI) comprising three chambers holding several types of drugs, such as a bronchodilator, an anti-inflammatory agent, and a placebo. When subject 12 wakes up in the morning, system 10 determines the current condition of the subject, and, responsively thereto, determines the appropriate dosage combination of the three drugs. System 10 communicates this dosage information to the MDI, which prepares the relevant combination to be inhaled. The subject activates the MDI for automatic administration of the appropriate combination and dosage of medications. These techniques obviate the need for the subject to know or control the drug combination delivered by the MDI. The techniques described in this paragraph are also appropriate for drug administration devices other than MDIs.

Reference is made to FIGS. 14A-B, which are graphs showing power spectrum densities of signals measured in accordance with an embodiment of the present invention. Lines 270 and 272 in FIGS. 14A and 14B, respectively, show the power spectrum density of signals measured under the abdomen and the legs, respectively. Peaks 274 and 276 correspond to the subject's respiration rate and heart rate, respectively. As can be seen in the graphs, for some applications heart rate is more clearly detectable in the signal measured under the legs.

Reference is made to FIG. 15, which is a schematic illustration of a configuration of system 10 comprising two motion sensors 30A and 30B, in accordance with an embodiment of the present invention. Motion sensors 30A and 30B are installed in, on, or under reclining surface 37, sensor 30A in a vicinity of abdomen 38 or chest 39 of subject 12, and sensor 30B in a vicinity of a portion of subject 12 anatomically below a waist of the subject, such as in a vicinity of legs 40 of the subject. System 10 samples and analyzes the signals from sensors 30A and 30B at generally the same time. The cardioballistic effect of the pulsating heart travels at a speed of approximately 5 meters per second, originating at the heart and moving towards the legs. For some applications, system 10 uses the delayed pulse detected from sensor 30B under the legs 40 to confirm the pulse detected from sensor 30A under abdomen 38 or chest 39. For some applications, system 10 comprises more than two motion sensors 30.

Reference is made to FIGS. 16A-B, which are graphs showing pulse signals measured simultaneously under legs 40 and abdomen 38, and the cross correlation between the signals of FIG. 16A, respectively, as measured and calculated in accordance with an embodiment of the present invention. For some applications, system 10 calculates the cross correlation between the signals measured under (a) a portion of subject 12 anatomically below the waist of the subject, such as legs 40 and (b) abdomen 38 or chest 39. For example, signals 290 and 292 in FIG. 16A show pulse signals simultaneously measured under abdomen 38 and the subject's legs, respectively. A line 294 in FIG. 16B shows the cross correlation of the two pulse signals of FIG. 16A. A first peak 296 of line 294 corresponds to the delay of the cardioballistic signal, which is approximately 0.12 seconds in this example. Peak 296 of the cross correlation signal is identified. A second peak 298 of the cross correlation is identified. The distance between the peaks corresponds to the distance between the heart beats and enables the calculation of the heart rate. For some applications, system 10 uses this indirectly calculated heart rate to correct for background noise in the signals that may cause the directly measured heart rate to be inaccurate.

Reference is again made to FIG. 15. In an embodiment of the present invention, abdomen and leg sensors 30A and 30B are placed under reclining surface 37 at a known distance D from one another (for example, D may be measured between the respective centers of the sensors). System 10 calculates the speed the cardioballistic signal travels in the subject's body by dividing distance D by the time difference corresponding to first peak 296 of cross correlation signal 294 (FIG. 16B). For some applications, system 10 calculates this speed continuously. A change in the speed serves as an indicator of a change in the subject's condition. For example, for some applications, system 10 uses the measured time difference and/or changes therein between the two pulse signals to estimate the subject's blood pressure and/or changes in blood pressure. Techniques described herein may be used in combination with techniques described in the above-mentioned U.S. Pat. No. 6,599,251 to Chen et al., mutatis mutandis. For some applications, system 10 uses the derived blood pressure information to monitor and predict the onset and progression of clinical episodes. For some applications, system 10 calculates the subject's absolute blood pressure. For these applications, the system is typically calibrated using a standard blood pressure measuring device, such as an oscillometric cuff.

Reference is made to FIG. 17, which is a schematic illustration of system 10 adapted to monitor a pregnant subject 300 and her fetus 302, in accordance with an embodiment of the present invention. In this embodiment, system 10 comprises two or more motion sensors 30, which the system uses to identify and discriminate between maternal pulse and fetal pulse. For some applications, a first sensor 30C is located under a portion of pregnant subject 300 anatomically below the waist of the subject, such as legs 40, for clear detection of the signal of the subject's pulse. A second sensor 30D is located under abdomen 38 of subject 300, and measures a combined signal of the maternal and fetal pulses. Additional sensors 30 may be used to further enhance signal quality. Pattern analysis module 16 eliminates the maternal pulse signal from the combined pulse signal to determine the fetal pulse.

For some applications, system 10 is configured to use the two or more sensors to identify and discriminate between maternal body movement and pulse, on the one hand, and fetal movement and pulse, on the other. Typically, the system uses first sensor 30C for clear detection of the signal of the subject's pulse and maternal body movements, and second sensor 30D to measure the combined signal of the maternal and fetal pulses and body movements. Pattern analysis module 16 eliminates the maternal pulse and movement signal from the combined pulse and movement signals to determine the fetal pulse and movement.

For some applications, pattern analysis module 16 identifies and discriminates the maternal pulse from the fetal pulse responsively to the delay in the signals measured by the abdomen and anatomically-below-the-waist (e.g., legs) sensors. For example, pattern analysis module 16 may use the cross-correlation techniques described hereinabove, mutatis mutandis. For example, the cross-correlation techniques described hereinabove may be used to identify the maternal pulse. This signal is subtracted from the combined signal. Alternatively, after finding the maternal pulse, the combined signal is filtered using a notch filter that removes the maternal pulse frequency. The resulting signal is then filtered using a bandpass filter appropriate for fetal pulse, e.g., between about 1 Hz and about 4 Hz, and the fetal pulse is identified using techniques described hereinabove.

Figure 18:
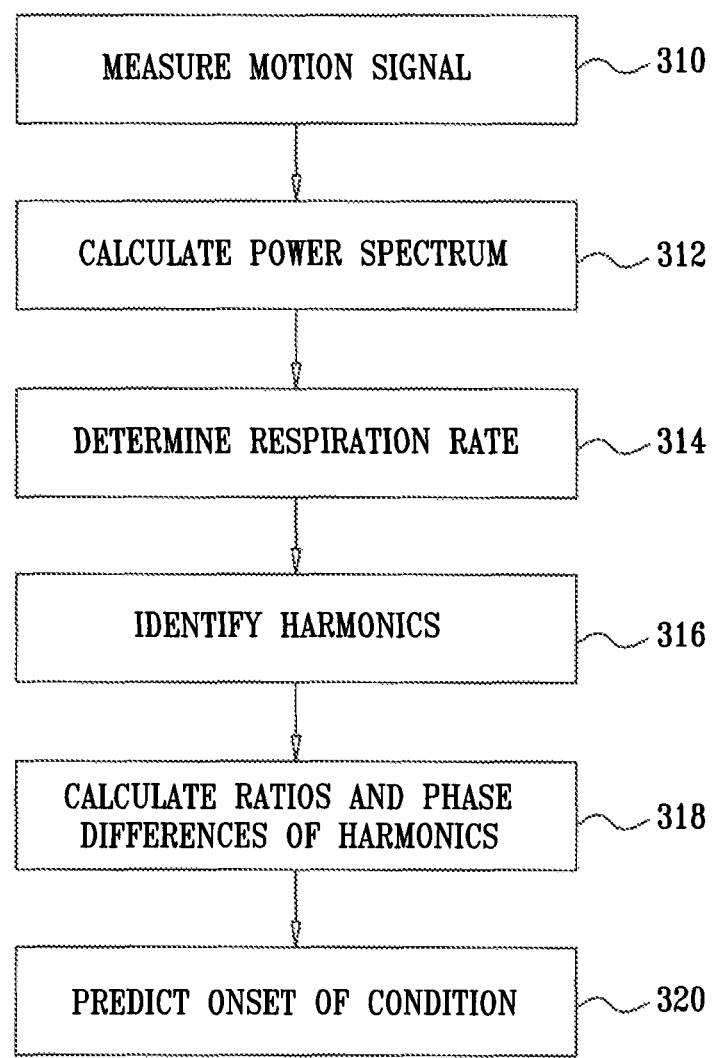
FIG. 18 is flow chart that schematically illustrates a method for predicting a physiological condition, in accordance with an embodiment of the present invention.

Reference is made to FIG. 18, which is a flow chart that schematically illustrates a method for predicting a physiological condition, in accordance with an embodiment of the present invention. In this embodiment, system 10 is configured to predict the physiological condition at least in part responsively to changes in ratios between different harmonics in the energy spectrum of the motion signal generated by motion sensor 30. At a measurement step 310, motion sensor 30 measures the motion signal. Breathing pattern analysis module 22 calculates the power spectrum of the measured motion signal, at a power spectrum calculation step 312. Module 22 identifies the respiration rate as the peak in the frequency range pertaining to respiration (e.g., between about 0.1 and about 1.0 Hz), at a respiration rate determination step 314. Alternatively, in order to determine the respiration rate, breathing pattern analysis module 22 uses zero-crossing or peak detection in the time domain, and then counts the peaks. Further alternatively, the module identifies the peaks, measures time intervals between peaks, arranges the intervals in order from highest to lowest, deletes a certain percentage at the top (e.g., 10%) and bottom (e.g., 10%), and averages the remaining intervals. Module 22 then identifies one or more harmonics, i.e., whole number multiples (or small numerator/denominator fractions, such as ½, if the resulting frequency is within the allowed frequency range) of this peak in the power spectrum, at a harmonics identification step 316. At a ratio and phase difference calculation step 318, module 22 calculates the ratios of the energy levels of the harmonics and the phase difference between the harmonics. Module 22 analyzes these parameters vs. baseline measurements, and interprets a deviation from baseline as indicative of an approaching physiological condition, at an onset of condition prediction step 310. For example, this deviation may be indicative of a level of thoracoabdominal asynchrony (TAA), or a phase angle thereof.

Reference is made to FIG. 19, which is a graph illustrating an exemplary power spectrum used for carrying out the method described hereinabove with reference to FIG. 18, in accordance with an embodiment of the present invention. This power spectrum was derived from data measured in an actual asthma patient. A line 321 represents the power spectrum of the respiration signal as measured and filtered at steps 310 and 312 of the method of FIG. 18. A peak 322 is identified as the largest peak in the range of about 0.1 to about 0.5 Hz, at step 314. This peak represents the basic respiration rate. A peak 324 is identified as the second harmonic of the respiration signal, at step 316. The ratio of the height of peak 322 to peak 324 is calculated and graphed for several hours during sleep time, at step 318. For some applications, a baseline reference ratio of peaks is calculated based on measured results during normal sleep. The ratio of peaks during sleep is compared to the baseline reference ratio of peaks in order to evaluate whether the ratio of peaks deviates from baseline, thus indicating an approaching onset of a clinical episode, at step 320. Also at step 318, the Fourier analysis provides a phase for each frequency. Typically, the phases for the base harmonic and the second harmonic are subtracted from one another, and the difference is analyzed in a similar manner to the analysis described above.

FIG. 20 is a graph showing the ratio of a first harmonic of a respiration signal of an asthma patient and the base frequency, measured in accordance with an embodiment of the present invention. As can be seen in the figure, during episodic sleep, the ratio of the energy levels of the harmonics, represented by a line 330, is substantially elevated compared to the ratio during normal, non-pre-episodic sleep, represented by a line 332. (The bars on the lines represent standard deviations.) For some applications, the substantial variation in the size of the error bars is, in and of itself, predictive or indicative of a clinical episode.

In an embodiment of the present invention, system 10 is adapted to identify and count the number of sleep apnea events that occur during a time period. System 10 compares the number of events with a baseline from a non-symptomatic day, and interprets a deviation as indicative of an episode.

Figure 21A:
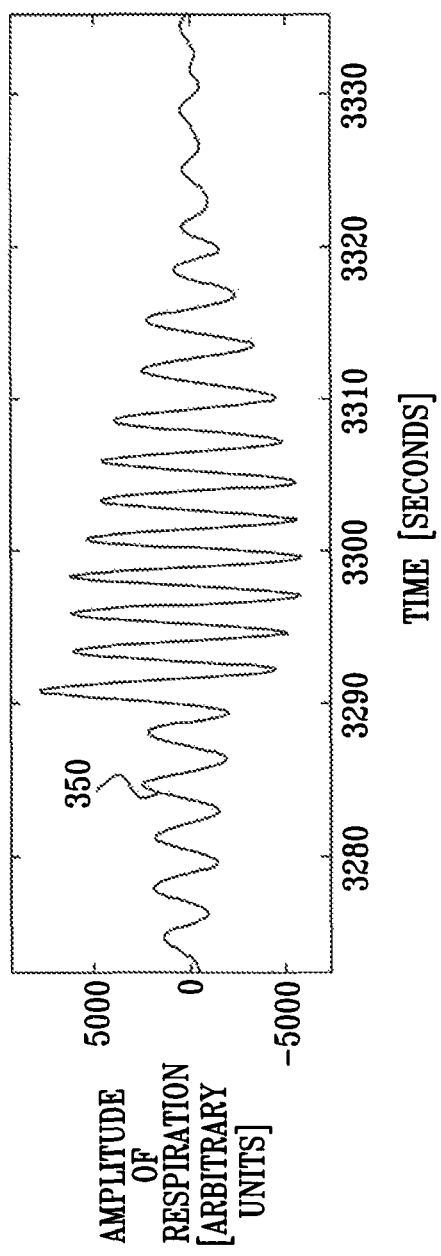
FIGS. 21A-B are graphs showing a respiration signal indicative of Cheyne-Stokes Respiration (CSR), and an analysis of the signal of FIG. 21A, respectively, in accordance with an embodiment of the present invention.
Figure 21B:
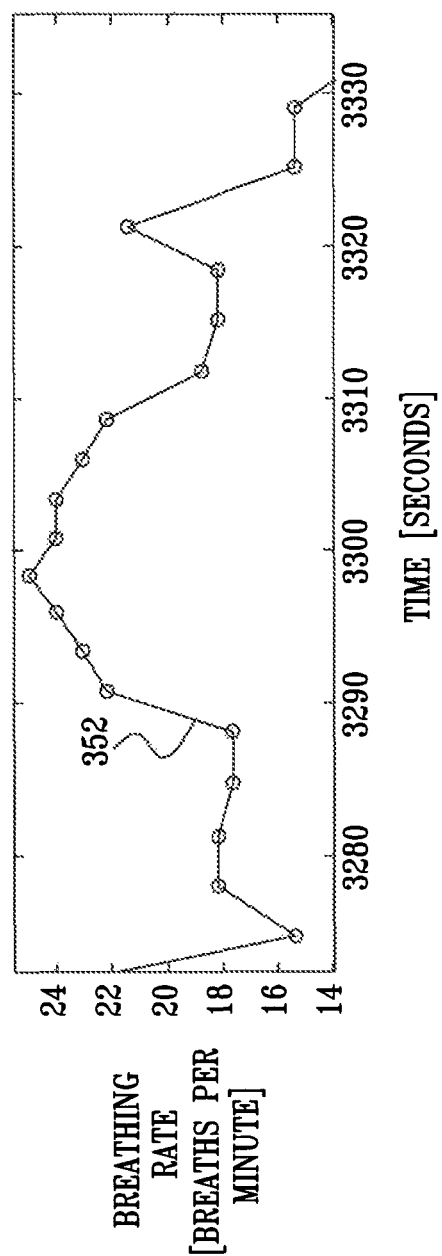

Reference is made to FIGS. 21A-B, which are graphs showing a respiration signal indicative of Cheyne-Stokes Respiration (CSR), and an analysis of the signal of FIG. 21A, respectively, in accordance with an embodiment of the present invention. In this embodiment, system 10 is adapted to identify CSR as an indicator of chronic conditions, such as CHF. A signal 350 in FIG. 21A represents the respiration signal of a sleeping subject, measured and filtered as described hereinabove. This signal is characteristic of CSR. System 10 measures the temporal distance between consecutive peaks of signal 350, and calculates the instantaneous respiration rate between each pair of consecutive peaks, as represented by a line 352 in FIG. 21B. Line 352 shows the expected periodicity in CSR, and is used for identifying this pattern. For some applications, system 10 measures and logs the number of such cycles per night, and uses this information as an indication of the onset and severity of clinical conditions, such as CHF.

Figure 22:
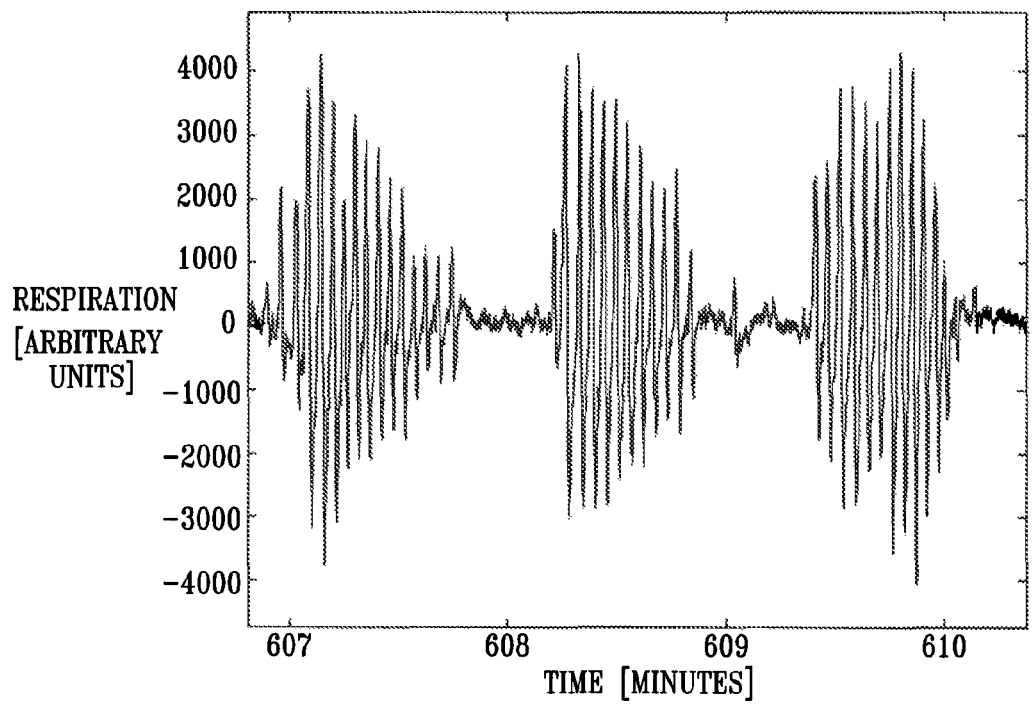
FIG. 22 is a graph showing a respiration signal indicative of Cheyne-Stokes Respiration (CSR), measured in accordance with an embodiment of the present invention.

FIG. 22 is a graph showing a respiration signal indicative of Cheyne-Stokes Respiration (CSR), measured in accordance with an embodiment of the present invention.

Figure 23:
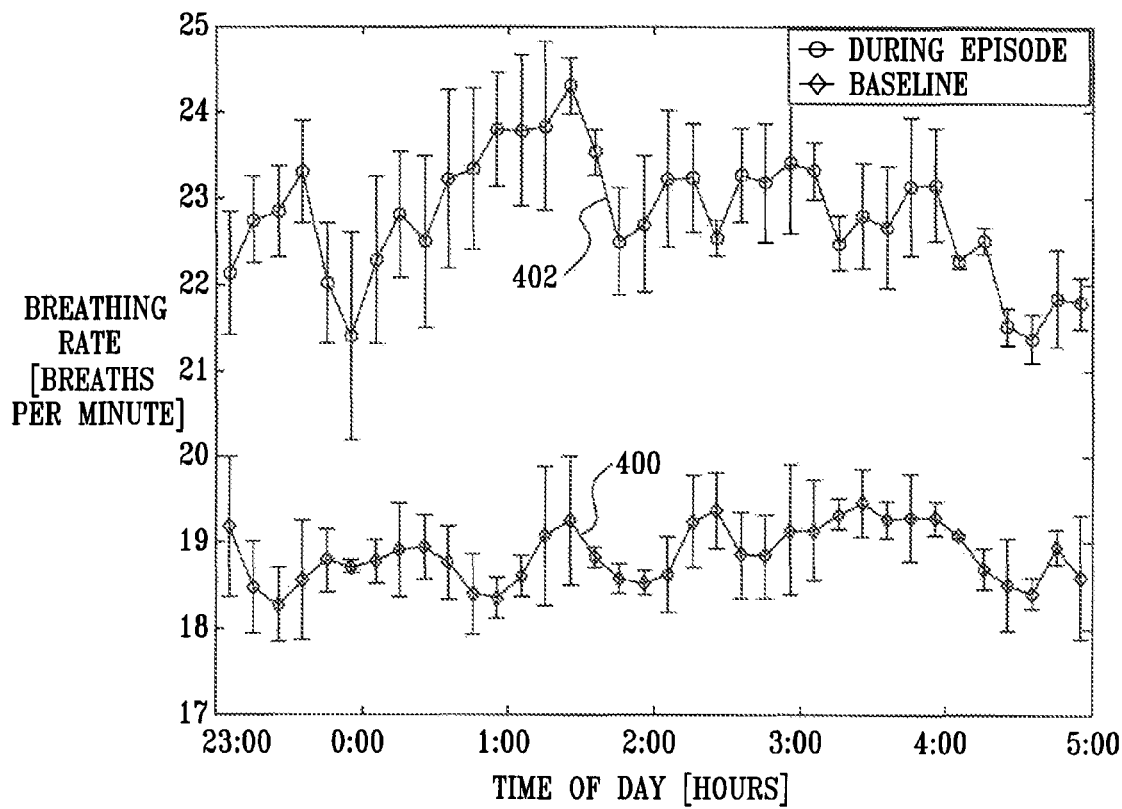
FIG. 23 is a graph of exemplary baseline and measured breathing rate nighttime patterns, respectively, measured in accordance with an embodiment of the present invention.

FIG. 23 is a graph of baseline and breathing rate nighttime patterns, respectively, measured in accordance with an embodiment of the present invention. A line 400 represents a normal baseline pattern in the absence of CSR, and a line 402 represents a pattern during a night during CSR. The bars represent one standard error.

In an embodiment of the present invention, system 10 is adapted to identify Periodic Limb Movements in Sleep (PLMS). The occurrence and level of this syndrome is used as an indicator of the onset of chronic conditions, such as CHF, diabetes, anemia, and kidney disease. For some applications, system 10 comprises a single sensor 30, while for other applications, system 10 comprises two or more sensors 30.

Reference is again made to FIG. 2. In an embodiment of the present invention, system 10 comprises a temperature sensor 380 for measurement of body temperature. For some applications, temperature sensor 380 comprises an integrated infrared sensor for measurement of body temperature. Body temperature is a vital sign indicative of general status of systemic infection and inflammation. Global rise in body temperature is used as a first screening tool in medical diagnostics.

Reference is again made to FIGS. 1 and 2. In an embodiment of the present invention, system 10 comprises first and second motion sensors 30. Motion sensors 30 are installed in, on, or under reclining surface 37, such that the first motion sensor is in a vicinity of lungs of subject 12, and the second motion sensor is in a vicinity of an abdomen of subject 12, e.g., a lower abdomen of subject 12. System 10 samples and analyzes breathing-related signals from both sensors at generally the same time. For some applications, breathing pattern analysis module 16 calculates a phase shift between the breathing-related signals of the sensors, such as by cross-correlating the two breathing-related signals, e.g., as described hereinabove. Breathing pattern analysis module 16 analyzes the phase shift to determine a measure of thoraco-abdominal asynchrony (TAA), a prominent clinical feature of patients with airway obstruction. Alternatively or additionally, module 16 analyzes the phase shift to identify and monitor the onset of clinical conditions, such as an asthma episode. For other applications, module 16 calculates a ratio of the amplitudes of the breathing-related signals, and analyzes the ratio to determine a measure of accessory muscle use in breathing. A greater ratio of the breathing-related signal measured by the abdominal sensor to the breathing-related signal measured by the lung sensor is generally indicative of a greater level of accessory muscle use in breathing, Accessory muscle use is a prominent clinical feature of patients with airway obstruction.

Reference is again made to FIGS. 1 and 2. In an embodiment of the present invention, system 10 comprises first and second motion sensors 30. Motion sensors 30 are installed in, on, or under reclining surface 37, such that the first motion sensor is in a vicinity of lungs of subject 12, and the second motion sensor is in a vicinity of the abdomen of subject 12. System 10 samples and analyzes breathing-related signals from both sensors at generally the same time. For some applications, breathing pattern analysis module 16 analyzes the combined signal from the sensors to differentiate between inspiration and expiration. For example, in some cases, during inspiration movement in the vicinity of the lungs precedes movement in the vicinity of the abdomen, and during expiration lung area movement trails that of the abdomen. For some applications, the ratio of durations of expiration to inspiration is substantially continuously calculated. A lengthening of the expiration duration compared to the inspiration duration is indicative of airway obstruction.

In an embodiment of the present invention, system 10 is configured to identify early signs of an onset of hypoglycemia in a diabetic subject. The system identifies an increase in a level of physiological tremor as being indicative of such onset, and/or an increase in the level of tremor in combination with other parameters described hereinabove, such as heart rate, respiration rate, and/or awakenings, and/or a change in the heart beat pattern indicative of palpitations (by analyzing the timing between peaks of the heart beat signal, using techniques described herein). Typically, the system detects physiologic tremor by monitoring body motion at between about 4 Hz and about 18 Hz, such as between about 8 Hz and about 12 Hz. Alternatively, the system identifies the increase in the level of physiological tremor as being indicative of an onset or progression of a condition selected from the list consisting of: Parkinson's disease, Alzheimer's disease, stroke, essential tremor, epilepsy, stress, fibrillation, and anaphylactic shock. For some applications, system 10 is adapted to drive user interface 24 to display one or more properties of the detected physiological tremor, such as an amplitude or spectrum image of the tremor. For example, system 10 may be used as a bedside hospital vital signs diagnostic system. For some applications, the hypoglycemia is identified by analyzing the heart signal to identify palpitations.

In an embodiment of the present invention, system 10 monitors a subset of the physiological parameters described hereinabove, such as respiration rate, heart rate, cough count, blood pressure changes, expiration/inspiration ratio, respiration harmonics ratio, and tremor at multiple time points during the night. Pattern analysis module 16 assigns a score to each monitored parameter, and combines the scores to derive a compound score. The following is an exemplary formula for such a combination:

$$\text{Combined Score} = \text{Const1} * (\text{Average Night Heart Rate} - \text{Baseline Heart Rate}) + \text{Const2} * (\text{Average Night Breathing Rate} - \text{Baseline Breathing Rate}) + \text{Const3} * (\text{Number of Night Coughs}) + \text{Const4} * (\text{Average Breathing Rate in Hour3} - \text{Average Breathing Rate in Hour2}) \quad \text{(Equation 3)}$$

Pattern analysis module 16 compares the combination score to a first threshold and a second threshold greater than the first. If the combination score is between the first and second thresholds, system 10 generates an alarm indicative of a future predicted clinical episode. If the combination score is greater than the second threshold, the system generates an alarm indicative of a currently occurring clinical episode. Alternatively, the scores and combination scores are vectors.

For some applications, these techniques are used in conjunction with the zone disease management methodology widely used by asthma patients, in which a "green" zone indicates no asthma symptoms, a "yellow" zone indicates a low level of attack, and a "red" zone indicates a high level of attack. System 10 drives user interface 24 to generate a green zone indication if the combination score is less than the first threshold, a yellow zone indication if the combination score is between the first and second thresholds, and a red zone indication if the combination score is greater than the second threshold.

For some applications, system 10 is configured to wake the subject from night sleep with an immediate alert if the combination score is greater than the second threshold, and to wait until morning to notify the subject if the combination score is between the first and second thresholds. The immediate alert may include an alarm sound and/or a light. A message which notifies the subject in the morning of a predicted onset of symptoms may be initially outputted from a user interface at any time after calculation of the combination score, in a manner that does not awaken the subject.

For some applications, system 10 is adapted to learn one or both of the thresholds, one or more of the parameters, and/or one or more of the constants used to generate the combination score. Techniques described hereinabove for such learning may be used.

Figure 24:
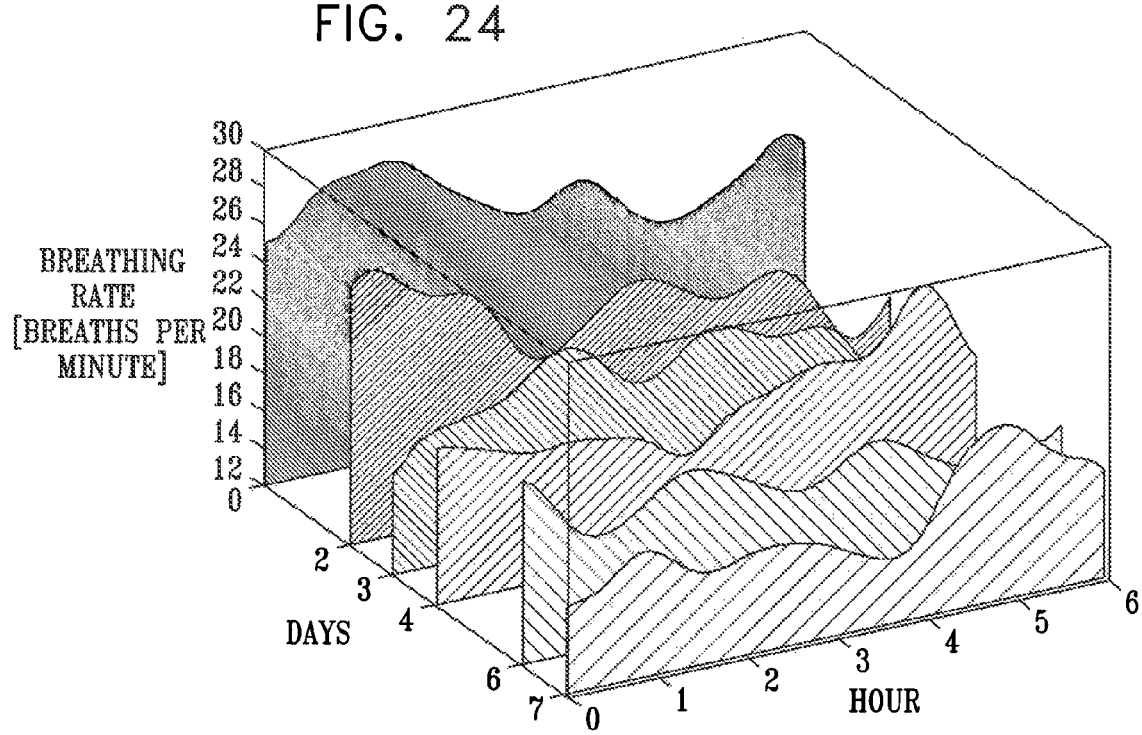
FIG. 24 is a three-dimensional graph illustrating breathing rate measured over several nights, in accordance with an embodiment of the present invention.

Reference is made to FIG. 24, which is a three-dimensional graph illustrating breathing rate measured over several nights, in accordance with an embodiment of the present invention. Such a graph is effective for visualizing the progression of a clinical episode and/or identifying an onset of the episode. The x-axis of the graph of FIG. 24 represents the hour of the night, the y-axis represents an index of the night (i.e., which 24-hour period), and the z-axis represents the respiration rate. Alternatively or additionally, heart rate is shown on the z-axis. Alternatively, such data is displayed topographically, or as a grey-scale or color-coded map. Analysis of such a three dimensional graphs either by a human or a machine is useful in identifying patterns which may indicate the onset of an episode.

In an embodiment of the present invention, system 10 comprises a plurality of motion sensors 30, such as a first sensor in a vicinity of abdomen 38 or chest 39, and a second sensor in a vicinity of legs 40, as described hereinabove with reference to FIG. 15. Pattern analysis module 16 determines the time delay between the pulse signal measured in the sensor under the abdomen or chest and the pulse signal measured under the legs. For example, the module may measure the time delay by performing a cross correlation between the heartbeat signals using a time window less than the respiration cycle time, such as between about 1 and 3 heart beat cycles. Alternatively, the module may identify the peaks in the heartbeat signals, and calculate the time differences between the peaks in each signal. Module 16 uses the time difference to calculate a blood pressure change signal on a continuous basis, for example as described in the above-mentioned U.S. Pat. No. 6,599,251 to Chen et al., mutatis mutandis. Module 16 calculates the amplitude in the change in blood pressure over a full inspiration/expiration cycle, and compares the amplitude to a threshold, such as 10 mmHg, or to a baseline value, either previously measured for the subject or based on a population average. Module 16 interprets an amplitude greater than the threshold as indicative of pulsus paradoxus. Alternatively or additionally, the system displays the amplitude and/or logs the amplitude to form a baseline for the specific patient which is later used to identify a change in condition.

Some embodiments described herein relate to a set of vital signs and physiological behaviors that are monitored in order to predict and/or monitor clinical episodes. In some cases, it is useful to combine some of these capabilities to improve the monitoring and/or prediction capabilities of system 10, for example, for detecting the onset of hypoglycemia in a diabetic patient, as described hereinabove.

In an embodiment of the present invention, system 10 is adapted to count the number of arousals during a night. For some applications, such a count serves as an indication for the onset of asthma attacks, diabetes deterioration (e.g., waking up to drink water), small bowel and/or colon related diseases, or prostate problems (e.g., waking up to urinate). In an embodiment, the identification of arousals is performed using techniques described hereinabove, and/or in the above-referenced article by Shinar Z et al. (1998).

In an embodiment of the present invention, system 10 is adapted to monitor a geriatric subject, typically without contacting or viewing the subject or clothes the subject is wearing. For example, system 10 may be configured to monitor one or more of respiration rate, heart rate, coughs, sleep time, wake up events, and restlessness in sleep. For some applications, system 10 analyzes one or more of these parameters to determine when the subject is attempting to get out of bed without assistance, and notifies a healthcare worker. Death or injury are often caused by patients' attempts to get out of bed without assistance.

In an embodiment of the present invention, system 10 is configured to identify a change in the condition of at least one patient in a hospital, such as in a surgical or medical ward. The change typically includes a deterioration that requires rapid intervention. System 10 typically identifies the change without contacting or viewing the patient or clothes the patient is wearing, without limiting the mobility of the patient, and without requiring any effort by the nursing staff or other healthcare workers. For example, upon detecting a decrease in the patient's respiration rate to below eight breaths per minute, which may be a sign of respiratory depression, the system may generate an alert to a nurse. For some applications, the system is configured to predict an onset of a clinical episode, and to generate an alert.

For some applications, system 10 monitors the patient in the hospital automatically upon entry of the patient into a bed. Typically, system 10 does not require activation by a nurse or other healthcare worker, and no compliance by the patient is required other than to be in bed. Typically, motion sensor 30 is contactless and operates substantially continuously. When the patient enters the bed, the sensor detects the vibrations or other movements generated by the patient and initiates monitoring. The system alerts clinicians upon any change that may require intervention. For example, the system may send an alert to a nurse, a member of a rapid response team, or other healthcare worker, such as wirelessly, e.g., to a wireless communication device, such as a pager, or using another call system in the hospital. For some applications, upon receiving the message, the wireless communication device sounds an audible alert, e.g., including an automatically generated voice message that includes the patient's name or number, room number, and/or alert type. This enables a clinician to act upon the alert and/or assess the situation without having to handle the pager (which is useful in situation where the clinician's hands are busy).

For some applications, when the patient enters the bed, system 10 initially uses a preset threshold for alerts. Over a period of time, e.g., one hour, the system establishes a reference baseline, e.g., the average respiration rate over that time period. Once the baseline has been established, upon identifying a change (e.g., a rapid change) in a clinical parameter versus the baseline, the system alerts a clinician. For example, the system may generate an alert upon detecting a change of 35% in a clinical parameter rate within a 15 minute period.

For some applications, the system makes a decision whether to generate an alert responsively to at least one clinical parameter selected from the group consisting of: a current value of the clinical parameter, a change in the clinical parameter versus baseline, and a rate of change of the clinical parameter over a relatively brief period of time, such as over a period of time having a duration of between about 2 and about 180 minutes, e.g., between about 10 and about 20 minutes. For some applications, the system uses a score which combines two or more of these parameters. For example, the score may include a weighted average of two or more of the parameters, e.g.:

$$Score = K*Param + J*DeltaParam + L*DeltaParamRate \quad \text{(Equation 4)}$$

where K, J, and L are coefficients (e.g., equal to 1, 0.2, and 0.4, respectively); Param is the current value of the clinical parameter, for example respiration rate or heart rate; DeltaParam is the difference (e.g., expressed as a percentage) of the parameter versus the patient's baseline; and DeltaParamRate is the change in percent of the parameter between the current time and that in a previous time period, for example between about 10 and about 20 minutes earlier, e.g., about 15 minutes earlier. Typically, Param has a unit of measurement, e.g., breaths per minute, or heartbeats per minute, while DeltaParam and DeltaParamRate do not have units. For some applications, Param is normalized, such as by dividing the measured value by the baseline value and multiplying by a constant, e.g., 100. For example, the upper and lower thresholds for Score may be set to 6 and 40, respectively, for monitoring respiration rate. If Score falls outside the range between the thresholds, the system generates an alert.

For some applications, sensor 30 is installed in a chair near the patient's bed.

For some applications, the baseline is deleted if the system detects that the bed is empty for a certain period of time, e.g., one hour, which may indicate that the patient has left the bed and a new patient has entered the bed.

For some applications, system 10 comprises a user interface that enables a clinician to enter a patient change, threshold levels, and/or other information.

Although some embodiments described herein relate specifically to asthmatic episodes or CHF, the principles of the present invention may be applied, mutatis mutandis, to predicting and monitoring other respiratory and non-respiratory conditions that affect normal breathing patterns, such as chronic obstructive pulmonary disease (COPD), cystic fibrosis (CF), diabetes, a neurological disorder (e.g., epilepsy), and certain heart diseases in addition to CHF. For some applications, system 10 is configured to predict the onset of and/or monitor a migraine headache, such as by monitoring changes in respiration rate and/or heart rate, which are early indications of an approaching migraine. For some applications, system 10 is configured to monitor movement of the small bowel and/or colon movement, and to analyze such motion as an indication for gastrointestinal conditions. For example, system 10 may identify characteristic frequencies of gastrointestinal tract movement, such as by differentiating between signals generated by a sensor under the abdomen and a sensor under the lungs.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for monitoring a subject, comprising:
setting respective first and second thresholds that are different from one another;
sensing at least one parameter of the subject;
analyzing the sensed parameter to generate a score;
if the score is between the first and second thresholds, generating an alert that is indicative of a condition of the subject only after the subject awakes; and
if the score passes the second threshold, generating an immediate alert that is indicative of the subject's condition.

2. Apparatus for monitoring a subject, comprising:
a sensor, adapted to sense at least one parameter of a subject;
a user interface; and
a control unit, adapted to:
set respective first and second thresholds that are different from one another,
analyze the sensed parameter to generate a score,
if the score is between the first and second thresholds, drive the user interface to generate an alert that is indicative of a condition of the subject only after the subject awakes, and
if the score passes the second threshold, drive the user interface to generate an immediate alert that is indicative of the subject's condition.

3. The method according to claim 1, wherein:
generating the alert that is indicative of the condition of the subject only after the subject awakes comprises generating an alert indicative of a future predicted clinical episode, and generating the immediate alert that is indicative of the subject's condition comprises generating an alert indicative of a currently occurring clinical episode.

4. The method according to claim 1, wherein:

generating the alert that is indicative of the condition of the subject only after the subject awakes comprises generating an alert indicative of a low level of asthma attack, and generating the immediate alert that is indicative of the subject's condition comprises generating an alert indicative of a high level of asthma attack.

5. The apparatus according to claim 2, wherein the control unit is adapted to:

if the score is between the first and second thresholds, drive the user interface to generate an alert that is indicative of a future predicted clinical episode of the subject, only after the subject awakes, and if the score passes the second threshold, drive the user interface to generate an immediate alert that is indicative of a currently occurring clinical episode of the subject.

6. The apparatus according to claim 2, wherein the control unit is configured to:

if the score is between the first and second thresholds, drive the user interface to generate an alert that is indicative of a low level of asthma attack of the subject, only after the subject awakes, and if the score passes the second threshold, drive the user interface to generate an immediate alert that is indicative of a high level of asthma attack of the subject.

\* \* \* \* \*